(12) United States Patent
Crawford et al.

(10) Patent No.: US 11,135,015 B2
(45) Date of Patent: Oct. 5, 2021

(54) ROBOT SURGICAL PLATFORM

(71) Applicant: GLOBUS MEDICAL, INC., Audubon, PA (US)

(72) Inventors: Neil R. Crawford, Chandler, AZ (US); Norbert Johnson, North Andover, MA (US)

(73) Assignee: Globus Medical, Inc., Audubon, PA (US)

( * ) Notice: Subject to any disclaimer, the term of this patent is extended or adjusted under 35 U.S.C. 154(b) by 36 days.

(21) Appl. No.: 16/037,175

(22) Filed: Jul. 17, 2018

(65) Prior Publication Data

US 2019/0021800 A1   Jan. 24, 2019

Related U.S. Application Data

(60) Provisional application No. 62/535,591, filed on Jul. 21, 2017.

(51) Int. Cl.
*G09G 5/00* (2006.01)
*A61B 34/10* (2016.01)
(Continued)

(52) U.S. Cl.
CPC .............. *A61B 34/10* (2016.02); *A61B 6/487* (2013.01); *A61B 6/547* (2013.01); *A61B 17/56* (2013.01); *A61B 17/7001* (2013.01); *A61B 17/7074* (2013.01); *A61B 34/20* (2016.02); *A61B 34/25* (2016.02); *A61B 34/30* (2016.02); *A61B 34/71* (2016.02); *A61B 34/74* (2016.02); *A61B 90/37* (2016.02); *G06F 3/0488* (2013.01);
(Continued)

(58) Field of Classification Search
CPC ......... A61B 17/56; A61B 34/10; A61B 34/00; A61B 34/30
See application file for complete search history.

(56) References Cited

U.S. PATENT DOCUMENTS

| | | |
|---|---|---|
| 4,150,293 A | 4/1979 | Franke |
| 5,246,010 A | 9/1993 | Gazzara et al. |

(Continued)

FOREIGN PATENT DOCUMENTS

| | | |
|---|---|---|
| WO | 2016102026 A1 | 6/2016 |
| WO | 2017003916 A1 | 1/2017 |

OTHER PUBLICATIONS

US 8,231,638 B2, 07/2012, Swarup et al. (withdrawn)

Primary Examiner — Weiming He

(57) ABSTRACT

A surgical implant planning computer for intra-operative CT workflow, pre-operative CT imaging workflow, and fluoroscopic imaging workflow. A network interface is connectable to a CT image scanner and a robot surgical platform having a robot base coupled to a robot arm that is movable by motors. A CT image of a bone is received from the CT image scanner and displayed. A user's selection is received of a surgical screw from among a set of defined surgical screws. A graphical screw representing the selected surgical screw is displayed as an overlay on the CT image of the bone. Angular orientation and location of the displayed graphical screw relative to the bone in the CT image is controlled responsive to receipt of user inputs. An indication of the selected surgical screw and an angular orientation and a location of the displayed graphical screw are stored in a surgical plan data structure.

20 Claims, 46 Drawing Sheets

(51) Int. Cl.

| | | |
|---|---|---|
| *A61B 34/30* | (2016.01) | |
| *A61B 34/00* | (2016.01) | |
| *A61B 90/00* | (2016.01) | |
| *G06F 3/0488* | (2013.01) | |
| *A61B 17/56* | (2006.01) | |
| *A61B 34/20* | (2016.01) | |
| *G16H 30/20* | (2018.01) | |
| *G16H 40/63* | (2018.01) | |
| *A61B 6/00* | (2006.01) | |
| *A61B 17/70* | (2006.01) | |
| *B25J 9/06* | (2006.01) | |
| *B25J 9/00* | (2006.01) | |
| *A61B 90/13* | (2016.01) | |
| *A61B 17/00* | (2006.01) | |

(52) U.S. Cl.
CPC ............ *G16H 30/20* (2018.01); *G16H 40/63* (2018.01); *A61B 90/13* (2016.02); *A61B 2017/00199* (2013.01); *A61B 2034/102* (2016.02); *A61B 2034/107* (2016.02); *A61B 2034/108* (2016.02); *A61B 2034/207* (2016.02); *A61B 2034/2055* (2016.02); *A61B 2034/2057* (2016.02); *A61B 2034/2072* (2016.02); *A61B 2034/252* (2016.02); *A61B 2034/254* (2016.02); *A61B 2034/256* (2016.02); *A61B 2034/304* (2016.02); *A61B 2034/305* (2016.02); *A61B 2090/363* (2016.02); *A61B 2090/365* (2016.02); *A61B 2090/371* (2016.02); *A61B 2090/376* (2016.02); *A61B 2090/3762* (2016.02); *A61B 2090/3937* (2016.02); *A61B 2090/3983* (2016.02); *A61B 2560/0475* (2013.01); *B25J 9/0021* (2013.01); *B25J 9/06* (2013.01)

(56) References Cited

U.S. PATENT DOCUMENTS

| | | |
|---|---|---|
| 5,354,314 A | 10/1994 | Hardy et al. |
| 5,397,323 A | 3/1995 | Taylor et al. |
| 5,598,453 A | 1/1997 | Baba et al. |
| 5,772,594 A | 6/1998 | Barrick |
| 5,791,908 A | 8/1998 | Gillio |
| 5,820,559 A | 10/1998 | Ng et al. |
| 5,825,982 A | 10/1998 | Wright et al. |
| 5,887,121 A | 3/1999 | Funda et al. |
| 5,911,449 A | 6/1999 | Daniele et al. |
| 5,951,475 A | 9/1999 | Gueziec et al. |
| 5,987,960 A | 11/1999 | Messner et al. |
| 6,012,216 A | 1/2000 | Esteves et al. |
| 6,031,888 A | 2/2000 | Ivan et al. |
| 6,033,415 A | 3/2000 | Mittelstadt et al. |
| 6,080,181 A | 6/2000 | Jensen et al. |
| 6,106,511 A | 8/2000 | Jensen |
| 6,122,541 A | 9/2000 | Cosman et al. |
| 6,144,875 A | 11/2000 | Schweikard et al. |
| 6,157,853 A | 12/2000 | Blume et al. |
| 6,167,145 A | 12/2000 | Foley et al. |
| 6,167,292 A | 12/2000 | Badano et al. |
| 6,201,984 B1 | 3/2001 | Funda et al. |
| 6,203,196 B1 | 3/2001 | Meyer et al. |
| 6,205,411 B1 | 3/2001 | DiGioia, III et al. |
| 6,212,419 B1 | 4/2001 | Blume et al. |
| 6,231,565 B1 | 5/2001 | Tovey et al. |
| 6,236,875 B1 | 5/2001 | Bucholz et al. |
| 6,246,900 B1 | 6/2001 | Cosman et al. |
| 6,301,495 B1 | 10/2001 | Gueziec et al. |
| 6,306,126 B1 | 10/2001 | Montezuma |
| 6,312,435 B1 | 11/2001 | Wallace et al. |
| 6,314,311 B1 | 11/2001 | Williams et al. |
| 6,320,929 B1 | 11/2001 | Von Der Haar |
| 6,322,567 B1 | 11/2001 | Mittelstadt et al. |
| 6,325,808 B1 | 12/2001 | Bernard et al. |
| 6,340,363 B1 | 1/2002 | Bolger et al. |
| 6,377,011 B1 | 4/2002 | Ben-Ur |
| 6,379,302 B1 | 4/2002 | Kessman et al. |
| 6,402,762 B2 | 6/2002 | Hunter et al. |
| 6,424,885 B1 | 7/2002 | Niemeyer et al. |
| 6,447,503 B1 | 9/2002 | Wynne et al. |
| 6,451,027 B1 | 9/2002 | Cooper et al. |
| 6,477,400 B1 | 11/2002 | Barrick |
| 6,484,049 B1 | 11/2002 | Seeley et al. |
| 6,487,267 B1 | 11/2002 | Wolter |
| 6,490,467 B1 | 12/2002 | Bucholz et al. |
| 6,490,475 B1 | 12/2002 | Seeley et al. |
| 6,499,488 B1 | 12/2002 | Hunter et al. |
| 6,501,981 B1 | 12/2002 | Schweikard et al. |
| 6,507,751 B2 | 1/2003 | Blume et al. |
| 6,535,756 B1 | 3/2003 | Simon et al. |
| 6,560,354 B1 | 5/2003 | Maurer, Jr. et al. |
| 6,565,554 B1 | 5/2003 | Niemeyer |
| 6,587,750 B2 | 7/2003 | Gerbi et al. |
| 6,614,453 B1 | 9/2003 | Suri et al. |
| 6,614,871 B1 | 9/2003 | Kobiki et al. |
| 6,619,840 B2 | 9/2003 | Rasche et al. |
| 6,636,757 B1 | 10/2003 | Jascob et al. |
| 6,645,196 B1 | 11/2003 | Nixon et al. |
| 6,666,579 B2 | 12/2003 | Jensen |
| 6,669,635 B2 | 12/2003 | Kessman et al. |
| 6,701,173 B2 | 3/2004 | Nowinski et al. |
| 6,757,068 B2 | 6/2004 | Foxlin |
| 6,782,287 B2 | 8/2004 | Grzeszczuk et al. |
| 6,783,524 B2 | 8/2004 | Anderson et al. |
| 6,786,896 B1 | 9/2004 | Madhani et al. |
| 6,788,018 B1 | 9/2004 | Blumenkranz |
| 6,804,581 B2 | 10/2004 | Wang et al. |
| 6,823,207 B1 | 11/2004 | Jensen et al. |
| 6,827,351 B2 | 12/2004 | Graziani et al. |
| 6,837,892 B2 | 1/2005 | Shoham |
| 6,839,612 B2 | 1/2005 | Sanchez et al. |
| 6,856,826 B2 | 2/2005 | Seeley et al. |
| 6,856,827 B2 | 2/2005 | Seeley et al. |
| 6,879,880 B2 | 4/2005 | Nowlin et al. |
| 6,892,090 B2 | 5/2005 | Verard et al. |
| 6,920,347 B2 | 7/2005 | Simon et al. |
| 6,922,632 B2 | 7/2005 | Foxlin |
| 6,968,224 B2 | 11/2005 | Kessman et al. |
| 6,978,166 B2 | 12/2005 | Foley et al. |
| 6,988,009 B2 | 1/2006 | Grimm et al. |
| 6,991,627 B2 | 1/2006 | Madhani et al. |
| 6,996,487 B2 | 2/2006 | Jutras et al. |
| 6,999,852 B2 | 2/2006 | Green |
| 7,007,699 B2 | 3/2006 | Martinelli et al. |
| 7,016,457 B1 | 3/2006 | Senzig et al. |
| 7,043,961 B2 | 5/2006 | Pandey et al. |
| 7,062,006 B1 | 6/2006 | Pelc et al. |
| 7,063,705 B2 | 6/2006 | Young et al. |
| 7,072,707 B2 | 7/2006 | Galloway, Jr. et al. |
| 7,083,615 B2 | 8/2006 | Peterson et al. |
| 7,097,640 B2 | 8/2006 | Wang et al. |
| 7,099,428 B2 | 8/2006 | Clinthorne et al. |
| 7,108,421 B2 | 9/2006 | Gregerson et al. |
| 7,130,676 B2 | 10/2006 | Barrick |
| 7,139,418 B2 | 11/2006 | Abovitz et al. |
| 7,139,601 B2 | 11/2006 | Bucholz et al. |
| 7,155,316 B2 | 12/2006 | Sutherland et al. |
| 7,164,968 B2 | 1/2007 | Treat et al. |
| 7,167,738 B2 | 1/2007 | Schweikard et al. |
| 7,169,141 B2 | 1/2007 | Brock et al. |
| 7,172,627 B2 | 2/2007 | Fiere et al. |
| 7,194,120 B2 | 3/2007 | Wicker et al. |
| 7,197,107 B2 | 3/2007 | Arai et al. |
| 7,231,014 B2 | 6/2007 | Levy |
| 7,231,063 B2 | 6/2007 | Naimark et al. |
| 7,239,940 B2 | 7/2007 | Wang et al. |
| 7,248,914 B2 | 7/2007 | Hastings et al. |
| 7,301,648 B2 | 11/2007 | Foxlin |
| 7,302,288 B1 | 11/2007 | Schellenberg |
| 7,313,430 B2 | 12/2007 | Urquhart et al. |
| 7,318,805 B2 | 1/2008 | Schweikard et al. |
| 7,318,827 B2 | 1/2008 | Leitner et al. |

(56) References Cited

U.S. PATENT DOCUMENTS

| | | |
|---|---|---|
| 7,319,897 B2 | 1/2008 | Leitner et al. |
| 7,324,623 B2 | 1/2008 | Heuscher et al. |
| 7,327,865 B2 | 2/2008 | Fu et al. |
| 7,331,967 B2 | 2/2008 | Lee et al. |
| 7,333,642 B2 | 2/2008 | Green |
| 7,339,341 B2 | 3/2008 | Oleynikov et al. |
| 7,366,562 B2 | 4/2008 | Dukesherer et al. |
| 7,379,790 B2 | 5/2008 | Toth et al. |
| 7,386,365 B2 | 6/2008 | Nixon |
| 7,422,592 B2 | 9/2008 | Morley et al. |
| 7,435,216 B2 | 10/2008 | Kwon et al. |
| 7,440,793 B2 | 10/2008 | Chauhan et al. |
| 7,460,637 B2 | 12/2008 | Clinthorne et al. |
| 7,466,303 B2 | 12/2008 | Yi et al. |
| 7,493,153 B2 | 2/2009 | Ahmed et al. |
| 7,505,617 B2 | 3/2009 | Fu et al. |
| 7,533,892 B2 | 5/2009 | Schena et al. |
| 7,542,791 B2 | 6/2009 | Mire et al. |
| 7,555,331 B2 | 6/2009 | Viswanathan |
| 7,567,834 B2 | 7/2009 | Clayton et al. |
| 7,594,912 B2 | 9/2009 | Cooper et al. |
| 7,606,613 B2 | 10/2009 | Simon et al. |
| 7,607,440 B2 | 10/2009 | Coste-Maniere et al. |
| 7,623,902 B2 | 11/2009 | Pacheco |
| 7,630,752 B2 | 12/2009 | Viswanathan |
| 7,630,753 B2 | 12/2009 | Simon et al. |
| 7,643,862 B2 | 1/2010 | Schoenefeld |
| 7,660,623 B2 | 2/2010 | Hunter et al. |
| 7,661,881 B2 | 2/2010 | Gregerson et al. |
| 7,683,331 B2 | 3/2010 | Chang |
| 7,683,332 B2 | 3/2010 | Chang |
| 7,689,320 B2 | 3/2010 | Prisco et al. |
| 7,691,098 B2 | 4/2010 | Wallace et al. |
| 7,702,379 B2 | 4/2010 | Avinash et al. |
| 7,702,477 B2 | 4/2010 | Tuemmler et al. |
| 7,711,083 B2 | 5/2010 | Heigl et al. |
| 7,711,406 B2 | 5/2010 | Kuhn et al. |
| 7,720,523 B2 | 5/2010 | Omernick et al. |
| 7,725,253 B2 | 5/2010 | Foxlin |
| 7,726,171 B2 | 6/2010 | Langlotz et al. |
| 7,742,801 B2 | 6/2010 | Neubauer et al. |
| 7,751,865 B2 | 7/2010 | Jascob et al. |
| 7,760,849 B2 | 7/2010 | Zhang |
| 7,762,825 B2 | 7/2010 | Burbank et al. |
| 7,763,015 B2 | 7/2010 | Cooper et al. |
| 7,787,699 B2 | 8/2010 | Mahesh et al. |
| 7,796,728 B2 | 9/2010 | Bergfjord |
| 7,813,838 B2 | 10/2010 | Sommer |
| 7,818,044 B2 | 10/2010 | Dukesherer et al. |
| 7,819,859 B2 | 10/2010 | Prisco et al. |
| 7,824,401 B2 | 11/2010 | Manzo et al. |
| 7,831,294 B2 | 11/2010 | Viswanathan |
| 7,834,484 B2 | 11/2010 | Sartor |
| 7,835,557 B2 | 11/2010 | Kendrick et al. |
| 7,835,778 B2 | 11/2010 | Foley et al. |
| 7,835,784 B2 | 11/2010 | Mire et al. |
| 7,840,253 B2 | 11/2010 | Tremblay et al. |
| 7,840,256 B2 | 11/2010 | Lakin et al. |
| 7,843,158 B2 | 11/2010 | Prisco |
| 7,844,320 B2 | 11/2010 | Shahidi |
| 7,853,305 B2 | 12/2010 | Simon et al. |
| 7,853,313 B2 | 12/2010 | Thompson |
| 7,865,269 B2 | 1/2011 | Prisco et al. |
| D631,966 S | 2/2011 | Perloff et al. |
| 7,879,045 B2 | 2/2011 | Gielen et al. |
| 7,881,767 B2 | 2/2011 | Strommer et al. |
| 7,881,770 B2 | 2/2011 | Melkent et al. |
| 7,886,743 B2 | 2/2011 | Cooper et al. |
| RE42,194 E | 3/2011 | Foley et al. |
| RE42,226 E | 3/2011 | Foley et al. |
| 7,900,524 B2 | 3/2011 | Calloway et al. |
| 7,907,166 B2 | 3/2011 | Lamprecht et al. |
| 7,909,122 B2 | 3/2011 | Schena et al. |
| 7,925,653 B2 | 4/2011 | Saptharishi |
| 7,930,065 B2 | 4/2011 | Larkin et al. |
| 7,935,130 B2 | 5/2011 | Williams |
| 7,940,999 B2 | 5/2011 | Liao et al. |
| 7,945,012 B2 | 5/2011 | Ye et al. |
| 7,945,021 B2 | 5/2011 | Shapiro et al. |
| 7,953,470 B2 | 5/2011 | Vetter et al. |
| 7,954,397 B2 | 6/2011 | Choi et al. |
| 7,971,341 B2 | 7/2011 | Dukesherer et al. |
| 7,974,674 B2 | 7/2011 | Hauck et al. |
| 7,974,677 B2 | 7/2011 | Mire et al. |
| 7,974,681 B2 | 7/2011 | Wallace et al. |
| 7,979,157 B2 | 7/2011 | Anvari |
| 7,983,733 B2 | 7/2011 | Viswanathan |
| 7,988,215 B2 | 8/2011 | Seibold |
| 7,996,110 B2 | 8/2011 | Lipow et al. |
| 8,004,121 B2 | 8/2011 | Sartor |
| 8,004,229 B2 | 8/2011 | Nowlin et al. |
| 8,010,177 B2 | 8/2011 | Csavoy et al. |
| 8,019,045 B2 | 9/2011 | Kato |
| 8,021,310 B2 | 9/2011 | Sanborn et al. |
| 8,035,685 B2 | 10/2011 | Jensen |
| 8,046,054 B2 | 10/2011 | Kim et al. |
| 8,046,057 B2 | 10/2011 | Clarke |
| 8,052,688 B2 | 11/2011 | Wolf, II |
| 8,054,184 B2 | 11/2011 | Cline et al. |
| 8,054,752 B2 | 11/2011 | Druke et al. |
| 8,057,397 B2 | 11/2011 | Li et al. |
| 8,057,407 B2 | 11/2011 | Martinelli et al. |
| 8,062,288 B2 | 11/2011 | Cooper et al. |
| 8,062,375 B2 | 11/2011 | Glerum et al. |
| 8,066,524 B2 | 11/2011 | Burbank et al. |
| 8,073,335 B2 | 12/2011 | Labonville et al. |
| 8,079,950 B2 | 12/2011 | Stern et al. |
| 8,086,299 B2 | 12/2011 | Adler et al. |
| 8,092,370 B2 | 1/2012 | Roberts et al. |
| 8,098,914 B2 | 1/2012 | Liao et al. |
| 8,100,950 B2 | 1/2012 | St. Clair et al. |
| 8,105,320 B2 | 1/2012 | Manzo |
| 8,108,025 B2 | 1/2012 | Csavoy et al. |
| 8,109,877 B2 | 2/2012 | Moctezuma de la Barrera et al. |
| 8,112,292 B2 | 2/2012 | Simon |
| 8,116,430 B1 | 2/2012 | Shapiro et al. |
| 8,120,301 B2 | 2/2012 | Goldberg et al. |
| 8,121,249 B2 | 2/2012 | Wang et al. |
| 8,123,675 B2 | 2/2012 | Funda et al. |
| 8,133,229 B1 | 3/2012 | Bonutti |
| 8,142,420 B2 | 3/2012 | Schena |
| 8,147,494 B2 | 4/2012 | Leitner et al. |
| 8,150,494 B2 | 4/2012 | Simon et al. |
| 8,150,497 B2 | 4/2012 | Gielen et al. |
| 8,150,498 B2 | 4/2012 | Gielen et al. |
| 8,165,658 B2 | 4/2012 | Waynik et al. |
| 8,170,313 B2 | 5/2012 | Kendrick et al. |
| 8,179,073 B2 | 5/2012 | Farritor et al. |
| 8,182,476 B2 | 5/2012 | Julian et al. |
| 8,184,880 B2 | 5/2012 | Zhao et al. |
| 8,202,278 B2 | 6/2012 | Orban, III et al. |
| 8,208,708 B2 | 6/2012 | Homan et al. |
| 8,208,988 B2 | 6/2012 | Jensen |
| 8,219,177 B2 | 7/2012 | Smith et al. |
| 8,219,178 B2 | 7/2012 | Smith et al. |
| 8,220,468 B2 | 7/2012 | Cooper et al. |
| 8,224,024 B2 | 7/2012 | Foxlin et al. |
| 8,224,484 B2 | 7/2012 | Swarup et al. |
| 8,225,798 B2 | 7/2012 | Baldwin et al. |
| 8,228,368 B2 | 7/2012 | Zhao et al. |
| 8,231,610 B2 | 7/2012 | Jo et al. |
| 8,263,933 B2 | 7/2012 | Hartmann et al. |
| 8,239,001 B2 | 8/2012 | Verard et al. |
| 8,241,271 B2 | 8/2012 | Millman et al. |
| 8,248,413 B2 | 8/2012 | Gattani et al. |
| 8,256,319 B2 | 9/2012 | Cooper et al. |
| 8,271,069 B2 | 9/2012 | Jascob et al. |
| 8,271,130 B2 | 9/2012 | Hourtash |
| 8,281,670 B2 | 10/2012 | Larkin et al. |
| 8,282,653 B2 | 10/2012 | Nelson et al. |
| 8,301,226 B2 | 10/2012 | Csavoy et al. |
| 8,311,611 B2 | 11/2012 | Csavoy et al. |
| 8,320,991 B2 | 11/2012 | Jascob et al. |
| 8,332,012 B2 | 12/2012 | Kienzle, III |

(56) References Cited

U.S. PATENT DOCUMENTS

| | | |
|---|---|---|
| 8,333,755 B2 | 12/2012 | Cooper et al. |
| 8,335,552 B2 | 12/2012 | Stiles |
| 8,335,557 B2 | 12/2012 | Maschke |
| 8,348,931 B2 | 1/2013 | Cooper et al. |
| 8,353,963 B2 | 1/2013 | Glerum |
| 8,358,818 B2 | 1/2013 | Miga et al. |
| 8,359,730 B2 | 1/2013 | Burg et al. |
| 8,374,673 B2 | 2/2013 | Adcox et al. |
| 8,374,723 B2 | 2/2013 | Zhao et al. |
| 8,379,791 B2 | 2/2013 | Forthmann et al. |
| 8,386,019 B2 | 2/2013 | Camus et al. |
| 8,392,022 B2 | 3/2013 | Ortmaier et al. |
| 8,394,099 B2 | 3/2013 | Patwardhan |
| 8,395,342 B2 | 3/2013 | Prisco |
| 8,398,634 B2 | 3/2013 | Manzo et al. |
| 8,400,094 B2 | 3/2013 | Schena |
| 8,414,957 B2 | 4/2013 | Enzerink et al. |
| 8,418,073 B2 | 4/2013 | Mohr et al. |
| 8,450,694 B2 | 5/2013 | Baviera et al. |
| 8,452,447 B2 | 5/2013 | Nixon |
| RE44,305 E | 6/2013 | Foley et al. |
| 8,462,911 B2 | 6/2013 | Vesel et al. |
| 8,465,476 B2 | 6/2013 | Rogers et al. |
| 8,465,771 B2 | 6/2013 | Wan et al. |
| 8,467,851 B2 | 6/2013 | Mire et al. |
| 8,467,852 B2 | 6/2013 | Csavoy et al. |
| 8,469,947 B2 | 6/2013 | Devengenzo et al. |
| RE44,392 E | 7/2013 | Hynes |
| 8,483,434 B2 | 7/2013 | Buehner et al. |
| 8,483,800 B2 | 7/2013 | Jensen et al. |
| 8,486,532 B2 | 7/2013 | Enzerink et al. |
| 8,489,235 B2 | 7/2013 | Moll et al. |
| 8,500,722 B2 | 8/2013 | Cooper |
| 8,500,728 B2 | 8/2013 | Newton et al. |
| 8,504,201 B2 | 8/2013 | Moll et al. |
| 8,506,555 B2 | 8/2013 | Ruiz Morales |
| 8,506,556 B2 | 8/2013 | Schena |
| 8,508,173 B2 | 8/2013 | Goldberg et al. |
| 8,512,318 B2 | 8/2013 | Tovey et al. |
| 8,515,576 B2 | 8/2013 | Lipow et al. |
| 8,518,120 B2 | 8/2013 | Glerum et al. |
| 8,521,331 B2 | 8/2013 | Itkowitz |
| 8,526,688 B2 | 9/2013 | Groszmann et al. |
| 8,526,700 B2 | 9/2013 | Issacs |
| 8,527,094 B2 | 9/2013 | Kumar et al. |
| 8,528,440 B2 | 9/2013 | Morley et al. |
| 8,532,741 B2 | 9/2013 | Heruth et al. |
| 8,541,970 B2 | 9/2013 | Nowlin et al. |
| 8,548,563 B2 | 10/2013 | Simon et al. |
| 8,549,732 B2 | 10/2013 | Burg et al. |
| 8,551,114 B2 | 10/2013 | Ramos de la Pena |
| 8,551,116 B2 | 10/2013 | Julian et al. |
| 8,556,807 B2 | 10/2013 | Scott et al. |
| 8,556,979 B2 | 10/2013 | Glerum et al. |
| 8,560,118 B2 | 10/2013 | Green et al. |
| 8,561,473 B2 | 10/2013 | Blumenkranz |
| 8,562,594 B2 | 10/2013 | Cooper et al. |
| 8,571,638 B2 | 10/2013 | Shoham |
| 8,571,710 B2 | 10/2013 | Coste-Maniere et al. |
| 8,573,465 B2 | 11/2013 | Shelton, IV |
| 8,574,303 B2 | 11/2013 | Sharkey et al. |
| 8,585,420 B2 | 11/2013 | Burbank et al. |
| 8,594,841 B2 | 11/2013 | Zhao et al. |
| 8,597,198 B2 | 12/2013 | Sanborn et al. |
| 8,600,478 B2 | 12/2013 | Verard et al. |
| 8,603,077 B2 | 12/2013 | Cooper et al. |
| 8,611,985 B2 | 12/2013 | Lavallee et al. |
| 8,613,230 B2 | 12/2013 | Blumenkranz et al. |
| 8,621,939 B2 | 1/2014 | Blumenkranz et al. |
| 8,624,537 B2 | 1/2014 | Nowlin et al. |
| 8,630,389 B2 | 1/2014 | Kato |
| 8,634,897 B2 | 1/2014 | Simon et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,639,000 B2 | 1/2014 | Zhao et al. |
| 8,641,726 B2 | 2/2014 | Bonutti |
| 8,644,907 B2 | 2/2014 | Hartmann et al. |
| 8,657,809 B2 | 2/2014 | Schoepp |
| 8,660,635 B2 | 2/2014 | Simon et al. |
| 8,666,544 B2 | 3/2014 | Moll et al. |
| 8,675,939 B2 | 3/2014 | Moctezuma de la Barrera |
| 8,678,647 B2 | 3/2014 | Gregerson et al. |
| 8,679,125 B2 | 3/2014 | Smith et al. |
| 8,679,183 B2 | 3/2014 | Glerum et al. |
| 8,682,413 B2 | 3/2014 | Lloyd |
| 8,684,253 B2 | 4/2014 | Giordano et al. |
| 8,685,098 B2 | 4/2014 | Glerum et al. |
| 8,693,730 B2 | 4/2014 | Umasuthan et al. |
| 8,694,075 B2 | 4/2014 | Groszmann et al. |
| 8,696,458 B2 | 4/2014 | Foxlin et al. |
| 8,700,123 B2 | 4/2014 | Okamura et al. |
| 8,706,086 B2 | 4/2014 | Glerum |
| 8,706,185 B2 | 4/2014 | Foley et al. |
| 8,706,301 B2 | 4/2014 | Zhao et al. |
| 8,717,430 B2 | 5/2014 | Simon et al. |
| 8,727,618 B2 | 5/2014 | Maschke et al. |
| 8,734,432 B2 | 5/2014 | Tuma et al. |
| 8,738,115 B2 | 5/2014 | Amberg et al. |
| 8,738,181 B2 | 5/2014 | Greer et al. |
| 8,740,882 B2 | 6/2014 | Jun et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,761,930 B2 | 6/2014 | Nixon |
| 8,764,448 B2 | 7/2014 | Yang et al. |
| 8,771,170 B2 | 7/2014 | Mesallum et al. |
| 8,781,186 B2 | 7/2014 | Clements et al. |
| 8,781,630 B2 | 7/2014 | Banks et al. |
| 8,784,385 B2 | 7/2014 | Boyden et al. |
| 8,786,241 B2 | 7/2014 | Nowlin et al. |
| 8,787,520 B2 | 7/2014 | Baba |
| 8,792,704 B2 | 7/2014 | Isaacs |
| 8,798,231 B2 | 8/2014 | Notohara et al. |
| 8,800,838 B2 | 8/2014 | Shelton, IV |
| 8,808,164 B2 | 8/2014 | Hoffman et al. |
| 8,812,077 B2 | 8/2014 | Dempsey |
| 8,814,793 B2 | 8/2014 | Brabrand |
| 8,816,628 B2 | 8/2014 | Nowlin et al. |
| 8,818,105 B2 | 8/2014 | Myronenko et al. |
| 8,820,605 B2 | 9/2014 | Shelton, IV |
| 8,821,511 B2 | 9/2014 | von Jako et al. |
| 8,823,308 B2 | 9/2014 | Nowlin et al. |
| 8,827,996 B2 | 9/2014 | Scott et al. |
| 8,828,024 B2 | 9/2014 | Farritor et al. |
| 8,830,224 B2 | 9/2014 | Zhao et al. |
| 8,834,489 B2 | 9/2014 | Cooper et al. |
| 8,834,490 B2 | 9/2014 | Bonutti |
| 8,838,270 B2 | 9/2014 | Druke et al. |
| 8,844,789 B2 | 9/2014 | Shelton, IV et al. |
| 8,855,822 B2 | 10/2014 | Bartol et al. |
| 8,858,598 B2 | 10/2014 | Seifert et al. |
| 8,860,753 B2 | 10/2014 | Bhandarkar et al. |
| 8,864,751 B2 | 10/2014 | Prisco et al. |
| 8,864,798 B2 | 10/2014 | Weiman et al. |
| 8,864,833 B2 | 10/2014 | Glerum et al. |
| 8,867,703 B2 | 10/2014 | Shapiro et al. |
| 8,870,880 B2 | 10/2014 | Himmelberger et al. |
| 8,876,866 B2 | 11/2014 | Zappacosta et al. |
| 8,880,223 B2 | 11/2014 | Raj et al. |
| 8,882,803 B2 | 11/2014 | Iott et al. |
| 8,883,210 B1 | 11/2014 | Truncale et al. |
| 8,888,821 B2 | 11/2014 | Rezach et al. |
| 8,888,853 B2 | 11/2014 | Glerum et al. |
| 8,888,854 B2 | 11/2014 | Glerum et al. |
| 8,894,652 B2 | 11/2014 | Seifert et al. |
| 8,894,688 B2 | 11/2014 | Suh |
| 8,894,691 B2 | 11/2014 | Iott et al. |
| 8,906,069 B2 | 12/2014 | Hansell et al. |
| 8,964,934 B2 | 2/2015 | Ein-Gal |
| 8,992,580 B2 | 3/2015 | Bar et al. |
| 8,996,169 B2 | 3/2015 | Lightcap et al. |
| 9,001,963 B2 | 4/2015 | Sowards-Emmerd et al. |
| 9,002,076 B2 | 4/2015 | Khadem et al. |

(56) References Cited

U.S. PATENT DOCUMENTS

| | | |
|---|---|---|
| 9,044,190 B2 | 6/2015 | Rubner et al. |
| 9,107,683 B2 | 8/2015 | Hourtash et al. |
| 9,125,556 B2 | 9/2015 | Zehavi et al. |
| 9,131,986 B2 | 9/2015 | Greer et al. |
| 9,215,968 B2 | 12/2015 | Schostek et al. |
| 9,308,050 B2 | 4/2016 | Kostrzewski et al. |
| 9,380,984 B2 | 7/2016 | Li et al. |
| 9,393,039 B2 | 7/2016 | Lechner et al. |
| 9,398,886 B2 | 7/2016 | Gregerson et al. |
| 9,398,890 B2 | 7/2016 | Dong et al. |
| 9,414,859 B2 | 8/2016 | Ballard et al. |
| 9,420,975 B2 | 8/2016 | Gutfleisch et al. |
| 9,492,235 B2 | 11/2016 | Hourtash et al. |
| 9,592,096 B2 | 3/2017 | Maillet et al. |
| 9,750,465 B2 | 9/2017 | Engel et al. |
| 9,757,203 B2 | 9/2017 | Hourtash et al. |
| 9,795,354 B2 | 10/2017 | Menegaz et al. |
| 9,814,535 B2 | 11/2017 | Bar et al. |
| 9,820,783 B2 | 11/2017 | Donner et al. |
| 9,833,265 B2 | 11/2017 | Donner et al. |
| 9,848,922 B2 | 12/2017 | Tohmeh et al. |
| 9,925,011 B2 | 3/2018 | Gombert et al. |
| 9,931,025 B1 | 4/2018 | Graetzel et al. |
| 10,034,717 B2 | 7/2018 | Miller et al. |
| 2001/0036302 A1 | 11/2001 | Miller |
| 2002/0035321 A1 | 3/2002 | Bucholz et al. |
| 2004/0068172 A1 | 4/2004 | Nowinski et al. |
| 2004/0076259 A1 | 4/2004 | Jensen et al. |
| 2005/0096502 A1 | 5/2005 | Khalili |
| 2005/0143651 A1 | 6/2005 | Verard et al. |
| 2005/0171558 A1 | 8/2005 | Abovitz et al. |
| 2006/0100610 A1 | 5/2006 | Wallace et al. |
| 2006/0173329 A1 | 8/2006 | Marquart et al. |
| 2006/0184396 A1 | 8/2006 | Dennis et al. |
| 2006/0241416 A1 | 10/2006 | Marquart et al. |
| 2006/0291612 A1 | 12/2006 | Nishide et al. |
| 2007/0015987 A1 | 1/2007 | Benlloch Baviera et al. |
| 2007/0021738 A1 | 1/2007 | Hasser et al. |
| 2007/0038059 A1 | 2/2007 | Sheffer et al. |
| 2007/0073133 A1 | 3/2007 | Schoenefeld |
| 2007/0156121 A1 | 7/2007 | Millman et al. |
| 2007/0156157 A1 | 7/2007 | Nahum et al. |
| 2007/0167712 A1 | 7/2007 | Keglovich et al. |
| 2007/0233238 A1 | 10/2007 | Huynh et al. |
| 2008/0004523 A1 | 1/2008 | Jensen |
| 2008/0013809 A1 | 1/2008 | Zhu et al. |
| 2008/0033283 A1 | 2/2008 | Dellaca et al. |
| 2008/0046122 A1 | 2/2008 | Manzo et al. |
| 2008/0082109 A1 | 4/2008 | Moll et al. |
| 2008/0108912 A1 | 5/2008 | Node-Langlois |
| 2008/0108991 A1 | 5/2008 | von Jako |
| 2008/0109012 A1 | 5/2008 | Falco et al. |
| 2008/0144906 A1 | 6/2008 | Allred et al. |
| 2008/0161680 A1 | 7/2008 | von Jako et al. |
| 2008/0161682 A1 | 7/2008 | Kendrick et al. |
| 2008/0177203 A1 | 7/2008 | von Jako |
| 2008/0214922 A1 | 9/2008 | Hartmann et al. |
| 2008/0228068 A1 | 9/2008 | Viswanathan et al. |
| 2008/0228196 A1 | 9/2008 | Wang et al. |
| 2008/0235052 A1 | 9/2008 | Node-Langlois et al. |
| 2008/0269596 A1 | 10/2008 | Revie et al. |
| 2008/0287771 A1 | 11/2008 | Anderson |
| 2008/0287781 A1 | 11/2008 | Revie et al. |
| 2008/0300477 A1 | 12/2008 | Lloyd et al. |
| 2008/0300478 A1 | 12/2008 | Zuhars et al. |
| 2008/0302950 A1 | 12/2008 | Park et al. |
| 2008/0306490 A1 | 12/2008 | Lakin et al. |
| 2008/0319311 A1 | 12/2008 | Hamadeh |
| 2009/0012509 A1 | 1/2009 | Csavoy et al. |
| 2009/0030428 A1 | 1/2009 | Omori et al. |
| 2009/0080737 A1 | 3/2009 | Battle et al. |
| 2009/0185655 A1 | 7/2009 | Koken et al. |
| 2009/0198121 A1 | 8/2009 | Hoheisel |
| 2009/0216113 A1 | 8/2009 | Meier et al. |
| 2009/0228019 A1 | 9/2009 | Gross et al. |
| 2009/0259123 A1 | 10/2009 | Navab et al. |
| 2009/0259230 A1 | 10/2009 | Khadem et al. |
| 2009/0264899 A1 | 10/2009 | Appenrodt et al. |
| 2009/0281417 A1 | 11/2009 | Hartmann et al. |
| 2010/0022874 A1 | 1/2010 | Wang et al. |
| 2010/0039506 A1 | 2/2010 | Sarvestani et al. |
| 2010/0125286 A1 | 5/2010 | Wang et al. |
| 2010/0130986 A1 | 5/2010 | Mailloux et al. |
| 2010/0228117 A1 | 9/2010 | Hartmann |
| 2010/0228265 A1 | 9/2010 | Prisco |
| 2010/0249571 A1 | 9/2010 | Jensen et al. |
| 2010/0274120 A1 | 10/2010 | Heuscher |
| 2010/0280363 A1 | 11/2010 | Skarda et al. |
| 2010/0331858 A1 | 12/2010 | Simaan et al. |
| 2011/0022229 A1 | 1/2011 | Jang et al. |
| 2011/0077504 A1 | 3/2011 | Fischer et al. |
| 2011/0098553 A1 | 4/2011 | Robbins et al. |
| 2011/0137152 A1 | 6/2011 | Li |
| 2011/0152676 A1* | 6/2011 | Groszmann .......... A61B 6/12 |
| | | 600/426 |
| 2011/0213384 A1 | 9/2011 | Jeong |
| 2011/0224684 A1 | 9/2011 | Larkin et al. |
| 2011/0224685 A1 | 9/2011 | Larkin et al. |
| 2011/0224686 A1 | 9/2011 | Larkin et al. |
| 2011/0224687 A1 | 9/2011 | Larkin et al. |
| 2011/0224688 A1 | 9/2011 | Larkin et al. |
| 2011/0224689 A1 | 9/2011 | Larkin et al. |
| 2011/0224825 A1 | 9/2011 | Larkin et al. |
| 2011/0230967 A1 | 9/2011 | O'Halloran et al. |
| 2011/0238080 A1 | 9/2011 | Ranjit et al. |
| 2011/0276058 A1 | 11/2011 | Choi et al. |
| 2011/0282189 A1 | 11/2011 | Graumann |
| 2011/0286573 A1 | 11/2011 | Schretter et al. |
| 2011/0295062 A1 | 12/2011 | Gratacos Solsona et al. |
| 2011/0295370 A1 | 12/2011 | Suh et al. |
| 2011/0306986 A1 | 12/2011 | Lee et al. |
| 2012/0035507 A1 | 2/2012 | George et al. |
| 2012/0046668 A1 | 2/2012 | Gantes |
| 2012/0051498 A1 | 3/2012 | Koishi |
| 2012/0053597 A1 | 3/2012 | Anvari et al. |
| 2012/0059248 A1 | 3/2012 | Holsing et al. |
| 2012/0071753 A1 | 3/2012 | Hunter et al. |
| 2012/0108954 A1 | 5/2012 | Schulhauser et al. |
| 2012/0136372 A1 | 5/2012 | Amat Girbau et al. |
| 2012/0143084 A1 | 6/2012 | Shoham |
| 2012/0184839 A1 | 7/2012 | Woerlein |
| 2012/0197182 A1 | 8/2012 | Millman et al. |
| 2012/0226145 A1 | 9/2012 | Chang et al. |
| 2012/0235909 A1 | 9/2012 | Birkenbach et al. |
| 2012/0245596 A1 | 9/2012 | Meenink |
| 2012/0253332 A1 | 10/2012 | Moll |
| 2012/0253360 A1 | 10/2012 | White et al. |
| 2012/0256092 A1 | 10/2012 | Zingerman |
| 2012/0294498 A1 | 11/2012 | Popovic |
| 2012/0296203 A1 | 11/2012 | Hartmann et al. |
| 2013/0006267 A1 | 1/2013 | Odermatt et al. |
| 2013/0016889 A1 | 1/2013 | Myronenko et al. |
| 2013/0027433 A1* | 1/2013 | Hand .................. G06F 3/04883 |
| | | 345/650 |
| 2013/0030571 A1 | 1/2013 | Ruiz Morales et al. |
| 2013/0035583 A1 | 2/2013 | Park et al. |
| 2013/0060146 A1 | 3/2013 | Yang et al. |
| 2013/0060337 A1 | 3/2013 | Petersheim et al. |
| 2013/0094742 A1 | 4/2013 | Feilkas |
| 2013/0096574 A1 | 4/2013 | Kang et al. |
| 2013/0113791 A1 | 5/2013 | Isaacs et al. |
| 2013/0116706 A1 | 5/2013 | Lee et al. |
| 2013/0131695 A1 | 5/2013 | Scarfogliero et al. |
| 2013/0135312 A1 | 5/2013 | Yang et al. |
| 2013/0144307 A1 | 6/2013 | Jeong et al. |
| 2013/0158542 A1 | 6/2013 | Manzo et al. |
| 2013/0165937 A1 | 6/2013 | Patwardhan |
| 2013/0178867 A1 | 7/2013 | Farritor et al. |
| 2013/0178868 A1 | 7/2013 | Roh |
| 2013/0178870 A1 | 7/2013 | Schena |
| 2013/0204271 A1 | 8/2013 | Brisson et al. |
| 2013/0211419 A1 | 8/2013 | Jensen |
| 2013/0211420 A1 | 8/2013 | Jensen |
| 2013/0218142 A1 | 8/2013 | Tuma et al. |

(56) References Cited

U.S. PATENT DOCUMENTS

| | | |
|---|---|---|
| 2013/0223702 A1 | 8/2013 | Holsing et al. |
| 2013/0225942 A1 | 8/2013 | Holsing et al. |
| 2013/0225943 A1 | 8/2013 | Holsing et al. |
| 2013/0231556 A1 | 9/2013 | Holsing et al. |
| 2013/0237995 A1 | 9/2013 | Lee et al. |
| 2013/0245375 A1 | 9/2013 | DiMaio et al. |
| 2013/0261640 A1 | 10/2013 | Kim et al. |
| 2013/0272488 A1 | 10/2013 | Bailey et al. |
| 2013/0272489 A1 | 10/2013 | Dickman et al. |
| 2013/0274761 A1 | 10/2013 | Devengenzo et al. |
| 2013/0281821 A1 | 10/2013 | Liu et al. |
| 2013/0296884 A1 | 11/2013 | Taylor et al. |
| 2013/0303887 A1 | 11/2013 | Holsing et al. |
| 2013/0307955 A1 | 11/2013 | Deitz et al. |
| 2013/0317521 A1 | 11/2013 | Choi et al. |
| 2013/0325033 A1 | 12/2013 | Schena et al. |
| 2013/0325035 A1 | 12/2013 | Hauck et al. |
| 2013/0331686 A1 | 12/2013 | Freysinger et al. |
| 2013/0331858 A1 | 12/2013 | Devengenzo et al. |
| 2013/0331861 A1 | 12/2013 | Yoon |
| 2013/0342578 A1 | 12/2013 | Isaacs |
| 2013/0345717 A1 | 12/2013 | Markvicka et al. |
| 2013/0345718 A1* | 12/2013 | Crawford ............ A61B 17/025 606/130 |
| 2013/0345757 A1 | 12/2013 | Stad |
| 2014/0001235 A1 | 1/2014 | Shelton, IV |
| 2014/0012131 A1 | 1/2014 | Heruth et al. |
| 2014/0031664 A1 | 1/2014 | Kang et al. |
| 2014/0046128 A1 | 2/2014 | Lee et al. |
| 2014/0046132 A1 | 2/2014 | Hoeg et al. |
| 2014/0046340 A1 | 2/2014 | Wilson et al. |
| 2014/0049629 A1 | 2/2014 | Siewerdsen et al. |
| 2014/0058406 A1 | 2/2014 | Tsekos |
| 2014/0073914 A1 | 3/2014 | Lavallee et al. |
| 2014/0080086 A1 | 3/2014 | Chen |
| 2014/0081128 A1 | 3/2014 | Verard et al. |
| 2014/0088612 A1 | 3/2014 | Bartol et al. |
| 2014/0094694 A1 | 4/2014 | Moctezuma de la Barrera |
| 2014/0094851 A1 | 4/2014 | Gordon |
| 2014/0096369 A1 | 4/2014 | Matsumoto et al. |
| 2014/0100587 A1 | 4/2014 | Farritor et al. |
| 2014/0121676 A1 | 5/2014 | Kostrzewski et al. |
| 2014/0128882 A1 | 5/2014 | Kwak et al. |
| 2014/0135796 A1 | 5/2014 | Simon et al. |
| 2014/0142591 A1 | 5/2014 | Alvarez et al. |
| 2014/0142592 A1 | 5/2014 | Moon et al. |
| 2014/0148692 A1 | 5/2014 | Hartmann et al. |
| 2014/0163581 A1 | 6/2014 | Devengenzo et al. |
| 2014/0171781 A1 | 6/2014 | Stiles |
| 2014/0171900 A1 | 6/2014 | Stiles |
| 2014/0171965 A1 | 6/2014 | Loh et al. |
| 2014/0180308 A1 | 6/2014 | von Grunberg |
| 2014/0180309 A1 | 6/2014 | Seeber et al. |
| 2014/0187915 A1 | 7/2014 | Yaroshenko et al. |
| 2014/0188132 A1 | 7/2014 | Kang |
| 2014/0194699 A1 | 7/2014 | Roh et al. |
| 2014/0130810 A1 | 8/2014 | Azizian et al. |
| 2014/0221819 A1 | 8/2014 | Sarment |
| 2014/0222023 A1 | 8/2014 | Kim et al. |
| 2014/0228631 A1 | 8/2014 | Kwak et al. |
| 2014/0234804 A1 | 8/2014 | Huang et al. |
| 2014/0257328 A1 | 9/2014 | Kim et al. |
| 2014/0257329 A1 | 9/2014 | Jang et al. |
| 2014/0257330 A1 | 9/2014 | Choi et al. |
| 2014/0275760 A1 | 9/2014 | Lee et al. |
| 2014/0275985 A1 | 9/2014 | Walker et al. |
| 2014/0276931 A1 | 9/2014 | Parihar et al. |
| 2014/0276940 A1 | 9/2014 | Seo |
| 2014/0276944 A1 | 9/2014 | Farritor et al. |
| 2014/0288413 A1 | 9/2014 | Hwang et al. |
| 2014/0299648 A1 | 10/2014 | Shelton, IV et al. |
| 2014/0303434 A1 | 10/2014 | Farritor et al. |
| 2014/0303643 A1 | 10/2014 | Ha et al. |
| 2014/0305995 A1 | 10/2014 | Shelton, IV et al. |
| 2014/0309659 A1 | 10/2014 | Roh et al. |
| 2014/0316436 A1 | 10/2014 | Bar et al. |
| 2014/0323803 A1 | 10/2014 | Hoffman et al. |
| 2014/0324070 A1 | 10/2014 | Min et al. |
| 2014/0330288 A1 | 11/2014 | Date et al. |
| 2014/0364720 A1 | 12/2014 | Darrow et al. |
| 2014/0371577 A1 | 12/2014 | Maillet et al. |
| 2015/0039034 A1 | 2/2015 | Frankel et al. |
| 2015/0085970 A1 | 3/2015 | Bouhnik et al. |
| 2015/0146847 A1 | 5/2015 | Liu |
| 2015/0150524 A1 | 6/2015 | Yorkston et al. |
| 2015/0196261 A1 | 7/2015 | Funk |
| 2015/0213633 A1 | 7/2015 | Chang et al. |
| 2015/0324114 A1 | 11/2015 | Hurley et al. |
| 2015/0335480 A1 | 11/2015 | Alvarez et al. |
| 2015/0342647 A1 | 12/2015 | Frankel et al. |
| 2016/0005194 A1 | 1/2016 | Schretter et al. |
| 2016/0166329 A1 | 6/2016 | Langan et al. |
| 2016/0235480 A1 | 8/2016 | Scholl et al. |
| 2016/0249990 A1 | 9/2016 | Glozman et al. |
| 2016/0302871 A1 | 10/2016 | Gregerson et al. |
| 2016/0320322 A1 | 11/2016 | Suzuki |
| 2016/0331335 A1 | 11/2016 | Gregerson et al. |
| 2017/0135770 A1 | 5/2017 | Scholl et al. |
| 2017/0143284 A1 | 5/2017 | Sehnert et al. |
| 2017/0143426 A1 | 5/2017 | Isaacs et al. |
| 2017/0156816 A1 | 6/2017 | Ibrahim |
| 2017/0202629 A1 | 7/2017 | Maillet et al. |
| 2017/0212723 A1 | 7/2017 | Atarot et al. |
| 2017/0215825 A1 | 8/2017 | Johnson et al. |
| 2017/0215826 A1 | 8/2017 | Johnson et al. |
| 2017/0215827 A1 | 8/2017 | Johnson et al. |
| 2017/0231710 A1 | 8/2017 | Scholl et al. |
| 2017/0258426 A1 | 9/2017 | Risher-Kelly et al. |
| 2017/0273748 A1 | 9/2017 | Hourtash et al. |
| 2017/0296277 A1 | 10/2017 | Hourtash et al. |
| 2017/0360493 A1 | 12/2017 | Zucker et al. |

* cited by examiner

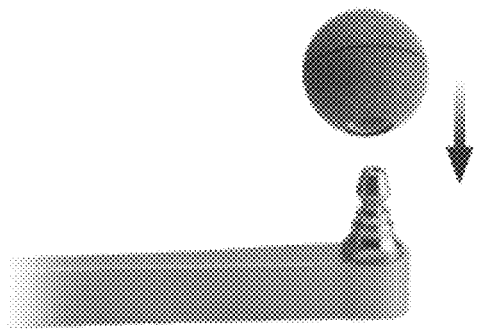
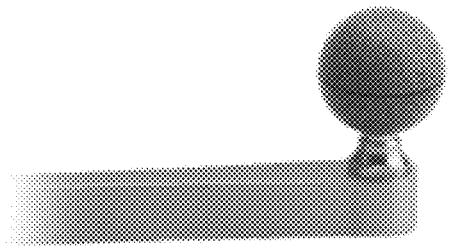
Figure 46(a)　　　　　　Figure 46(b)
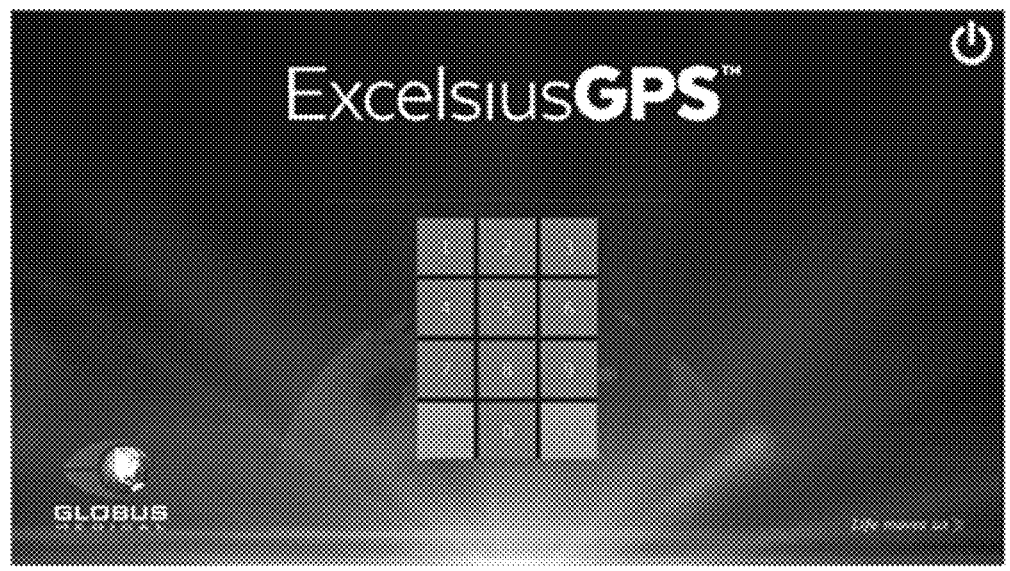
Figure 47

ROBOT SURGICAL PLATFORM

CROSS REFERENCE TO RELATED APPLICATIONS

This application claims priority under 35 U.S.C. 119(e) to U.S. Provisional Patent Application Ser. No. 62/535,591, filed Jul. 21, 2017, the content of which is incorporated by reference herein in its entirety for all purposes.

TECHNICAL FIELD

The present disclosure relates to medical devices, and more particularly, robotic surgical systems and related methods and devices.

BACKGROUND

Various medical procedures require the precise localization of a three-dimensional position of a surgical instrument within the body of a patient in order to effect optimized treatment. For example, some surgical procedures to fuse vertebrae require that a surgeon drill multiple holes into the bone structure at specific locations. To achieve high levels of mechanical integrity in the fusing system, and to balance the forces created in the bone structure, it is necessary that the holes are drilled precisely at desired locations. Vertebrae, like most bone structures, have complex shapes made up of non-planar curved surfaces making precise and perpendicular drilling difficult. Conventionally, a surgeon manually holds and positions a drill guide tube by using a guidance system to overlay the drill tube's position onto a three dimensional image of the bone structure. This manual process is both tedious and time consuming. The success of the surgery is largely dependent upon the dexterity of the surgeon who performs it.

Robot surgical platforms are being introduced that can assist surgeons with positioning surgical tools and performing surgical procedures within a patient body. A robot surgical platform can include a robot that is coupled to an end-effector element, and where the robot is configured to control movement and positioning of the end-effector relative to the body. The end-effector may be a surgical tool guide tube, such as a drill guide tube, or may be the surgical tool itself.

There is a need for a robot surgical platform that provides accurate localization of a three-dimensional position of a surgical tool relative to the body in order to effect optimized treatment. Improved localization accuracy can minimize human and robotic error while allowing fast and efficient surgical process. The ability to perform operations on a patient with a robot surgical platform and computer software can enhance the overall surgical procedure and the results achieved for the patient.

SUMMARY

Some embodiments of the present disclosure are directed to a surgical implant planning computer that can be used for intra-operative computed tomography (CT) imaging workflow. The surgical implant planning computer includes at least one network interface, a display device, at least one processor, and at least one memory. The at least one network interface is connectable to a CT image scanner and to a robot having a robot base coupled to a robot arm that is movable by motors relative to the robot base. The at least one memory stores program code that is executed by the at least one processor to perform operations that include displaying on the display device a CT image of a bone that is received from the CT image scanner through the at least one network interface and receiving a user's selection of a surgical screw from among a set of defined surgical screws. The operations further include displaying a graphical screw representing the selected surgical screw as an overlay on the CT image of the bone and controlling angular orientation and location of the displayed graphical screw relative to the bone in the CT image responsive to receipt of user inputs. An indication of the selected surgical screw and an angular orientation and a location of the displayed graphical screw are stored in a surgical plan data structure responsive to receipt of a defined user input.

Some other embodiments of the present disclosure are directed to a surgical implant planning computer that can be used for pre-operative CT imaging workflow. The surgical implant planning computer includes at least one network interface, a display device, at least one processor, and at least one memory. The at least one network interface is connectable to an image database. The at least one memory stores program code that is executed by the at least one processor to perform operations that include loading a CT image of a bone, which is received from the image database through the at least one network interface, into the at least one memory. The operations display displaying the CT image on the display device. The operations receive a user's selection of a surgical screw from among a set of defined surgical screws, and display a graphical screw representing the selected surgical screw as an overlay on the CT image of the bone. The operations control angular orientation and location of the displayed graphical screw relative to the bone in the CT image responsive to receipt of user inputs, and store an indication of the selected surgical screw and an angular orientation and a location of the displayed graphical screw in a surgical plan data structure responsive to user input, the surgical plan data structure being configured for use by a robot with a robot base coupled to a robot arm that is movable by motors relative to the robot base.

Some other embodiments of the present disclosure are directed to a surgical implant planning computer that can be used for fluoroscopic imaging workflow. The surgical implant planning computer includes at least one network interface, a display device, at least one processor, and at least one memory. The at least one network interface is connectable to a fluoroscopy imager, a marker tracking camera, and a robot having a robot base that is coupled to a robot arm which movable by motors relative to the robot base. The at least one memory stores program code that is executed by the at least one processor to perform operations that include performing a registration setup mode that includes determining occurrence of a first condition indicating the marker tracking camera can observe to track reflective markers that are attached to a fluoroscopy registration fixture of a fluoroscopy imager, and determining occurrence of a second condition indicating the marker tracking camera can observe to track dynamic reference base markers attached to the robot arm and/or an end-effector connected to the robot arm. While both of the first and second conditions are determined to continue to occur, the at least one processor allows operations to be performed to obtain a first intra-operative fluoroscopic image of a patient along a first plane and to obtain a second intra-operative fluoroscopic image of the patient along a second plane that is orthogonal to the first plane.

Corresponding methods and computer program products are disclosed.

Still other surgical implant landing computers, methods, and computer program products according to embodiments of the inventive subject matter will be or become apparent to one with skill in the art upon review of the following drawings and detailed description. It is intended that all such surgical implant landing computers, methods, and computer program products be included within this description, be within the scope of the present inventive subject matter, and be protected by the accompanying claims. Moreover, it is intended that all embodiments disclosed herein can be implemented separately or combined in any way and/or combination.

DESCRIPTION OF THE DRAWINGS

The accompanying drawings, which are included to provide a further understanding of the disclosure and are incorporated in a constitute a part of this application, illustrate certain non-limiting embodiments of inventive concepts. In the drawings:

FIG. 15(a) illustrates how the outer cannula is positioned above the incision. FIG. 15(b) illustrates how the cannulas is placed into the guide tube such that it rests on skin. FIG. 15(c) illustrates how the first inner cannula is inserted into the incision. FIG. 15(d) illustrates how the second inner cannula is then inserted into the incision. FIG. 15(e) illustrates how the outer cannula is then inserted into the incision. FIG. 15(f) illustrates both inner cannulas then being removed and lowering the guide tube until it sits within the outer cannula.

FIG. 22(a) illustrates positioning a quattro spike over a guide post. FIG. 22(b) illustrates attaching an impaction cap. FIG. 22(c) illustrates inserting an assembly into a rigid anatomy. FIG. 22(d) illustrates removing a cap and guide pose.

FIG. 31(a) illustrates pulling up on the release handle located on a camera stand. FIG. 31(b) illustrates clearing the legs of a camera stand legs automatically releasing and moving outward.

FIGS. 46(a) and 46(b) illustrate attaching a reflective marker to one of a plurality of marker posts of the instrument assembly. FIG. 46(a) illustrates lowering the reflective marker onto a marker post. FIG. 46(b) illustrates a marker fully seated on the post.

FIG. 47 illustrates a login screen displayed on a monitor.

DETAILED DESCRIPTION

Figure 1:
FIG. 1 illustrates a robotic system that includes a robotic base station and a camera stand.

The following discussion is presented to enable a person skilled in the art to make and use embodiments of the present disclosure. Various modifications to the illustrated embodiments will be readily apparent to those skilled in the art, and the principles herein can be applied to other embodiments and applications without departing from embodiments of the present disclosure. Thus, the embodiments are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the embodiments. Skilled artisans will recognize the examples provided herein have many useful alternatives and fall within the scope of the embodiments.

System Overview

The robotic computer system enables real-time surgical navigation using radiological patient images and guides the trajectory of specialized surgical instruments along a surgeon-specified path using a robotic arm. The system software reformats patient-specific CT images acquired before surgery, or fluoroscopic images acquired during surgery, and displays them on screen from a variety of views. Prior to operating, the surgeon may then create, store, access, and simulate trajectories. During surgery, the system guides the instruments to follow the trajectory specified by the user, and tracks the position of surgical instruments in or on the patient anatomy and continuously updates the instrument position on these images. The surgery is performed by the surgeon, using the specialized surgical instruments.

The software can also show how the actual position and path during surgery relate to the pre-surgical plan, and can help guide the surgeon along the planned trajectory. While the surgeon's judgment remains the ultimate authority, real-time positional and trajectory information obtained through the robotic computer system can serve to validate this judgment. An example robotic computer system that could be used with embodiments herein is the ExcelsiusGPS™ by Globus Medical.

Device Description

The robotic computer system is a Robotic Positioning System that includes a computer controlled robotic arm, hardware, and software that enables real time surgical navigation and robotic guidance using radiological patient images (pre-operative CT, intra-operative CT and fluoroscopy), using a dynamic reference base and positioning camera. The navigation and guidance system determines the registration or mapping between the virtual patient (points on the patient images) and the physical patient (corresponding points on the patient's anatomy). Once this registration is created, the software displays the relative position of a tracked instrument, including the end-effector of the robotic arm, on the patient images. This visualization can help guide the surgeon's planning and approach. As an aid to visualization, the surgeon can plan implant placement on the patient images prior to surgery. The information of the plan coupled with the registration provides the necessary information to provide visual assistance to the surgeon during free hand navigation or during automatic robotic alignment of the end-effector.

During surgery, the system tracks the position of GPS compatible instruments, including the end-effector of the robotic arm, in or on the patient anatomy and continuously updates the instrument position on patient images utilizing optical tracking. Standard non-navigated metallic instruments that fit through the guide tube at the selected trajectory may be used without navigation while the guide tube is stationary, for uses such as bone preparation (e.g. rongeurs, reamers etc.) or placing MIS implants (e.g. rod inserters, locking cap drivers) that are not related to screw placement. Navigation can also be performed without guidance. System software is responsible for all motion control functions, navigation functions, data storage, network connectivity, user management, case management, and safety functions, robotic computer system surgical instruments are non-sterile, re-usable instruments that can be operated manually or with the use of the positioning system.

Robotic computer system instruments include registration instruments, patient reference instruments, surgical instruments, and end-effectors. Registration instruments incorporate arrays of reflective markers, and are used to track patient anatomy and surgical instruments and implants; components include the verification probe, surveillance marker, surgical instrument arrays, intra-op CT registration fixture, fluoroscopy registration fixture, and dynamic reference base (DRB). Patient reference instruments are either clamped or driven into any appropriate rigid anatomy that is considered safe and provides a point of rigid fixation for the DRB. Surgical instruments are used to prepare the implant site or implant the device, and include awls, drills, drivers, taps, and probes. End-effectors can be wirelessly powered guide tubes that attach to the distal end of the robotic arm and provide a rigid structure for insertion of surgical instruments.

Indications for Use

The robotic computer system is intended for use as an aid for precisely locating anatomical structures and for the spatial positioning and orientation of instrument holders or tool guides to be used by surgeons for navigating or guiding standard surgical instruments in open or percutaneous procedures. The system is indicated for any medical condition in which the use of stereotactic surgery may be appropriate, and where reference to a rigid anatomical structure, such as the skull, a long bone, or vertebra can be identified relative to a CT-based model, fluoroscopy images, or digitized landmarks of the anatomy.

Contraindications

Medical conditions which contraindicate the use of the robotic computer system and its associated applications include any medical conditions which may contraindicate the medical procedure itself.

Navigation Integrity

The robotic computer system has built-in precautions to support navigation integrity but additional steps should be taken to verify the accuracy of the system during navigation. Specific steps include:

Ensure the stabilizers have been engaged prior to using the robotic arm.

Do not move the dynamic reference base after successful registration.

Use a surveillance marker with every procedure to further confirm the accuracy of the images in relation to real-time patient anatomy.

If a surveillance marker alerts movement of patient relative to the dynamic reference base, perform a landmark check. If a landmark check fails, re-register the patient.

Use a verified navigation instrument to perform an anatomical landmark check prior to a procedure. If a landmark check fails, re-register the patient.

Compliance with Standards

This product conforms to the requirements of council directive 93/42/EEC concerning medical devices, when it bears the CE Mark of Conformity shown below, shown at right.

This product conforms to the requirements of standards listed below when it bears the following NRTL Certification Compliance Mark, shown at right.

Electric and electromagnetic testing have been performed in accordance with the following applicable standards: ANSI/AAMI ES60601-1, CSA C22.2 #60601-1, CISPR 11, IEC 60601-1 (including all national deviations), IEC 60601-1-2, IEC 60601-1-6, IEC 60601-1-9, IEC 60601-2-49 (only portions of this standard are used to demonstrate compliance and proper operation of the robotic computer system when used with high frequency surgical equipment such as a cauterizer), IEC 60825-1, IEC 62304, IEC 62366.

HF Surgical Equipment

Based on the robotic computer system floating applied part (type BF) and the safety testing performed, the system is compatible with the use of HF surgical equipment with no restrictions on the conditions of use.

EMC Compliance

In accordance with IEC 60601-1-2:2014 Edition 3 and 4, Medical Electrical Equipment needs special precautions regarding Electro Magnetic Compatibility (EMC) and needs to be installed and put into service according to the EMC information provided in the tables below. Portable and mobile RF communications equipment can adversely affect electrical medical equipment. The tables supply details about the level of compliance and provide information about potential interactions between devices. EMC Compliance tables from 3rd Edition are shown on the next page with values adjusted for 4th Edition where appropriate.

The robotic computer system has an optional 802.11 g/b/n wireless router and tablet option. When installed, this transmits RF power at 2.4 GHz (2.412-2.484 GHz) using DSSS or OFDM with DQPSK or QAM modulation. Maximum RF transmit power is 100 mW.

| Recommended separation distances | | | |
|---|---|---|---|
| | Separation distance according to frequency of transmitter (m) | | |
| Rated maximum output power of transmitter (W) | 150 kHz to 80 MHz $d = 1.2\sqrt{P}$ | 80 MHz to 800 MHz $d = 1.2\sqrt{P}$ | 800 MHz to 2.5 GHz $d = 2.3\sqrt{P}$ |
| 0.01 | 0.3* | 0.3* | 0.3* |
| 0.1 | 0.37 | 0.37 | 0.74 |
| 1 | 1.17 | 1.17 | 2.33 |
| 10 | 3.69 | 3.69 | 7.38 |
| 100 | 11.67 | 11.67 | 23.33 |

*30 cm is the minimum recommended separation distance even though the calculation would yield a shorter distance.
For transmitters rated at a maximum output power not listed above, the recommended separation distance in meters (m) can be estimated using the equation applicable to the frequency of the transmitter, where P is the maximum output power rating of the transmitter in watts (W) according to the transmitter manufacturer.
NOTE 1:
At 80 MHz and 800 MHz, the separation distance for the higher frequency range applies.
NOTE 2:
These guidelines may not apply in all situations. Electromagnetic propagation is affected by absorption and reflection from structures, objects and people.

Cybersecurity

The robotic computer system adheres to industry best practices and FDA guidance on cybersecurity in medical devices. This includes firewall protection and additional protection against virus, malware, data corruption, and unauthorized system access.

System Overview

The robotic computer system consists of four main components: Robotic Base Station (shown below), Camera Stand (shown below), Instruments, and System Software. FIG. 1 illustrates a robotic system that includes a robotic base station and a camera stand.

Robotic Base Station

Figure 2:
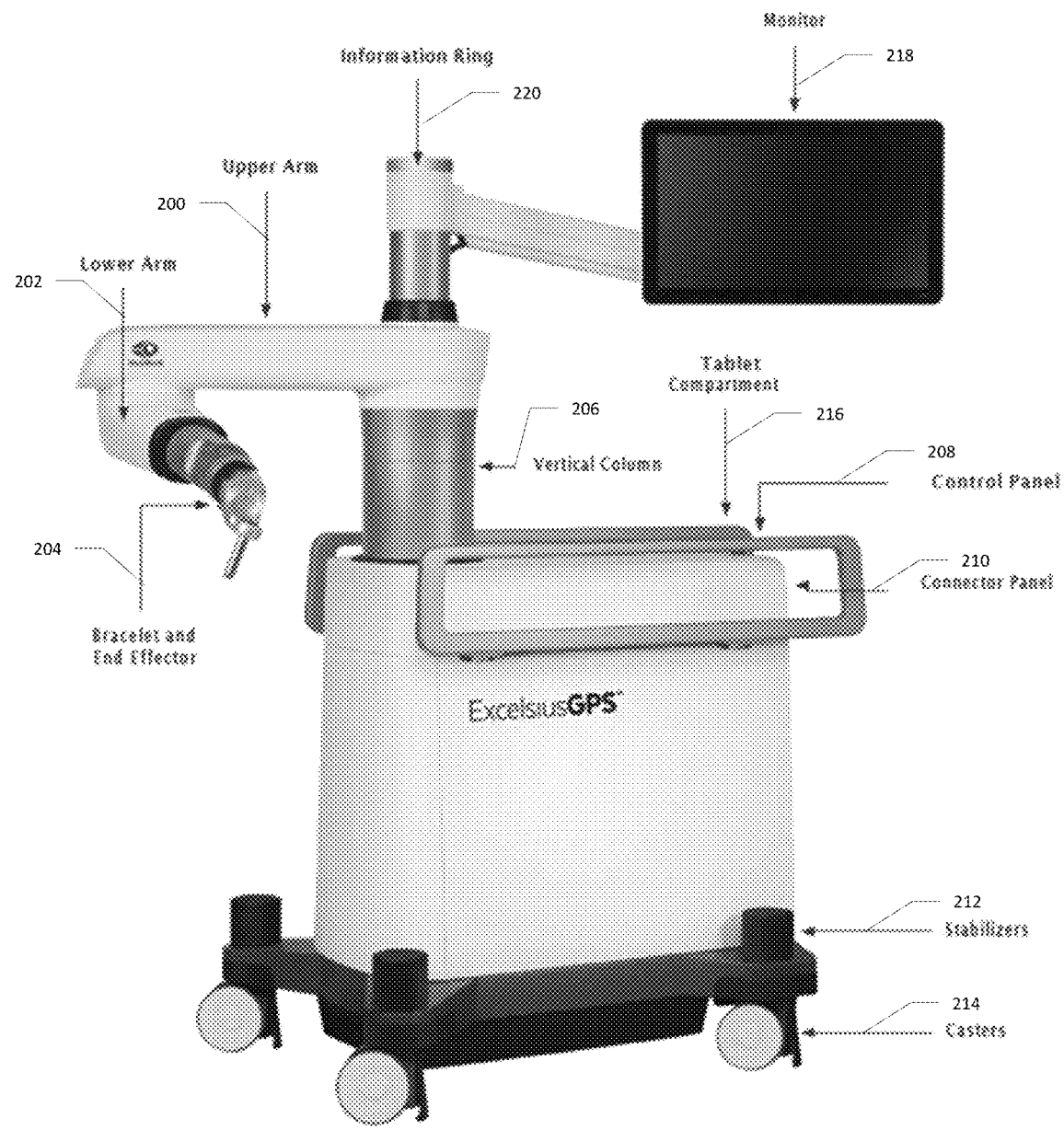
FIG. 2 illustrates components of a robotic base station.

The Robotic Base Station is the main control center for the robotic computer system and includes the components shown below. FIG. 2 illustrates Components of the Robotic Base station. The robotic base station includes a vertical column 206 that supports an upper arm 200 connected to a lower arm 202, with a bracelet and end effector 204 connected to the lower arm 202. An information ring 220 on the vertical column 206 is illuminated to provide information as described below. A monitor 218 is connected to the vertical column 206. The robotic base station also includes a tablet compartment 216, a control panel 208, a connector panel 210, stabilizers 212, and rolling casters 214.

Monitor

Figure 3:
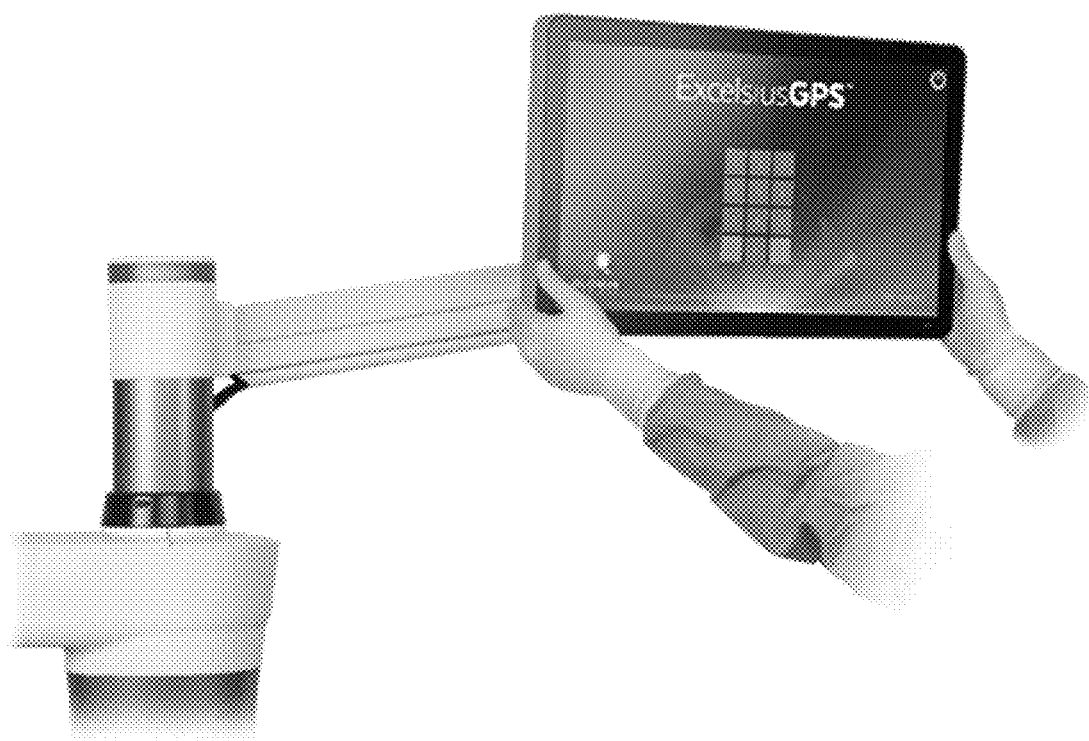
FIG. 3 illustrates the monitor of the robotic base station.

The monitor allows the surgeon to plan the surgery and visualize anatomical structures, instruments, and implants in real time. It is a high resolution, flat panel touch screen liquid crystal display (LCD) located on the vertical column. The monitor can be adjusted to the desired location with two hands. An external mouse is available for optional use with the monitor. The mouse is not intended for use within the sterile field. FIG. 3 illustrates the monitor of the robotic base station.

Tablet

An optional wireless tablet is available for use as a second touchscreen monitor for operative planning and software control. The main monitor remains active at all times during use. The user can lockout tablet use if desired. The tablet compartment is used to store the tablet. The tablet is not intended for use within the sterile field.

Control Panel

Figure 4:
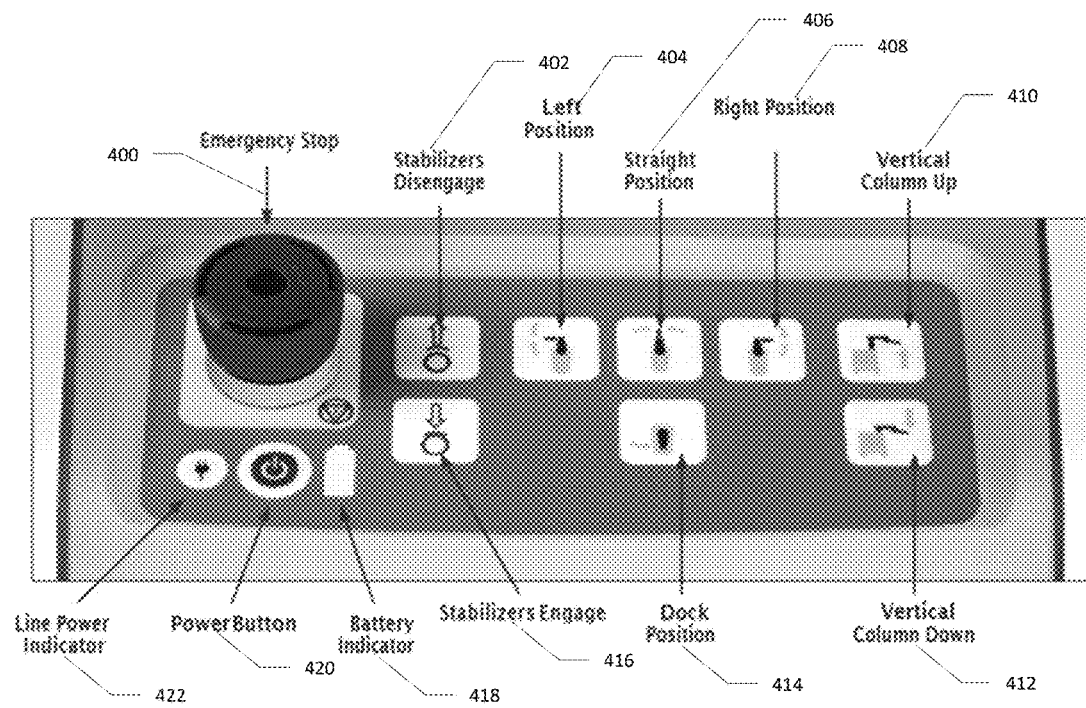
FIG. 4 illustrates the control panel on the rear of the robotic base station and the control panel functions.

The control panel is located at the rear of the Robotic Base Station. This panel is used to display and control system power and general positioning functions. FIG. 4 illustrates the control panel on the rear of the Robotic Base Station and the control panel functions. The control panel includes: emergency stop button 400, stabilizers disengage button 402, a left position button 404, a straight position button 406, a right position button 408, a vertical column up button 410, a vertical column down button 412, a dock position button 414, a stabilizers engage button 416, a battery status indicator 418, a power button 420, and a line power indicator 422.

Connector Panel

Figure 5:
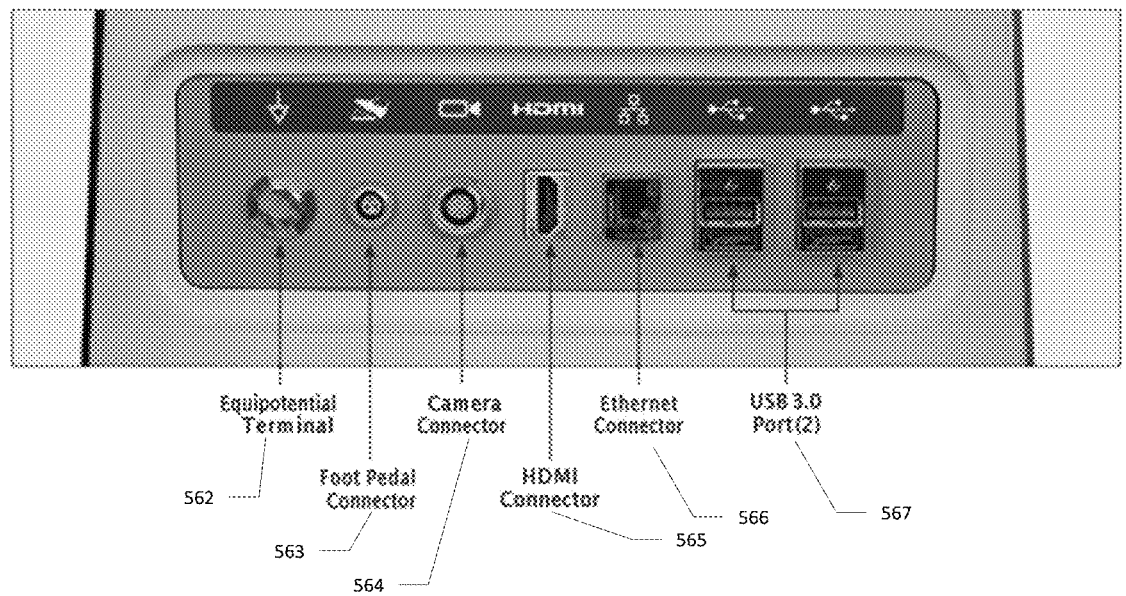
FIG. 5 illustrates the connector panel located at the rear of the robotic base station.

The connector panel is located at the rear of the Robotic Base Station. This panel contains external connection ports for various devices. FIG. 5 illustrates the connector panel located at the rear of the Robotic Base Station. The connector panel includes: an equipotential terminal 562, a foot pedal connector 563, a camera connector port 564, an HDMI connector 565, an ethernet connector 566, and dual USB 3.0 ports 567.

| Connector panel functions | |
|---|---|
| Item | Function |
| Equipotential Terminal | Used to connect to other auxiliary equipment; used by service personnel |
| Foot Pedal Connector | Connects to the foot pedal cable |
| Camera Connector | Connects to the camera stand cable |
| HDMI Connector | Connects to an external monitor |
| Ethernet Connector | Connects to a network or intra-operative imaging system for image transfer |
| USB Port 3.0 | Connects to a USB device for image transfer Connects to C-Arm via video capture supplied with the Fluoroscopy Registration Fixture |

Casters and Stabilizers

The system consists of four casters with integrated stabilizers. The stabilizers are used to immobilize the system to ensure that it does not move during use.

Upper Arm, Lower Arm, and Vertical Column

The robotic arm, which consists of an upper and lower arm, is attached to the vertical column of the robotic computer system Robotic Base Station. This configuration allows for a wide range of motion.

The robotic computer system employs a state of the art drive control system along with high performance servo drives to accurately position and control the 5-axis robotic

Figure 6:
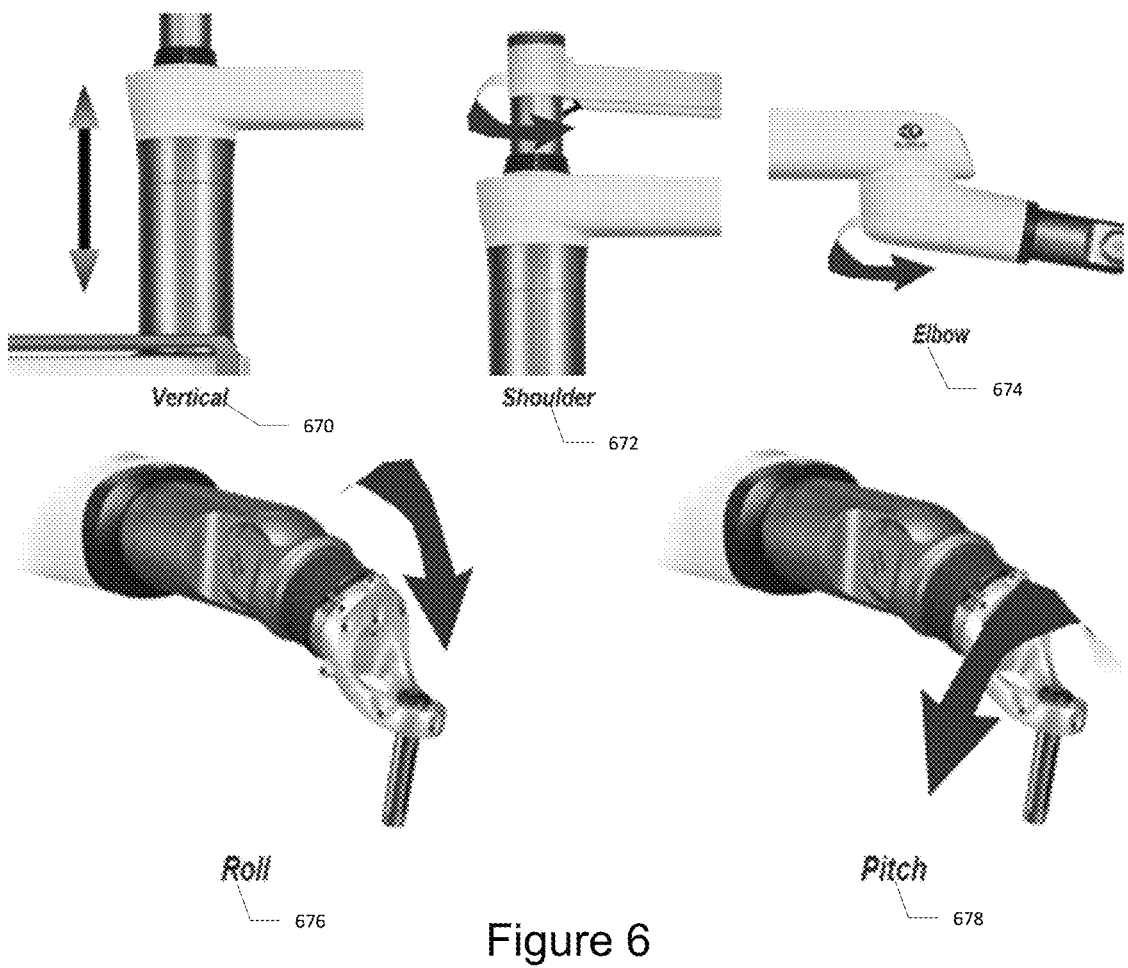
FIG. 6 illustrates the 5-axis robotic arm.

| Control panel functions | | |
|---|---|---|
| Button | Function | To Use |
| Emergency Stop | Removes power from motors and applies brake | Press down to activate. To deactivate and re-power, twist knob counterclockwise. |
| Line Power Indicator | Illuminates when system is plugged into AC power outlet | Press to turn ON/OFF |
| Power Button | Powers the Robotic Base Station ON/OFF. Illuminated when ON. | Press to turn ON/OFF |
| Battery Indicator | Indicates level and state of charge All bars are illuminated when fully charged When operating on battery, number of illuminated bars indicates percent of charge Bars progressively illuminate when charging | |
| Stabilizers Disengage | Illuminates when system is free to move | Press to disengage the stabilizers to allow movement of the system |
| Stabilizers Engage | Illuminates when system is secured to floor | Press to engage the stabilizers, to lock the system in place |
| Left Position | Moves upper arm forward and lower arm at a 90° angle to the left | Press and hold button. Operator may release button prior to final position and arm will stop in current position. |
| Right Position | Moves upper arm forward and lower arm at a 90° angle to the right. | |
| Straight Position | Moves upper and lower arm forward | Stop in current position |
| Dock Position | Moves upper and lower arm to rest over the cabinet | |
| Vertical Column Up | Moves vertical column up | Press and hold button. Operator should release button once the desired height is reached. |
| Vertical Column Down | Moves vertical column down | | arm in an operating room environment. FIG. 6 illustrates the 5-axis robotic arm. The 5 axes of motion are identified below.

| Axis | Travel Distance |
| --- | --- |
| Vertical 670 | ≥480 mm |
| Shoulder 672 | −150° to 180° |
| Elbow 674 | −150° to 150° |
| Roll 676 | −135° to 135° |
| Pitch 678 | −70° to 70° |

Bracelet

The bracelet is located at the distal end of the lower arm. It is a load sensing component that allows user guided positioning of the robotic arm.

Figure 7:
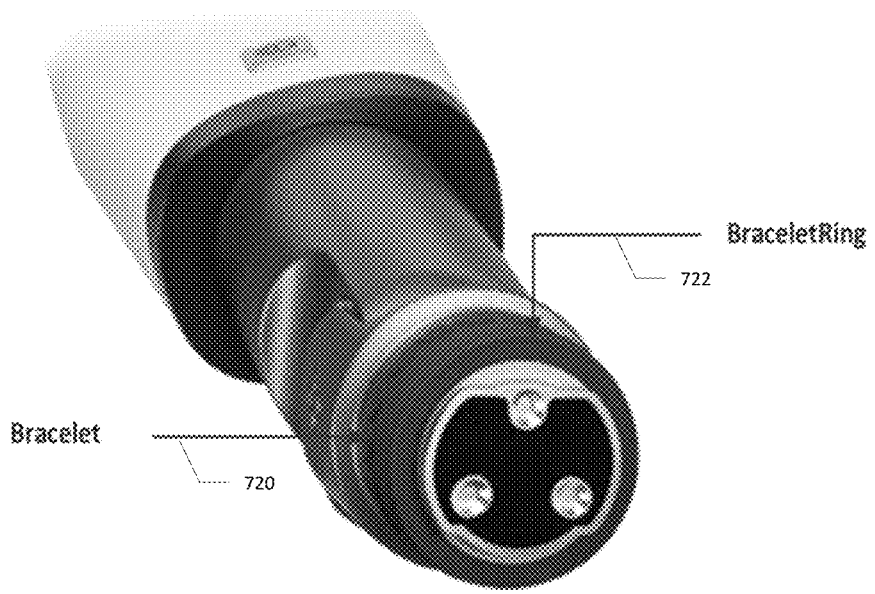
FIG. 7 illustrates the lower arm.

To initiate motion, squeeze the bracelet ring with the thumb and forefinger on opposite sides. While squeezed, apply light force toward the desired direction of motion. The robotic arm will move in the desired direction. The arm moves manually in any direction or along a trajectory if a screw plan is active. FIG. 7 illustrates the lower arm which includes a bracelet 700 and a bracelet ring 722.

Information Ring

Figure 8:
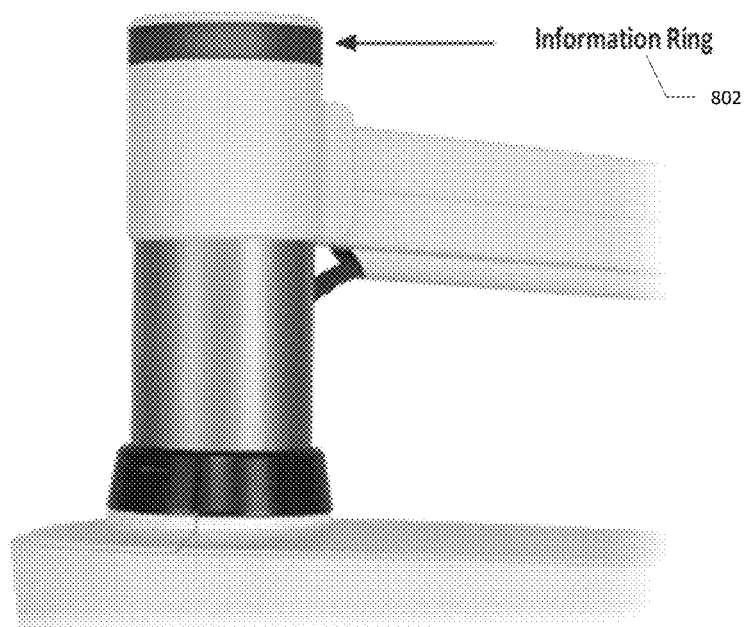
FIG. 8 illustrates the upper part of the vertical column.

The information ring is located on the upper part of the vertical column. The information ring indicates the status of the robotic computer system. The information ring light blinks while the system is booting up; a solid green light is displayed when the system is ready. Individual colors are used to indicate status, as shown in the table below. FIG. 8 illustrates the upper part of the vertical column in which includes an information ring 800 that is limited to provide information indications to a user.

| Information ring color indications | |
| --- | --- |
| Color | Description |
| Red | System is in an error state. Stop all tasks and resolve the issue immediately as it is either a safety issue or a serious problem with the system. |
| Yellow | System is in a state in which user intervention is required before a planned trajectory can be activated. |
| Green | System is ready. |

Camera Stand

Figure 9:
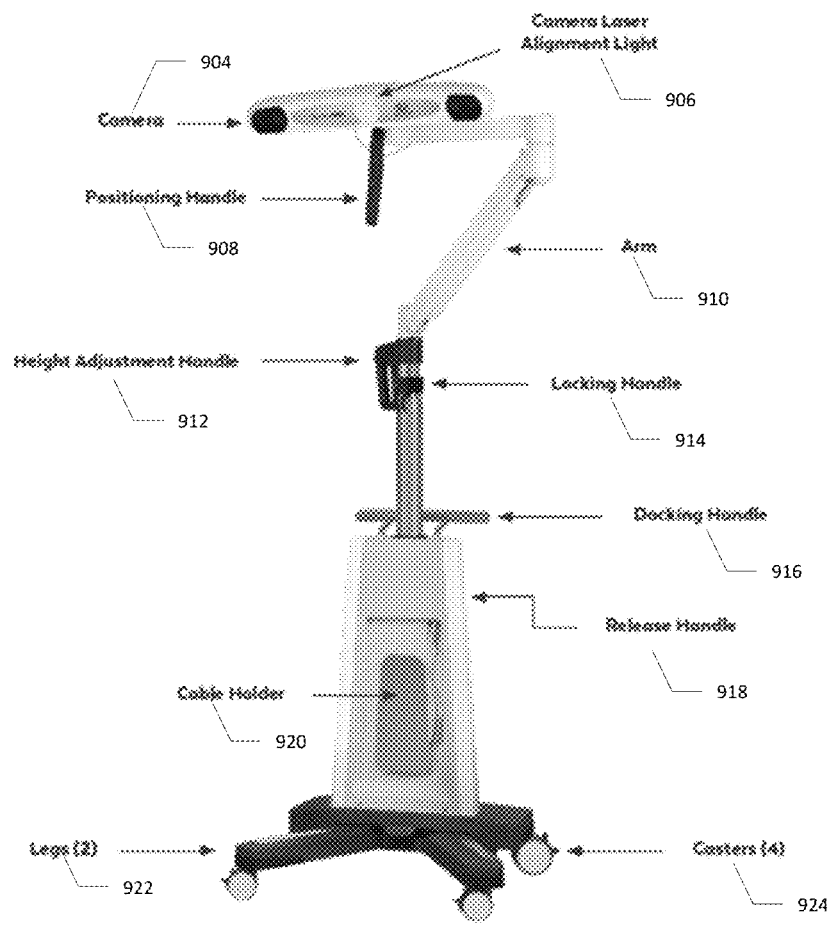
FIG. 9 illustrates the camera stand.
Figure 10:
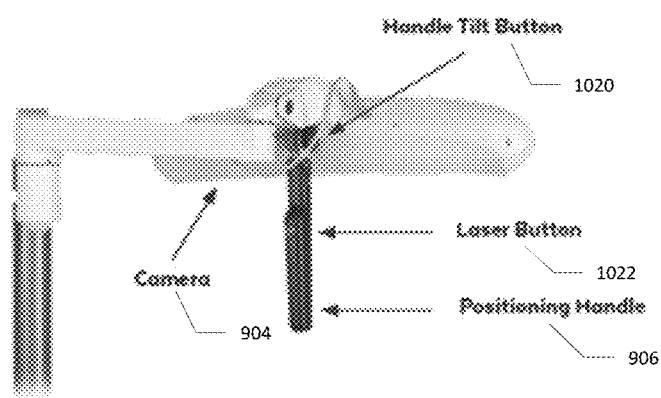
FIG. 10 illustrates the rear view of the camera stand showing alignment buttons.

The camera stand is mobile and adjusts in order to position the camera to view the operating field and optical markers. FIG. 9 illustrates the camera stand. The camera stand includes: a camera 904; a camera laser alignment light 906; a positioning handle 908; a support arm 910; a height adjustment handle 912; a locking handle 914; a docking handle 916; a release handle 918; a cable holder 920; legs 922; and casters 924. FIG. 10 illustrates the rear view of the camera stand showing alignment buttons. The camera stand further includes a handle tilt button 1020 and a laser button 1022.

| Camera stand functions | |
| --- | --- |
| Item | Function |
| Camera | Used to detect the reflective markers and is attached to the top of the camera stand. For more information, please refer to the NDI Passive Polaris Spectra User Guide. |
| Positioning Handle | Used to adjust the camera position to ensure the surgical field is in view. |

| Camera stand functions | |
| --- | --- |
| Item | Function |
| Handle Tilt Button | Used to adjust the angle of the positioning handle with respect to the camera in the field of view. |
| Laser Button | Turns the camera laser alignment light on and off. The laser light is used for assistance in aligning the camera in the field of view. |
| Arm | Provides a large range of positions for the camera. |
| Height Adjustment Handle | Allows for adjustment of camera height. |
| Locking Handle | Used to lock camera position. |
| Docking Handle | Used to collapse the legs for docking the camera stand into the Robotic Base Station. |
| Release Handle | Releases the camera from the Robotic Base Station. |
| Casters | The camera stand contains four casters. The rear casters are lockable to prevent the camera stand from moving. |
| Legs | The camera stand legs swing inward for docking and outward when deployed. |
| Cable Holder | Provides storage for the camera stand cable. |

Cabling

The following cable characteristics are required for connecting to external devices:

HDMI—Connecting to an external HDMI Monitor requires a shielded HDMI-Male to HDMI-Male cable.

Network—Connecting to a Hospital network can be done with an unshielded CAT-5e Ethernet cable.

Electronic Components of Surgical Robot

Figure 79:
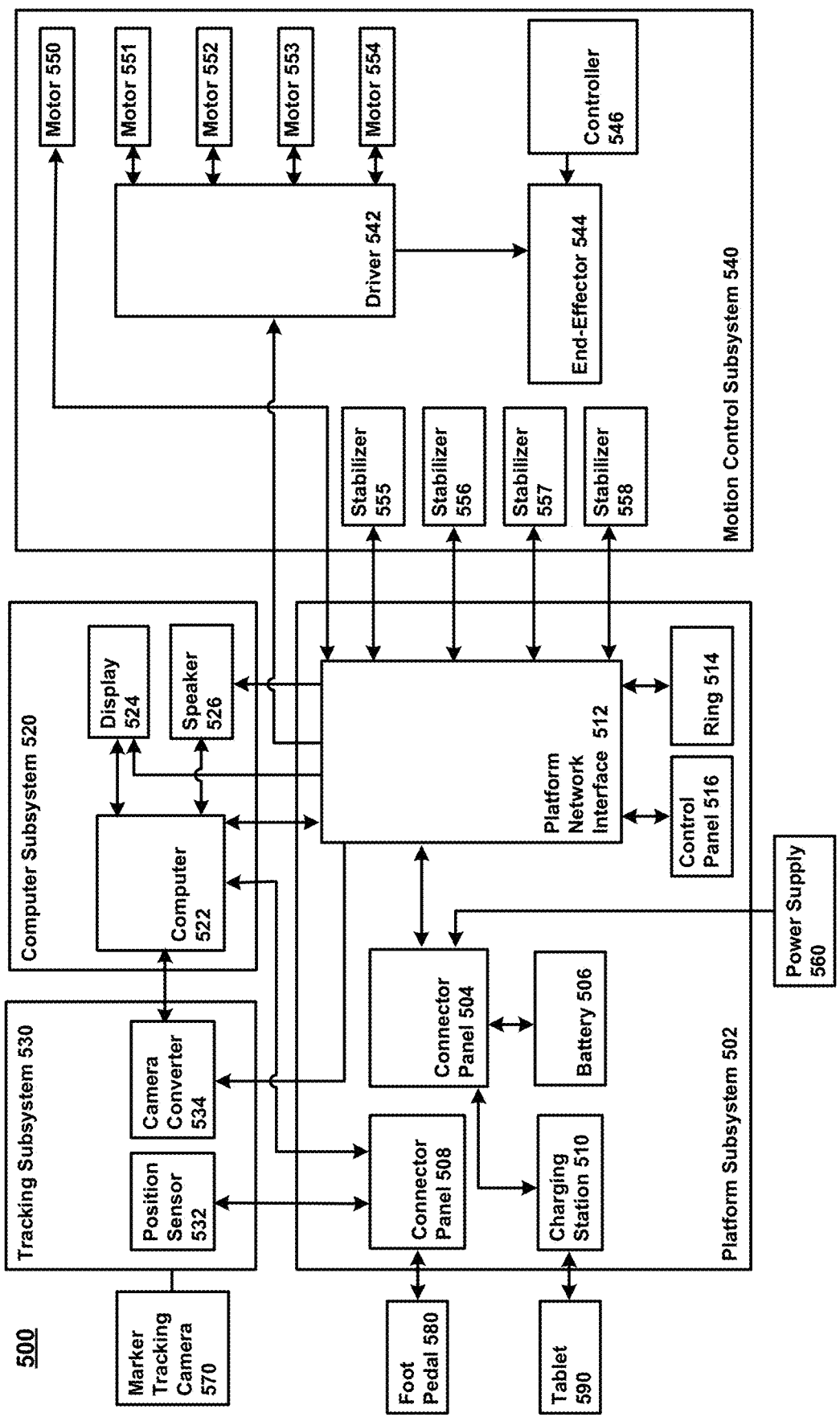
FIG. 79 illustrates a block diagram of electronic components of a robot portion of a robot surgical platform which is configured according to embodiments.

FIG. 79 illustrates a block diagram of electronic components of a robot 500 portion of a robot surgical platform which is configured according to embodiments. The robot 500 can include platform subsystem 502, computer subsystem 520, motion control subsystem 540, and tracking subsystem 530. Platform subsystem 502 can include battery 506, power distribution module 504, platform network interface 512, and tablet charging station 510. Computer subsystem 520 can include computer 522, display 524, and speaker 526. Motion control subsystem 540 can include driver circuit 542, motors 550, 551, 552, 553, 554, stabilizers 555, 556, 557, 558, end-effector 544, and controller 546 (e.g., one or more processors and associated circuitry). Tracking subsystem 530 can include position sensor 532 and camera converter 534 which is connectable to a marker tracking camera 570, e.g., via the platform network interface 512. Robot 500 can include a foot pedal 580 and tablet computer 590.

Input power is supplied to robot 500 via a power source 560 which may be provided to power distribution module 504. Power distribution module 504 receives input power and is configured to generate different power supply voltages that are provided to other modules, components, and subsystems of robot 500. Power distribution module 504 may be configured to provide different voltage supplies to platform network interface 512, which may be provided to other components such as computer 520, display 524, speaker 526, driver 542 to, for example, power motors 550, 551, 552, 553, 554 and end-effector 544, ring 514, camera converter 534, and other components for robot 500 for example, fans for cooling the various electrical components.

Power distribution module 504 may also provide power to other components such as tablet charging station 510 that may be located within a tablet drawer. Tablet charging station 510 may be configured to communicate through a wired and/or wireless interface with tablet 590. Tablet 590 may be used to display images and other information for use by surgeons and other users consistent with various embodiments disclosed herein.

Power distribution module 504 may also be connected to battery 506, which serves as a temporary power source in the event that power distribution module 504 does not receive power from input power 560. At other times, power distribution module 504 may serve to charge battery 506 when needed.

Other components of platform subsystem 502 can include connector panel 508, control panel 516, and ring 514. Connector panel 508 may serve to connect different devices and components to robot 500 and/or associated components and modules. Connector panel 508 may contain one or more ports that receive lines or connections from different components. For example, connector panel 508 may have a ground terminal port that may ground robot 500 to other equipment, a port to connect foot pedal 580 to robot 500, and/or a port to connect to tracking subsystem 530. The tracking subsystem 530 can include a position sensor 532, camera converter 534, and the marker tracking camera 570 which may be supported by a camera stand. Connector panel 516 can include other ports to allow USB, Ethernet, HDMI communications to other components, such as computer 520.

Control panel 516 may provide various buttons or indicators that control operation of robot 500 and/or provide information regarding robot 500. For example, control panel 516 may include buttons to power on or off robot 500, lift or lower stabilizers 555-558 that may be designed to engage casters to lock robot 500 from physically moving and/or to raise and lower the robot base and/or a vertical support for the robot arm. Other buttons may control robot 500 to stop movement of a robot arm in the event of an emergency, which may remove all motor power and apply mechanical and/or electromechanical brakes to stop all motion from occurring. Control panel 516 may also have indicators notifying the user of certain system conditions such as a line power indicator or status of charge for battery 506.

Ring 514 may be a visual indicator to notify the user of robot 500 of different modes that robot 500 is operating under and certain warnings to the user.

Computer 522 of the computer subsystem 520 includes at least one processor circuit (also referred to as a processor for brevity) and at least one memory circuit (also referred to as a memory for brevity) containing computer readable program code. The processor may include one or more data processing circuits, such as a general purpose and/or special purpose processor, e.g., microprocessor and/or digital signal processor. The processor is configured to execute the computer readable program code in the memory circuit to perform operations, which may include some or all of the operations described herein as being performed by a surgical robot and may further perform some or all of the operations described herein as being performed by a surgical implant planning computer.

The program code includes an operating system and software to operate robot 500. Computer 522 may receive and process information from other components (for example, tracking subsystem 530, platform subsystem 502, and/or motion control subsystem 540) in order to display information to the user. Further, computer subsystem 520 may include speaker 526 to provide audio notifications from the computer 522 to the user.

Tracking subsystem 530 can include position sensor 532 and camera converter 534. The position sensor 532 may include the marker tracking camera 570. Tracking subsystem 530 may track the location of markers that are located on the different components of robot 500 and/or instruments used by a user during a surgical procedure. This tracking may be conducted in a manner consistent with the present disclosure which can include the use of infrared technology that illuminates and enables tracking by the camera 570 of the location of active or passive elements, such as LEDs or reflective markers, respectively. The location, orientation, and position of structures having these types of markers may be provided to computer 522 which may be shown to a user on display 524 and/or tablet 590. For example, a surgical instrument or other tool having these types of markers and tracked in this manner (which may be referred to as a navigational space) may be shown to a user in relation to a three dimensional image of a patient's anatomical structure, such as a CT image scan, fluoroscopic image, and/or other medical image.

The robot 500 can include a robot base that is coupled to a robot arm which is movable by the motors, e.g., one or more of motors 550-554, relative to the robot base. The robot arm can include an upper arm connected to a vertical support and a lower arm that is rotatably coupled to an end of the upper arm and extends to couple to the end-effector 544. Motion control subsystem 540 may be configured to physically move a vertical column of the robot 500, e.g., raise and lower the robot arm and/or the robot base in a vertical direction, move an upper arm of the robot 500, move a lower arm of the robot 500, and/or rotate the end-effector 544. The physical movement may be conducted through the use of one or more motors 550-554. For example, motor 550 may be configured to vertically lift or lower the robot base and/or the robot arm in a vertical direction. Motor 551 may be configured to laterally move an upper arm around a point of engagement. Motor 552 may be configured to laterally move a lower arm around a point of engagement with the upper arm. Motors 553 and 554 may be configured to move the end-effector 544 in a manner that controls the roll and/or tilt, thereby providing multiple angles that end-effector 544 may be moved. These movements may be performed by controller 546 responsive to commands from the computer 522 and which may control these movements through load cells disposed on the end-effector 544 and activated by a user engaging these load cells to move the end-effector 544 in a desired manner.

The robot 500 may augment manual input by a user, e.g., when a user applies force to one or more load cells on the end-effector 544, and/or provide automatic movement of the robot arm. The robot 500 may also augment manual movement by a user and/or provide automatic movement of a vertical column of the robot base. For automatic movement, the computer 522 may respond to receiving input from a user, such as by indicating on display 524 (which may be a touchscreen input device) the location of a surgical instrument or component on a three dimensional medical image of the patient's anatomy on display 524. The computer 522 can control one or more of the motors 550-554 to perform automatic movement of the robot arm along a trajectory that has been computed to move the end effector 544 based on location of the user's input relative to the medical image. The user may initiate automatic movement by stepping on foot pedal 580 and/or by manipulation of another user interface.

Instruments

End Effector

Figure 11:
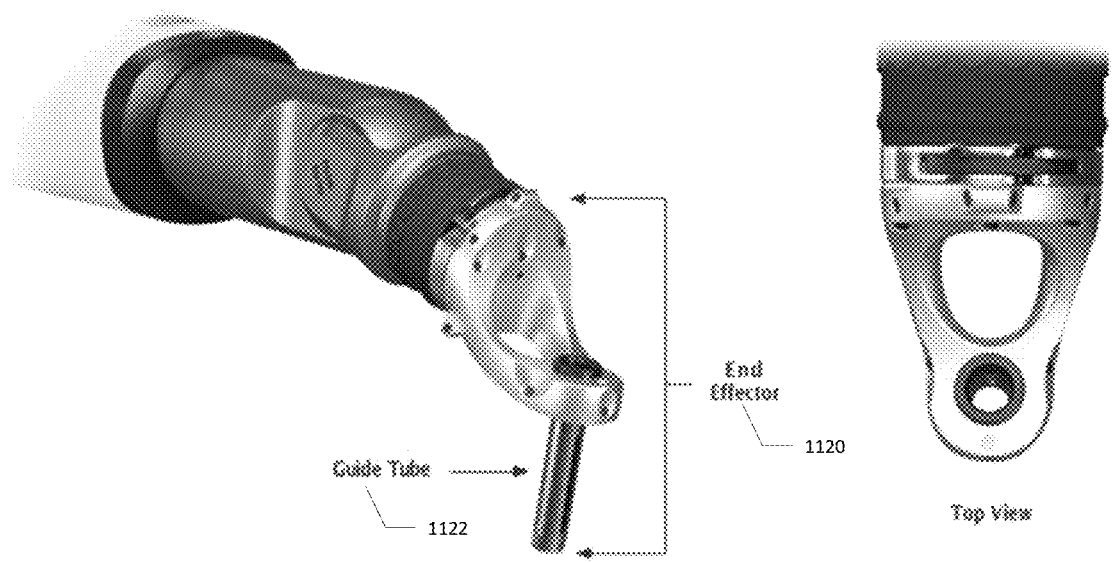
FIG. 11 illustrates isometric and top views of the end-effector.

The end-effector is the interface between the robotic arm and the system specific surgical instruments. It allows for a rigid connection through the sterile drape to provide precise positioning of instruments placed within its guide tube. The end-effector is provided as a separate component and is sterilized by the user prior to use. FIG. 11 illustrates the isometric and top view of the end-effector 1122 including a guide tube 1122.

The end-effector is powered wirelessly from the robotic arm. This power is used to drive the active markers that are used by the camera to identify the location and orientation of the end-effector. The blue indicator LED illuminates when the end-effector is powered.

Two end-effectors are available to interface with various surgical instruments. They differ only in the diameter of the guide tube; the active markers have the same geometries. The end-effectors are etched with the guide tube diameter and are color-coded to help ensure that the corresponding size instruments are used.

The 15 mm end-effector is used with all navigated instruments except REVOLVE® instruments, and the 17 mm end-effector is used with REVOLVE® instruments. Non-navigated Globus instruments may be used with either end-effector; they are not sized to the guide tube, but must fit within the inner diameter Instrument Sensing Ring Located within the guide tube of the end-effector is an instrument sensing ring. A detector circuit is embedded within the sensing ring that detects when a metal instrument is inserted through the guide tube and disables the active markers and prevents movement of the robotic arm. The visible LED on the end-effector does not illuminate when a metallic instrument is inserted, indicating that an instrument is detected and the active IR emitters are disabled. Disabling the IR emitters prevents the robotic arm from moving. Non-metallic instruments are not identified by the sensing ring and may not be used in the guide tube.

Detent Mechanism

Figure 12:
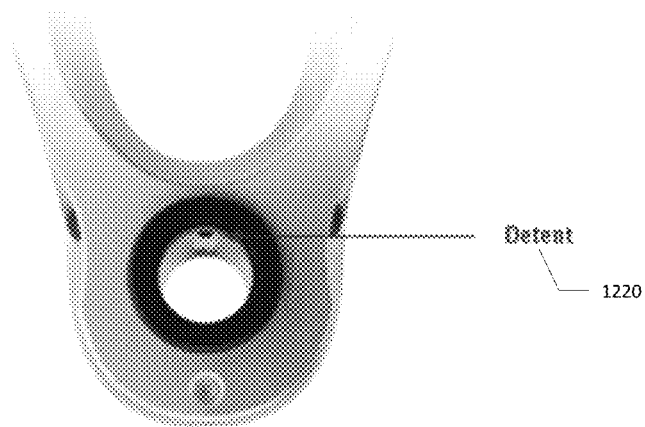
FIG. 12 illustrates the detent mechanism on the instrument sensing ring.

Size 15 mm end-effectors have a detent mechanism on the inside of the tube which interfaces with grooves on the array sleeves to resist array rotation. This aids in holding the tracking array oriented toward the camera while the operator rotates the instrument. FIG. 12 illustrates the detent mechanism 120 on the instrument sensing ring.

Scalpel

A specialized scalpel can be used to create a skin mark at the planned trajectory. Attach a standard scalpel blade to the handle.

Position the guide tube on the end-effector to the planned trajectory. Adjust the end-effector up or down along the trajectory to allow the scalpel to be viewed. Ensure that scalpel tip can be viewed before making the skin mark.

Figure 13:
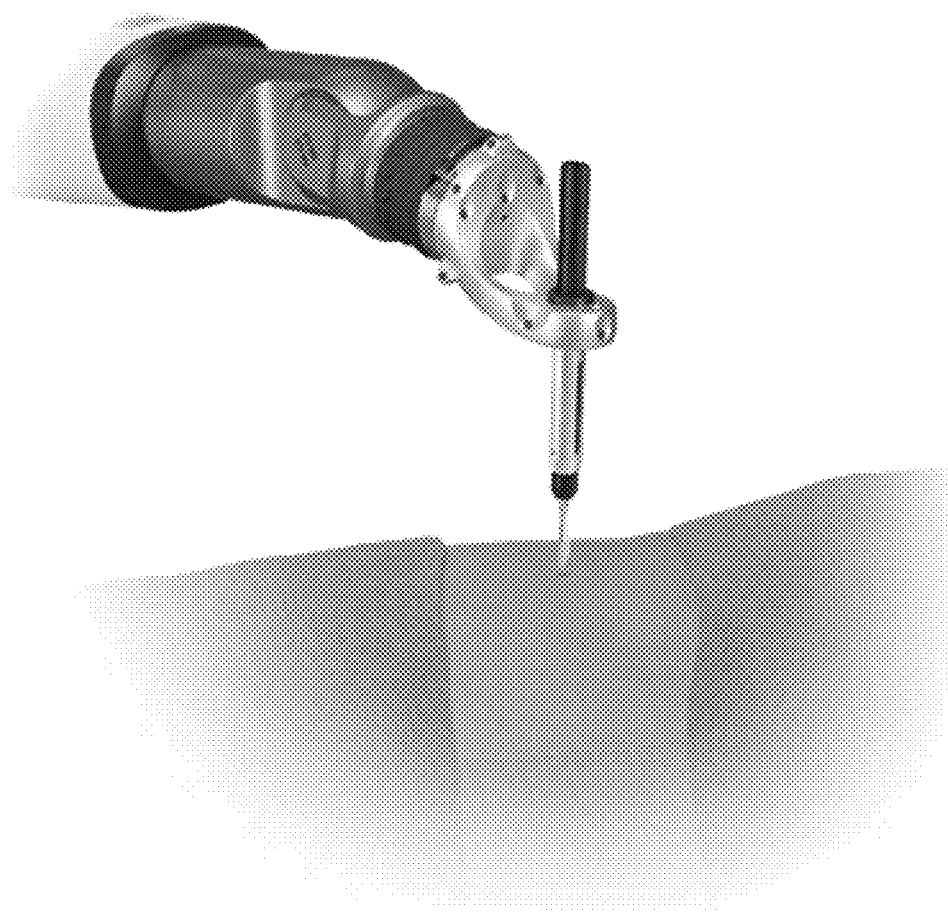
FIG. 13 illustrates a scalpel used through the guide tube.

Note: The scalpel has a metal core within the radiolucent PEEK material and is detected while in the guide tube. FIG. 13 illustrates a scalpel used through the guide tube.

Cannulas

Cannulas, or dilators, can be used for performing minimally invasive or other techniques that require sequential tissue dilation. The cannulas should only be used under trajectory guidance. Note: The terms "cannula" and "dilator" are used interchangeably.

Prior to performing sequential tissue dilation, a scalpel may be used through the guide tube to create a skin mark at the desired trajectory. Move the guide tube away from the trajectory using the bracelet, and create an incision with a scalpel. Refer to the Scalpel section of this manual for instructions.

Figure 14:
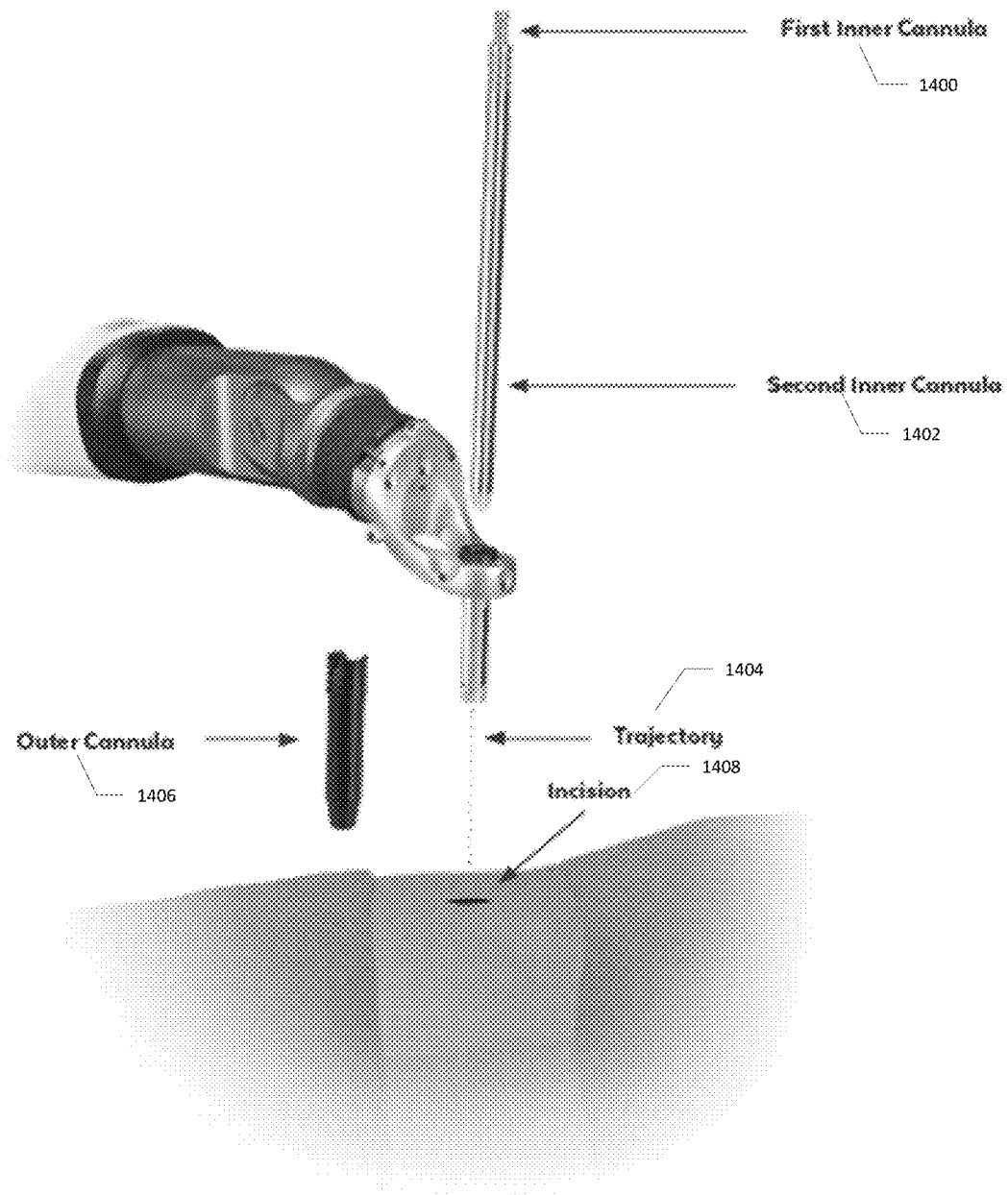
FIG. 14 illustrates the trajectory of the outer cannula.
Figure 15A:
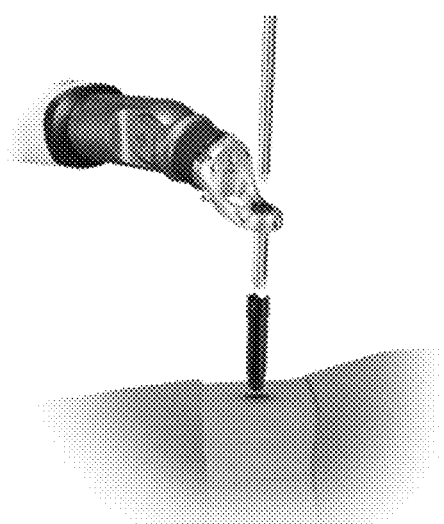
FIGS. 15(a)-15(f) illustrate one technique for dilating tissue with the devices.
Figure 15B:
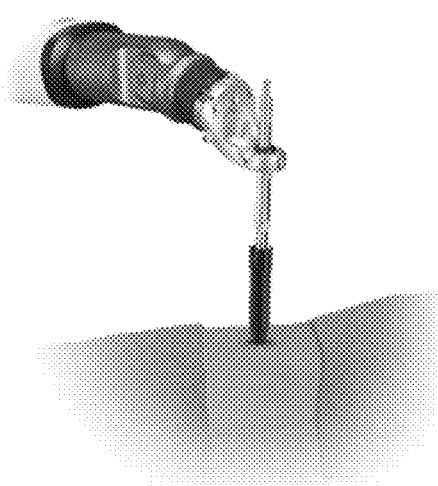
Figure 15C:
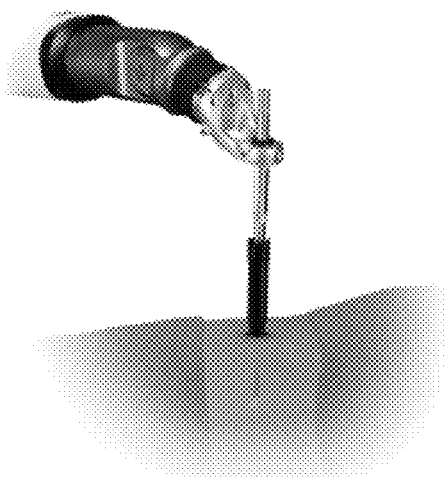
Figure 15D:
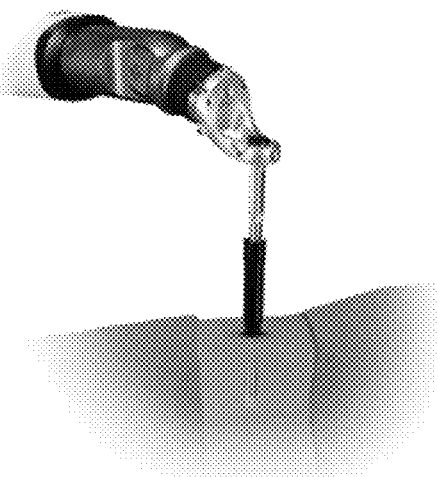
Figure 15E:
Figure 15F:
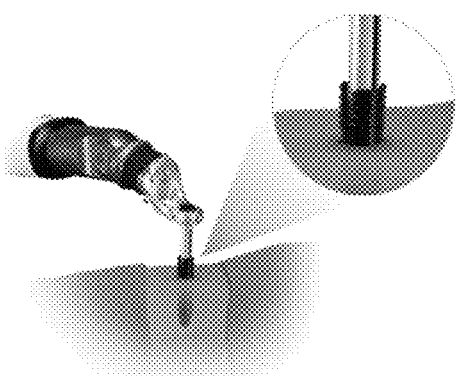

Once the guide tube is at the desired trajectory, position the outer cannula under the guide tube and above the incision, along the same trajectory. Insert the two inner cannulas into the guide tube and through the outer cannula, and rest on the skin. To sequentially dilate the tissue, slowly insert the first (smallest) cannula into the incision using a cannula pusher. Then advance the second cannula in the same manner. Complete tissue dilation by slowly advancing the outer cannula over the inner cannula. Remove the inner cannula. Lower the guide tube until it sits just within the outer cannula. Perform surgery through the guide tube and outer cannula. FIG. 14 illustrates the trajectory of the outer cannula. Referring to FIG. 14, a first inner cannula 1400 is slid into a second inner cannula 1402 along trajectory 1404 into the outer cannula 1406 which is placed within the incision 1408. FIGS. 15(a)-15(g) illustrates one technique for dilating tissue with the devices. FIG. 15a illustrates how the outer cannula is positioned above the incision. FIG. 15b illustrates how the cannulas is placed into the guide tube such that it rests on skin. FIG. 15c illustrates how the first inner cannula is inserted into the incision. FIG. 15d illustrates how the second inner cannula is then inserted into the incision. FIG. 15e illustrates how the outer cannula is then inserted into the incision. FIG. 15f illustrates both inner cannulas then being removed. FIG. 15g illustrates lowering the guide tube until it sits within the outer cannula.

Navigated Instruments

The navigated surgical instruments for use with robotic computer system include drills, awls, probes, taps, and drivers, which may be used to insert Globus screws. These instruments can be used with arrays if navigation is desired, or without arrays if navigation is not used. Each instrument and corresponding array must be assembled prior to use. Instruments are identified by a unique array pattern that is recognized by the camera.

Figure 16:
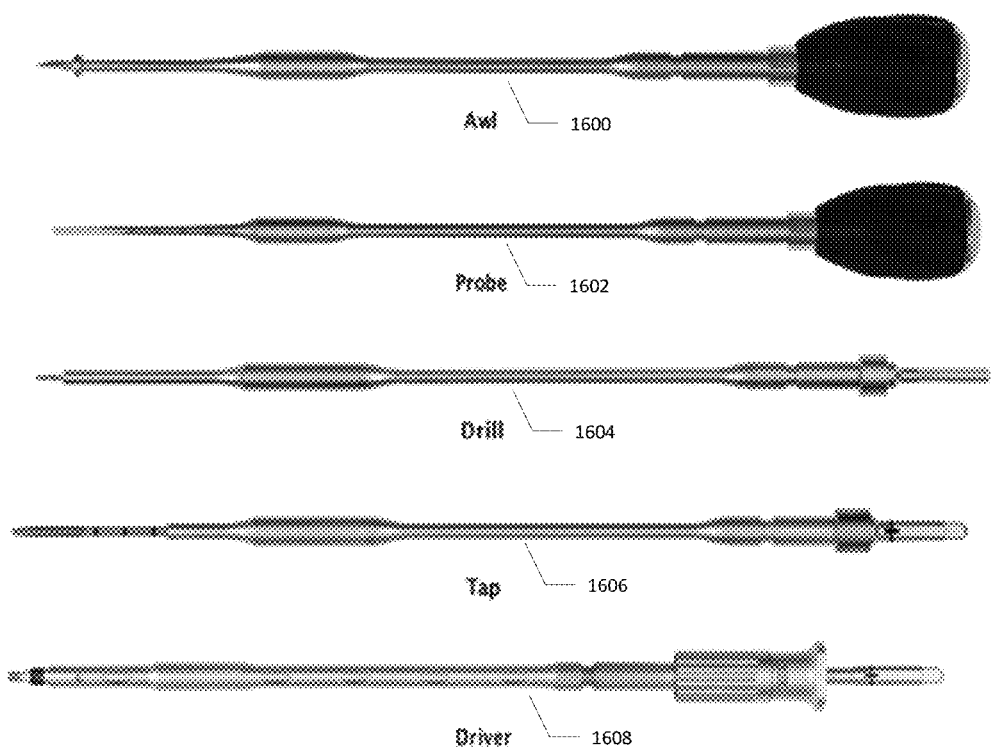
FIG. 16 illustrate some embodiments of the navigated survival instruments.

Navigated instruments are available for each Globus implant system. Refer to the specific system instrument brochures for more information. FIG. 16 illustrate some embodiments of the navigated instruments. The instruments include an awl 1600, a probe 1602, a drill 1604, a tap 1606, and a driver 1608.

Arrays

Arrays have 4 posts for attaching reflective markers and are available for use with the surgical instruments. The navigated surgical instruments are assembled to a corresponding instrument array, designed with a unique marker pattern which identifies the instrument type. The array is etched with the specific instrument type, e.g. "AWL", "PROBE", "DRILL", "TAP", "DRIVER". Each instrument array has a verification divot, used for instrument verification.

The verification probe has a built-in array with posts for the reflective markers and is used to verify each instrument before use.

Figure 17:
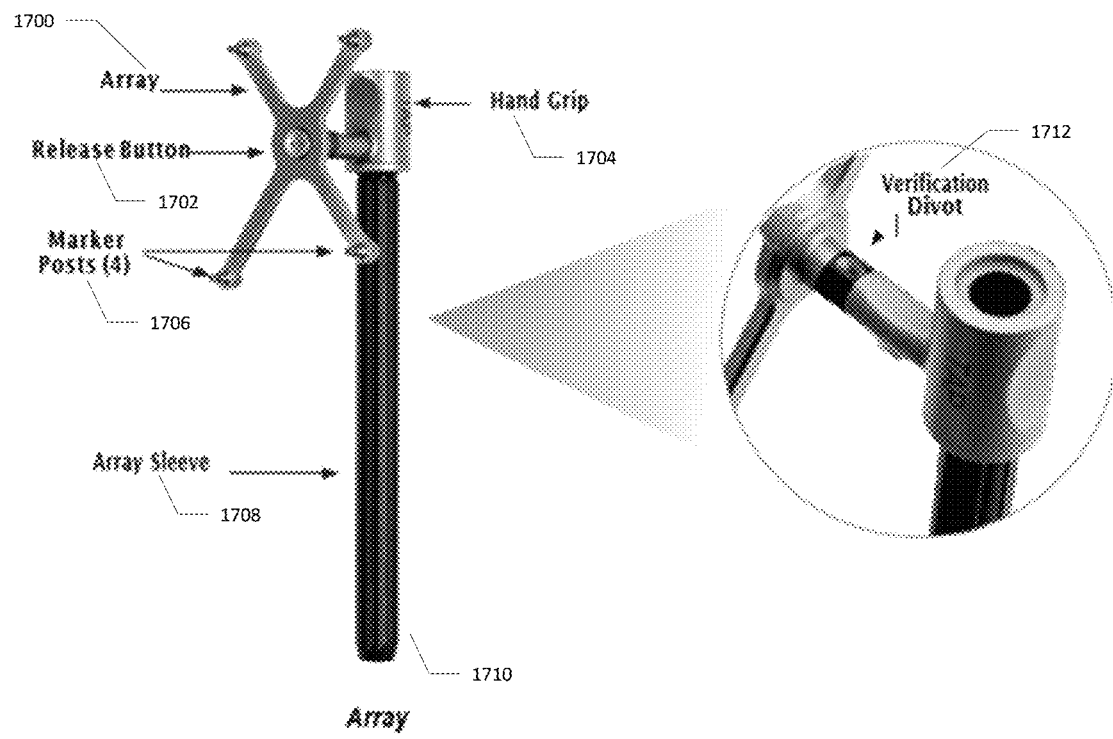
FIG. 17 illustrates the array.
Figure 18:
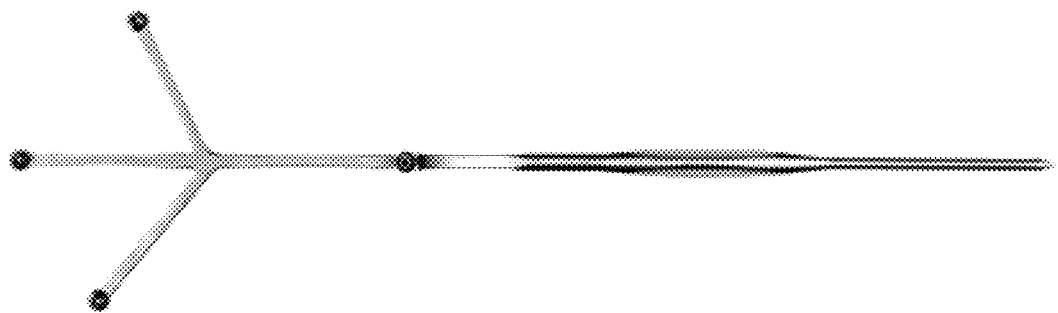
FIG. 18 illustrates the verification probe.

Arrays used with instruments for the standard 15 mm end-effector are identified by a black sleeve. Arrays used with instruments for the 17 mm end-effector are identified by a tan sleeve. FIG. 17 illustrates the array 1700 with a release button 1702, a handgrip 1704, a marker post 1706, an array sleeve 1708, and array support 1710. FIG. 17 also illustrates a verification divot 1712 between the array 1700 and the handgrip 1704. FIG. 18 illustrates the verification probe.

Patient Attachment Instruments

Patient attachment instruments are secured to the patient's rigid anatomy, depending on the specific surgical procedure or preference, and are available in various configurations. These instruments may be secured to a variety of anatomical sites. The rod attachment instrument is designed to attach to an existing spinal rod.

Patient attachment instruments must be safely and rigidly secured to the patient to achieve navigation and guidance accuracy. Verify secure attachment by applying a light force to the distal end of the attachment instrument in all directions. If secure attachment is not maintained during the procedure, the surveillance marker will demonstrate excessive movement; if this occurs, reposition the patient attachment instrument and re-register the patient to the patient images.

Figure 19:
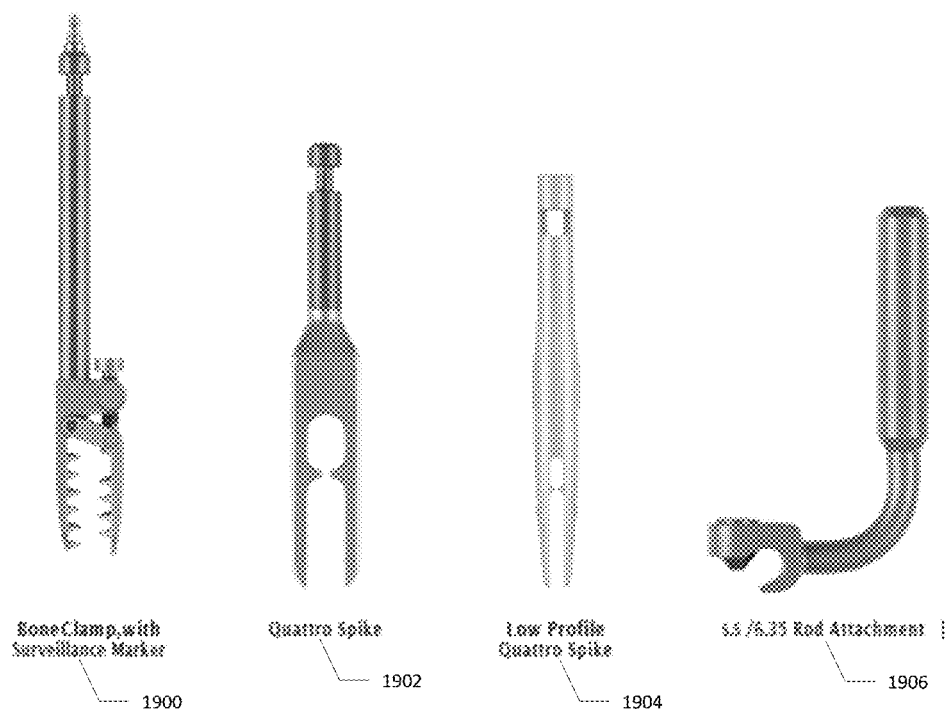
FIG. 19 illustrates the patient attachment instruments.

Refer to the specific procedure in the Application section for recommended anatomical locations. FIG. 19 illustrates the patient attachment instruments, which include a bone clamp 1900 with surveillance marker, a quattro spike 1902, a low profile quattro spike 1904, and a rod attachment 1906.

Bone Clamps

Bone clamps are clamped onto anatomical structures such as the spinous process, iliac crest, long bone, or any rigid bony structure that can be safely clamped.

Figure 20:
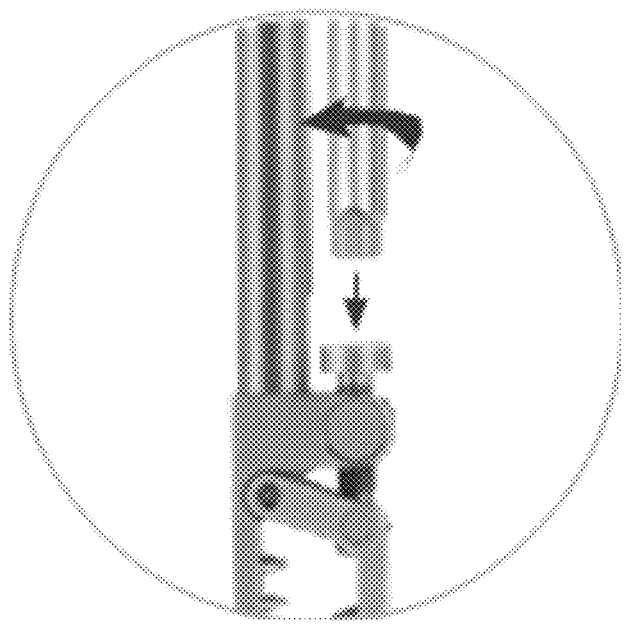
FIG. 20 illustrates tightening bone clamp using clamp driver.

The bone clamp is placed onto rigid bony anatomy. The clamp driver is used to tighten the bone clamp. To remove, loosen the bone clamp with the clamp driver, attach the removal tool and lift up the bone clamp. FIG. 20 illustrates tightening bone clamp using clamp driver.

Quattro Spikes

Quattro spikes are inserted into rigid bone of the iliac crest or long bone. The quattro spike is inserted into rigid bony anatomy and gently impacted with a mallet.

Figure 21:
FIG. 21 illustrates the guide post and the quattro spike.
Figures 22A, 22B, 22C, 22D:
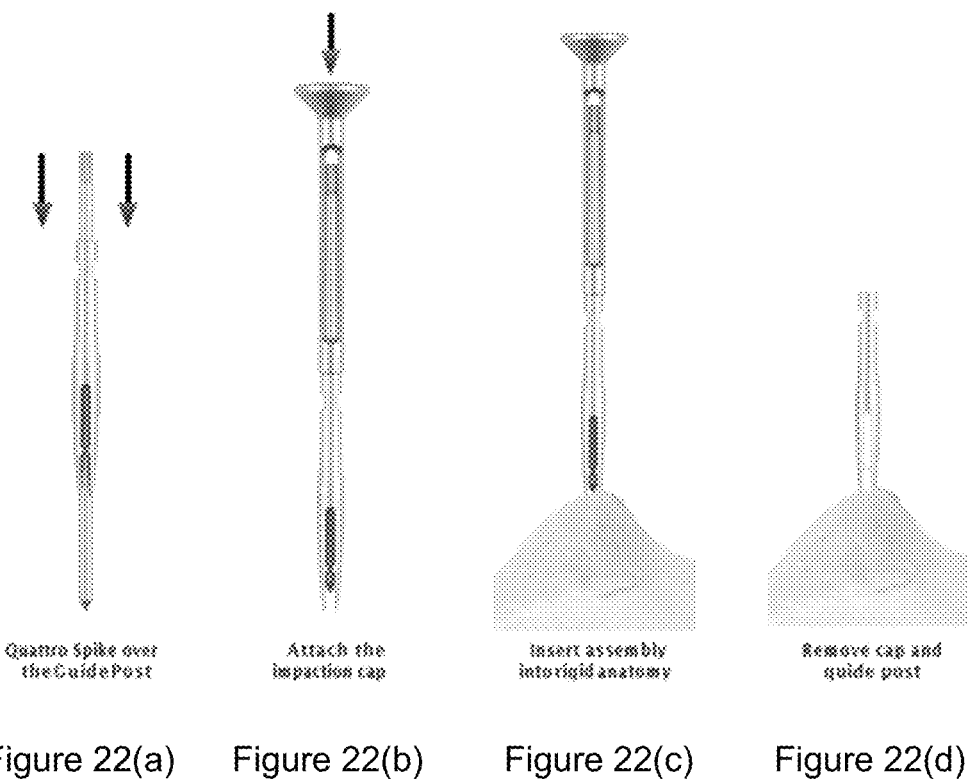
FIGS. 22(a)-22(d) illustrate one method for inserting a low profile quattro spike into rigid bony anatomy.

The low profile quattro spike is inserted using a guide post and impaction cap. Find the desired anatomy using the guide post. Place the patient attachment instrument over the guide post. Attach the impaction cap (for low profile quattro spike). Gently impact the assembly with a mallet to insert into bony anatomy. Remove the impaction cap and guide post from the spike. FIG. 21 illustrates the guide post 2100 and the quattro spike 2102. FIGS. 22(*a*)-22(*d*) illustrates one method for inserting the quattro spike into rigid bony anatomy. FIG. 22(*a*) illustrates positioning the quattro spike over the guide post. FIG. 22(*b*) illustrates attaching the impaction cap. FIG. 22(*c*) illustrates inserting the assembly into a rigid anatomy. FIG. 22(*d*) illustrates removing the cap and guide pose.

Rod Attachment Instrument

Figure 23:
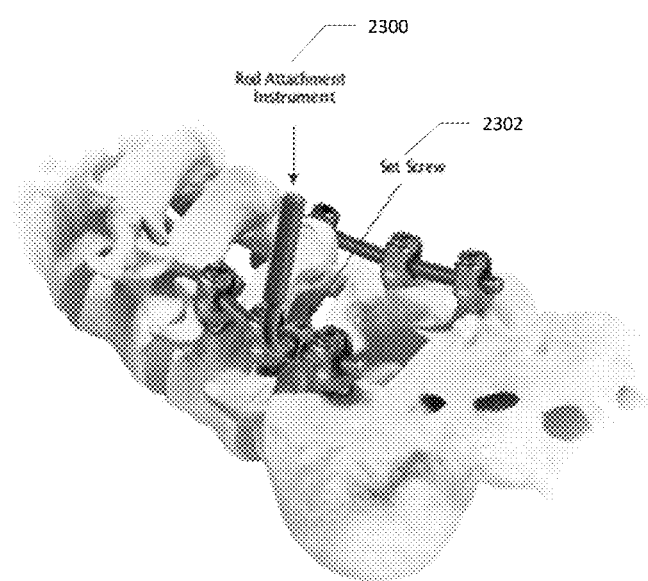
FIG. 23 illustrates inserting a rod attachment instrument including a set screw, to attach to the existing spinal rod.

The rod attachment instrument is designed to attach to an existing spinal rod (4.5 mm to 6.35 mm diameter). Position the instrument on the existing spinal rod and tighten the set screw with a driver. Ensure a rigid connection. To remove, loosen the set screw and disengage from the rod. FIG. 23 illustrates the rod attachment instrument 2300 including a set screw 2302, which are attached to the existing spinal rod.

Surveillance Marker

Figure 24:
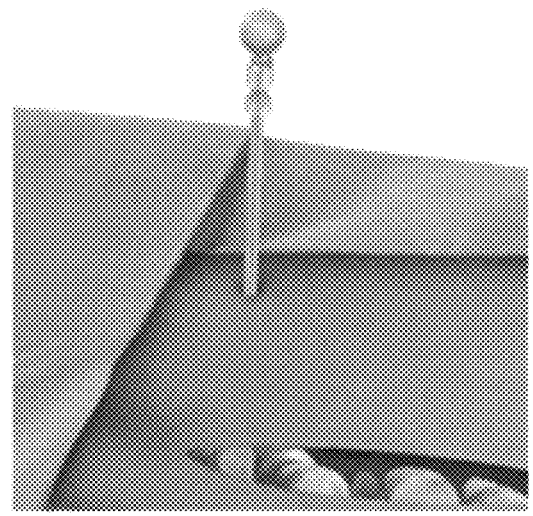
FIG. 24 illustrates a surveillance marker.

FIG. 24 illustrates a surveillance marker. The surveillance marker is a single reflective marker used to monitor a shift in the Dynamic Reference Base (DRB). Surveillance markers may be used alone or in conjunction with a bone clamp.

Figure 25:
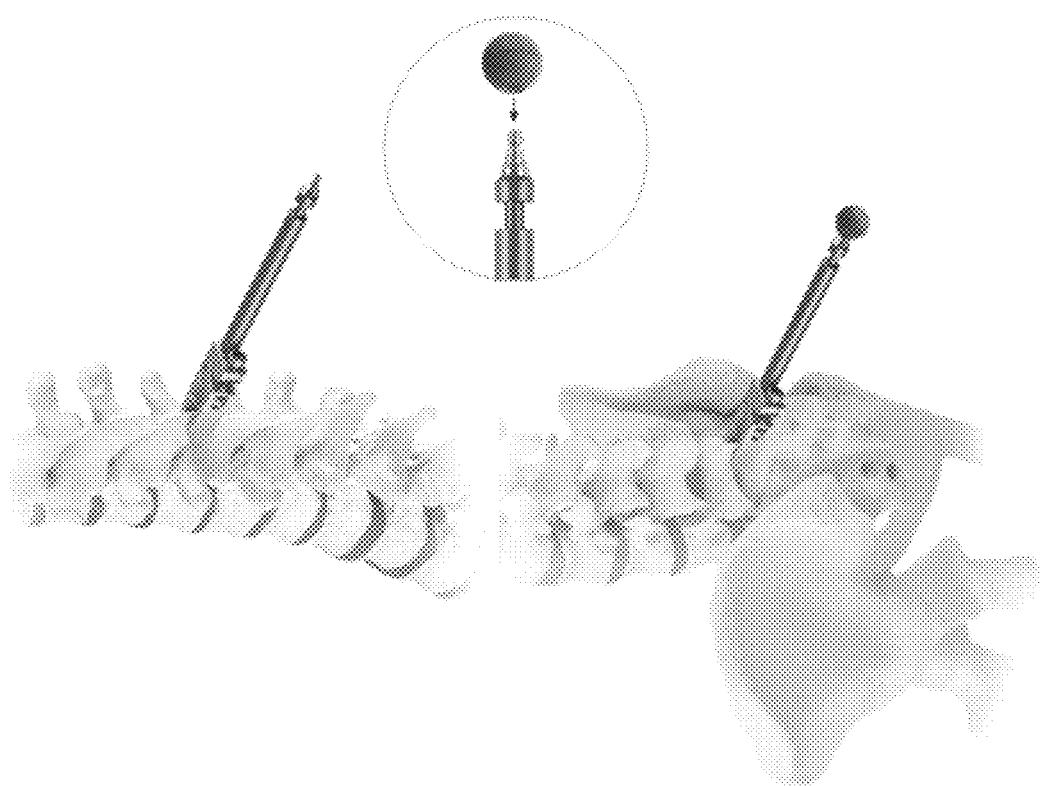
FIG. 25 illustrates a use of a surveillance marker with a bone clamp.

Surveillance markers are directly inserted into the iliac crest or long bone, or may be attached to the spinous process using a bone clamp. FIG. 25 illustrates the use of a surveillance marker with a bone clamp. To use a bone clamp with the marker, attach a disposable surveillance marker 240 onto the tip of the bone clamp. Use the clamp driver to secure the bone clamp. Verify that the bone clamp is rigidly secured.

Registration Instruments

The Dynamic Reference Base (DRB) and patient attachment instruments are used in the patient registration process.

Figure 26:
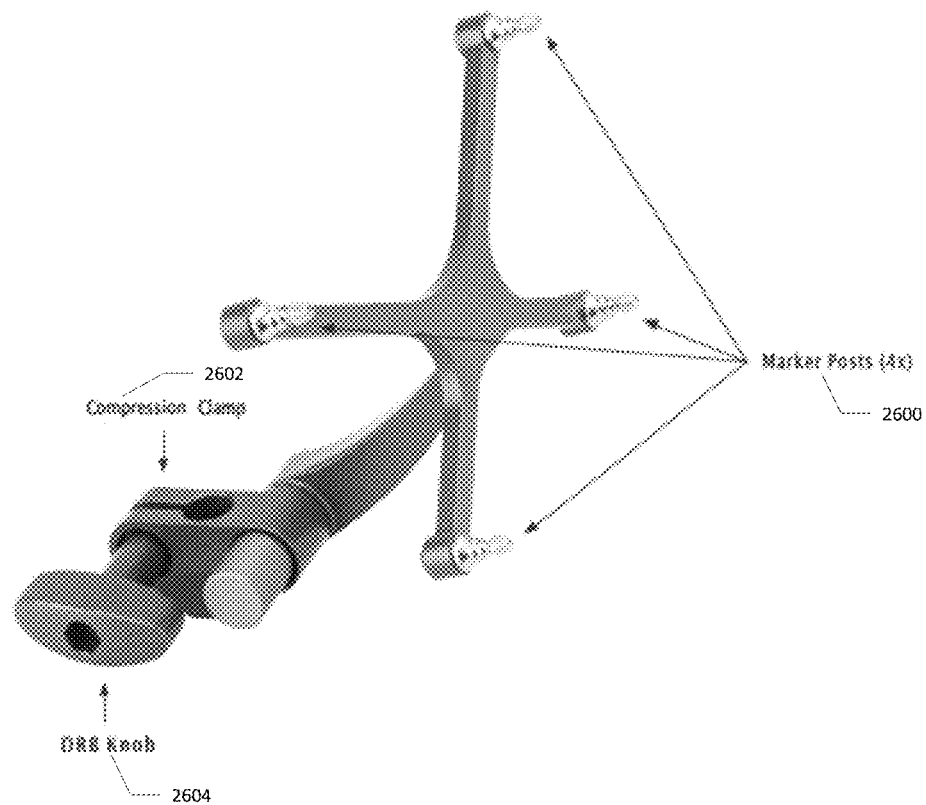
FIG. 26 illustrates a dynamic reference base.

The DRB is an array with 4 posts for reflective markers and allows the camera to track the location of the patient. The DRB may be attached to any of the patient attachment instruments, using the knob and compression clamp. FIG. 26 illustrates the dynamic reference base, which includes marker posts 2600 connected to a compression clamp 2602 operated by a DRB knob 2604.

Registration Fixtures

Intra-Op Ct Registration Fixture

The intra-op CT registration fixture, consisting of a registration fixture and pivoting arm, allows for any intra-operative CT image to be used with the robotic computer system software application. The pivoting arm and registration fixture are assembled prior to use by matching the starburst gears and snapping the two components together.

Figure 27:
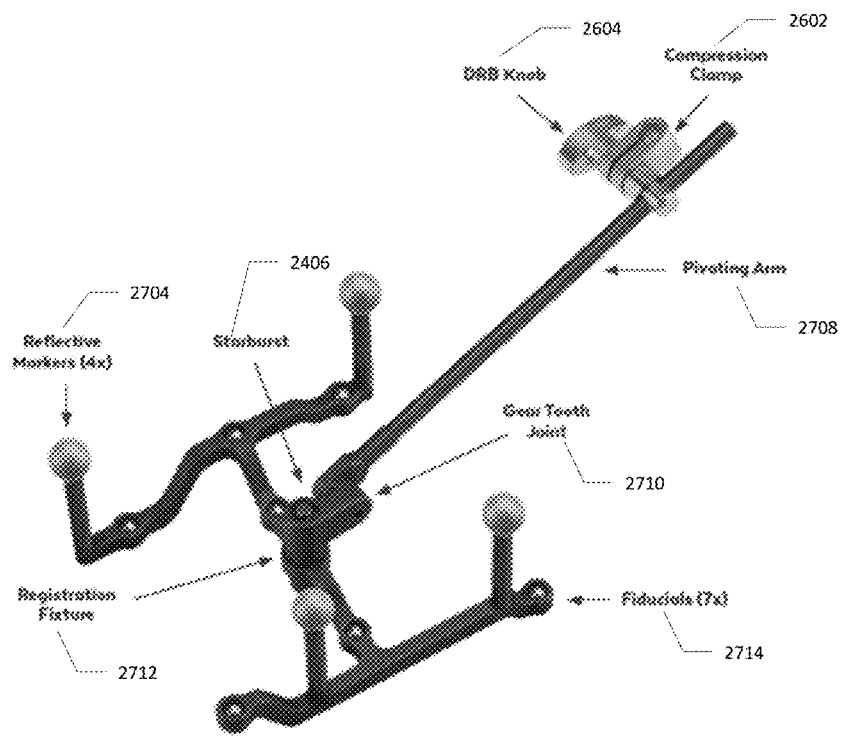
FIG. 27 illustrates a intra-op registration fixture and pivoting arm.

The intra-op registration fixture is placed onto a patient attachment instrument by clamping the compression clamp onto the shaft of the attachment instrument, allowing the fixture to hover over the surgical site. The fiducials are detected automatically in the intra-operative scan and are used to register the patient's anatomy during the scan to the DRB, which is tracked by the camera throughout the procedure. The reflective markers are detected by the camera. Once the registration is transferred to the DRB, the intra-op registration fixture is removed to provide access to the surgical site. FIG. 27 illustrates the intra-op registration fixture 2712 and pivoting arm 2708. FIG. 27 further illustrates the compression clamp 2602, the DRB knob 2604, a starburst connection 2406, a gear tooth joint 2710, and a set of seven fiducials 2714.

Fluoroscopy Registration Fixture

Figure 28:
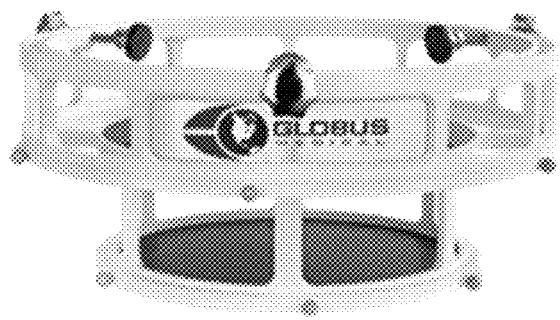
FIG. 28 illustrates a Fluoroscopy Registration Fixture.

FIG. 28 illustrates the Fluoroscopy Registration Fixture. The Fluoroscopy Registration Fixture allows for any intra-operative fluoroscopic image to be used with the robotic computer system software application. The fluoroscopy fixture is attached to the image intensifier of the fluoroscope using the integrated clamps. The fluoroscope and Fluoroscopy Registration Fixture are draped and the reflective markers are placed on the fixture, outside of the drape. The fixture should be positioned such that the reflective markers are seen by the camera in all intended fluoroscope positions (AP, lateral, etc).

Robotic Arm Motion

The robotic computer system robotic arm positions the end-effector to guide instruments for screw insertion at the desired trajectory. The surgeon manually performs surgery while the instruments are aligned in the desired trajectory for accurate screw placement. Note: The terms "screw plan", "screw trajectory" and "trajectory" are used interchangeably in this manual.

Motion of the robotic arm is only allowed with continuous pressing of the bracelet or foot pedal. The arm is manually moved by the user in Wrist mode, or is automatically moved to the selected trajectory in Trajectory mode.

In Wrist mode, the arm may be moved manually to any position within reach of the arm.

In Trajectory mode, the arm is automatically moved from the current position to the next screw plan when ready, or may be moved manually along a selected trajectory.

When moving from one screw plan to the next, the arm moves outwards along the current trajectory to a safe distance (200 mm) from the surgical site before moving to the new trajectory and downwards along the current trajectory to the anatomy.

| | | | Robotic arm motion modes | |
|---|---|---|---|---|
| Mode | Software | User Action | Automatic Motion | Manual Motion |
| Wrist Mode | No Plan Selected | PressFootPedal or Squeeze Bracelet | n/a | User may move arm in the desired direction |
| Trajectory mode | Plan Selected | Press Foot Pedal or Squeeze Bracelet | Arm moves automatically to new screw trajectory | After reaching the trajectory, user may move arm along trajectory only |

Figure 29:
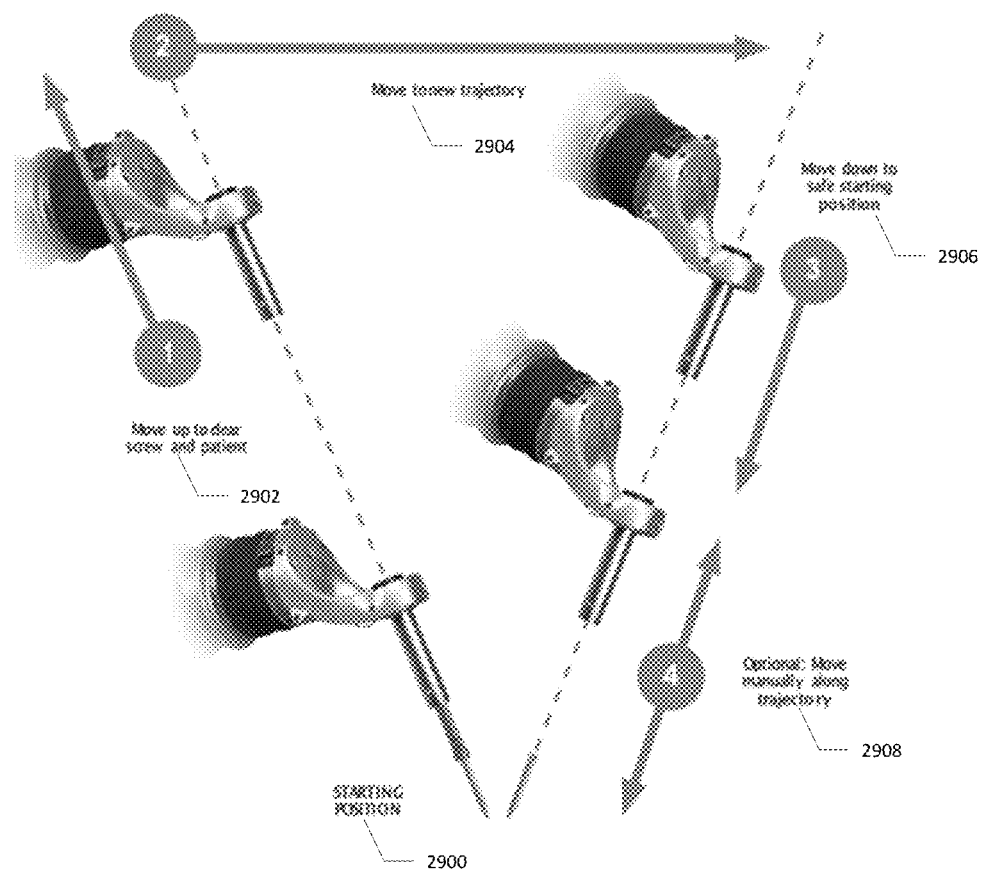
FIG. 29 illustrates an end effector motion when moving from one trajectory to the next, wherein 1, 2, and 3 are automatic movements; 4 is manual and optional.

Automatic motion of the arm occurs when moving the guide tube from the current position (either initially or at a current trajectory) to a new screw plan. Once the end-effector and attached guide tube have moved to a new screw plan, the guide tube is locked onto the trajectory and can be moved up and down along the trajectory. FIG. 29 illustrates the end effector motion when moving from one trajectory to the next, wherein 1, 2, and 3 are automatic movements; 4 is manual and optional. The illustrated movements include movement up along path 2902 from a starting position 2900 to clear the screw and patient, movement along a new trajectory path 2904, movement downward to a safe starting position along path 2906, and an optional movement along a trajectory path 2908 that may involve manual movement.

Automatic motion of the robotic arm may be stopped by the user, stopped by the system, or prevented.

To stop motion at any time, press the Emergency Stop button located on the base station.

Motion is stopped if the end-effector detects a force greater than 50 N (11 lbs).

Motion is also stopped in Trajectory mode when the DRB or the end-effector is not in view of the camera.

Motion is prevented when the sensing ring in the guide tube detects a metallic instrument.

When a trajectory is selected, motion of the arm with guide tube is only allowed along the trajectory.

| Stopping or preventing robotic arm motion Method |
|---|
| Emergency Stop button pressed |
| End Effector detects force on arm greater than 50N (11 lbs) |
| Dynamic reference base not in view of camera (Trajectory mode only) |
| End Effector not in view of camera (Trajectory mode only) |
| Sensing ring detects a metallic instrument in the guide tube |

If the robot arm is not able to reach to a safe starting location due to its current position, an error message is shown. The message states "The arm cannot move back any further along the current end-effector trajectory. Acknowledging this message enables the arm to move to the selected plan trajectory from its current position". The user may choose to move forward with the planned trajectory because the shorter starting position is acceptable. If the shorter starting position is not acceptable, a new trajectory must be used or the base must be repositioned.

To select a new trajectory, the user clears the selected trajectory and positions the robotic arm using the bracelet to a clear position. The bracelet provides flexibility for the user to move the arm around an obstacle.

To reposition the base, the stabilizers on the casters are disengaged, the station is moved to the desired location and the stabilizers are reengaged. Registration is unaffected because the patient reference (attachment instruments and DRB) has not moved with respect to the patient.

System Software

The system software is responsible for all motion control functions, navigation functions, data storage, network connectivity, user management, case management, and safety functions.

The top navigation bar takes the user through individual screens for each step of the procedure.

The respective tab for each step is highlighted when selected and the corresponding screen displayed. The activities performed under each tab are shown in the table below.

| | System software tabs |
|---|---|
| Tab | Meaning |
| Configure | Surgeon, imaging workflow, and anatomy selection |
| Preplan | Implant system selection and desired anatomical location identification |
| Verify | Navigated instrument verification |
| Image | Loading of patient images used for planning and navigation |
| Plan | Estimation of desired implant location with respect to patient images |
| Navigate | Screw plan with real-time display of navigated instrument and implant (actual plan) with respect to patient images |

System Setup
Power Up

Figure 30:
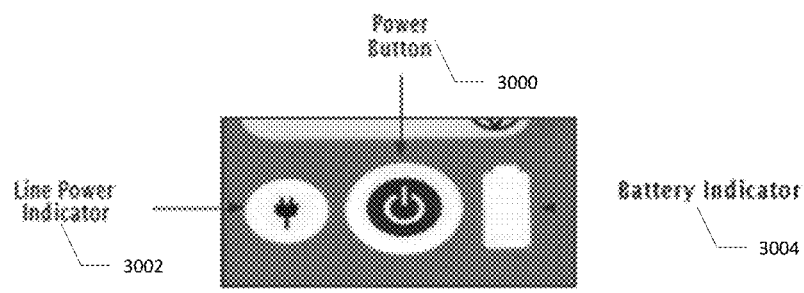
FIG. 30 illustrates a power button, line power indicator and battery indicator.

FIG. 30 illustrates the power button 3000, line power indicator 3002 and battery indicator 3004. Press the Power Button 3000 on the control panel to turn the system on. The Power Button 3000 is illuminated when the system is on.

Undocking and Positioning Camera Stand

Figures 31A, 31B:
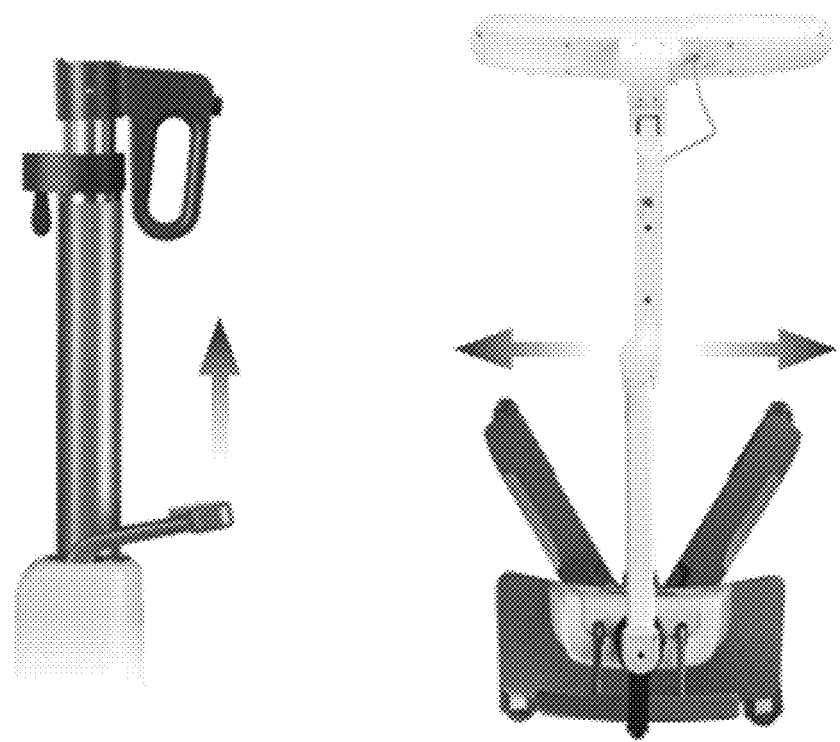
FIGS. 31(a) and 31(b) illustrate a camera stand undocking.

To release the camera stand from the Robotic Base Station, unwrap the cord holding the monitor arm and the camera arm together, and pull up on the release handle located on the camera stand. Once the legs of the camera stand have cleared the base station, they will automatically release and move outward. FIGS. 31(a) and 31(b) illustrates the camera stand undocking. FIG. 31(a) illustrates pulling up on the release handle located on the camera stand. FIG. 31(b) illustrates clearing the legs of the camera stand legs automatically releasing and moving outward.

Unwrap the camera cord from the cord holder and plug into the connector panel on the base station.

Move the camera to the operating room (O.R.) table and engage the wheel brakes by stepping on the lever located on the wheel.

Align the camera to view the surgical field.

Figure 32:
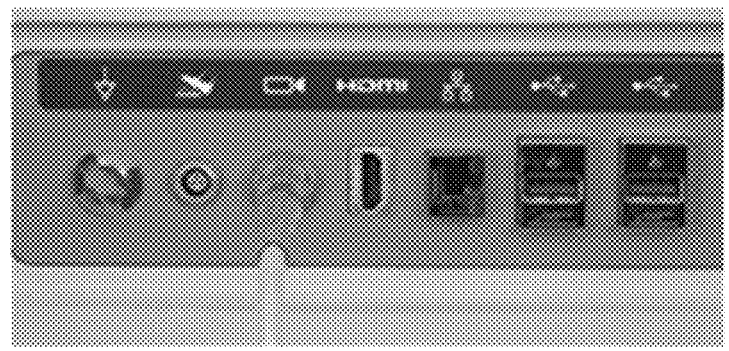
FIG. 32 illustrates the connection of a camera to a connector panel on a base station.
Figure 33:
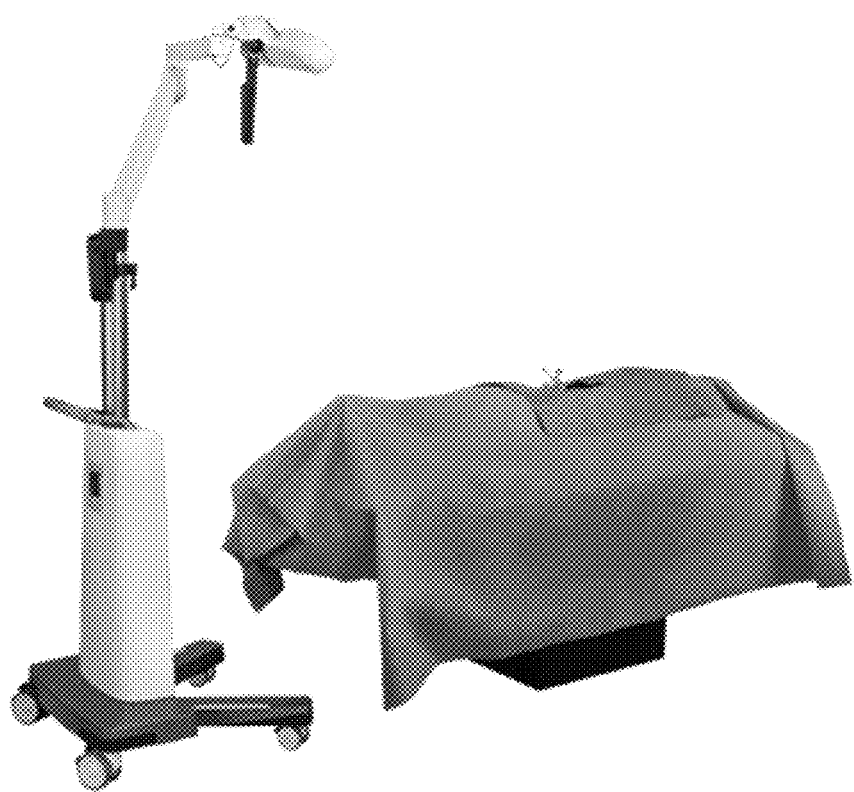
FIG. 33 illustrates a camera positioning.

FIG. 32 illustrates the connection of the camera to the connector panel on the base station. FIG. 33 illustrates the camera positioning.

Figure 34:
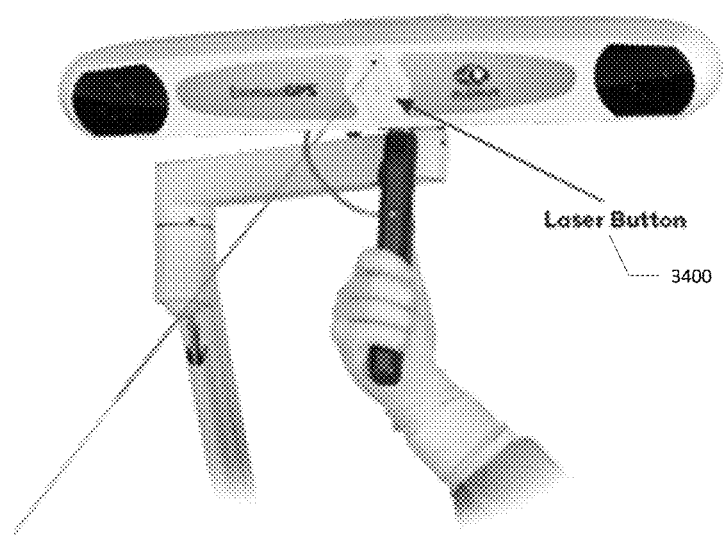
FIG. 34 illustrates pressing a laser button to align the camera.

Press and hold the laser button located on the positioning handle of the camera to activate the camera's alignment laser and adjust the position so the laser points to the center of the surgical field. FIG. 34 illustrates pressing the laser button 3400 to activate a laser which facilitates user alignment of the camera.

Draping

Figure 35:
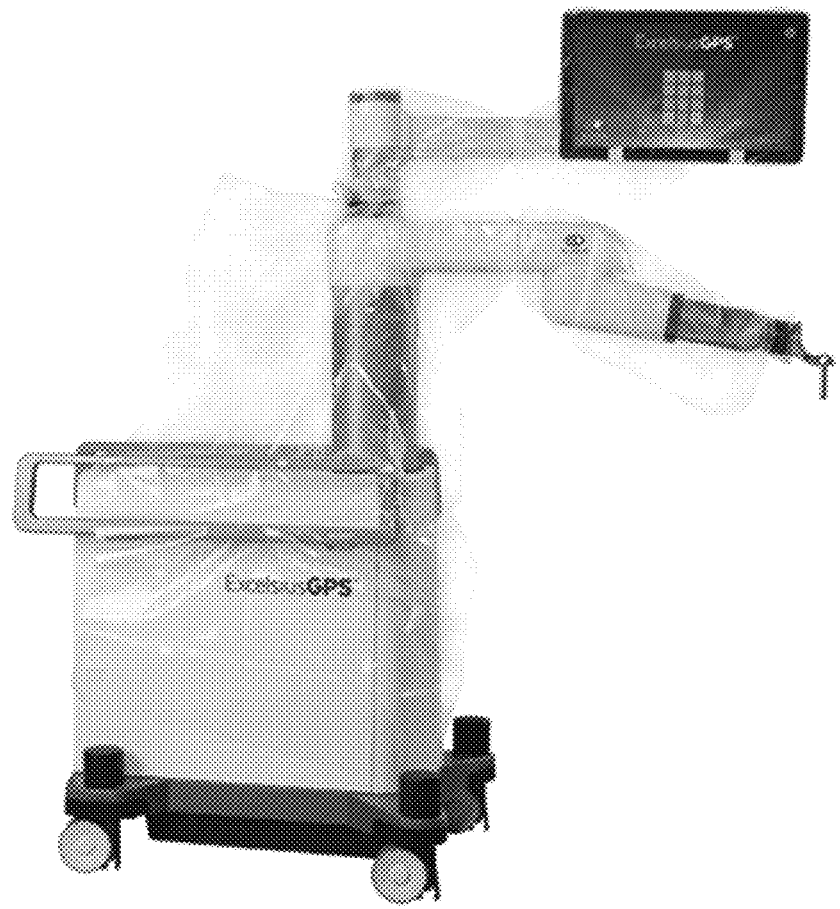
FIG. 35 illustrates a system with a sterile drape.

A special surgical drape is designed for the robotic computer system Robotic Base Station. Drape the robotic arm, monitor and front of the base station, by following the instructions detailed in the package insert provided with the sterile drape. FIG. 35 illustrates the system with a sterile drape.

Positioning the Robotic Base Station

Unwrap the foot pedal from the foot pedal basket and position it on the level ground at a comfortable distance from the operator's feet. The foot pedal is IPX68 rated and is acceptable for use in areas where liquids are likely to be found. Plug the foot pedal cord into the connector panel. The foot pedal allows the arm to move to the active trajectory, similar to the action of the bracelet on the lower arm.

Figure 36:
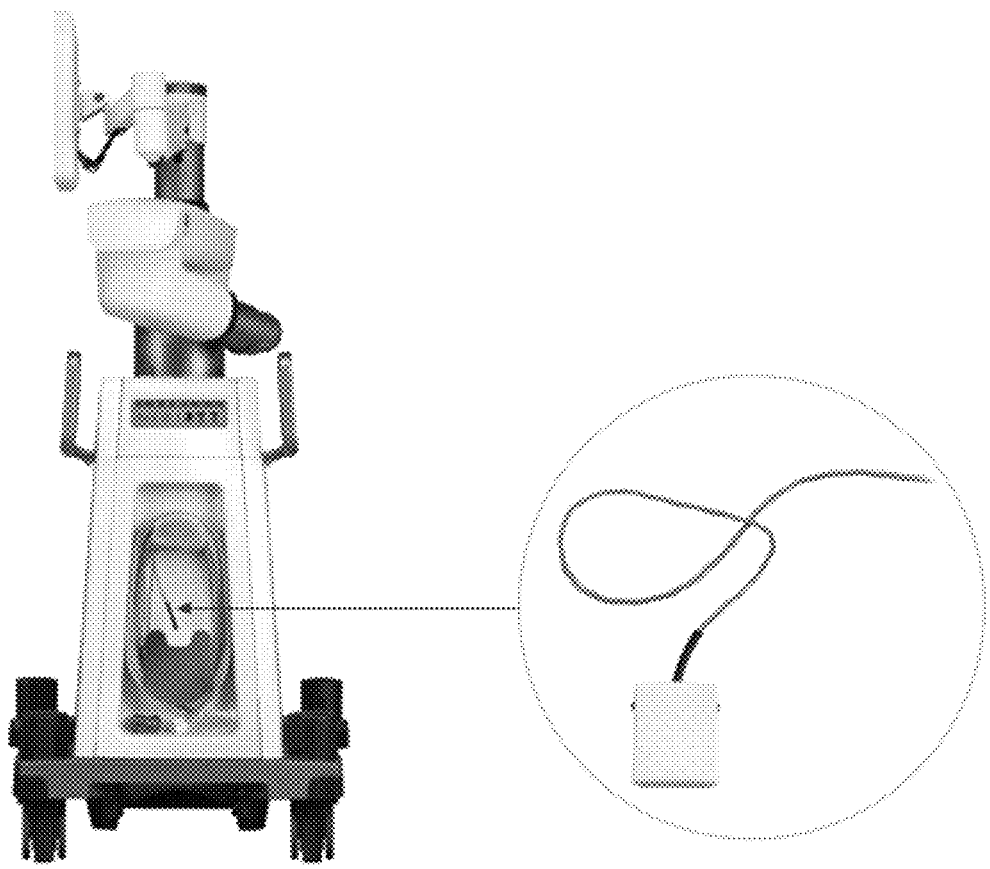
FIG. 36 illustrates a foot pedal cable connection.

Position the Robotic Base Station next to the patient at a comfortable distance from the surgeon. Move the robotic arm, using the bracelet, around the planned trajectories to ensure the arm can reach all locations before engaging the stabilizers. FIG. 36 illustrates the foot pedal cable connection.

Figure 37:
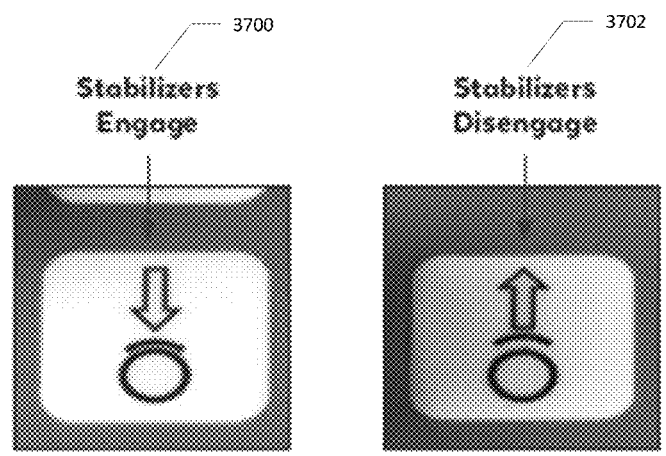
FIG. 37 illustrates buttons which are illuminated when stabilizers engage and stabilizers disengage.

Press the Stabilizers Engage button on the control panel to lower the stabilizers on the casters. The button is illuminated when the stabilizers are engaged. FIG. 37 illustrates the buttons which are illuminated when the stabilizers engage (e.g. responsive to pressing the stabilizers engage button 3700) and stabilizers disengage (e.g. responsive to pressing the stabilizers disengage 3702).

Attaching End Effector to Robotic Arm

The end effector connects to the robotic arm through the interface plate over the custom drape. A magnetic assist helps to position and self-align the end effector.

Figure 38:
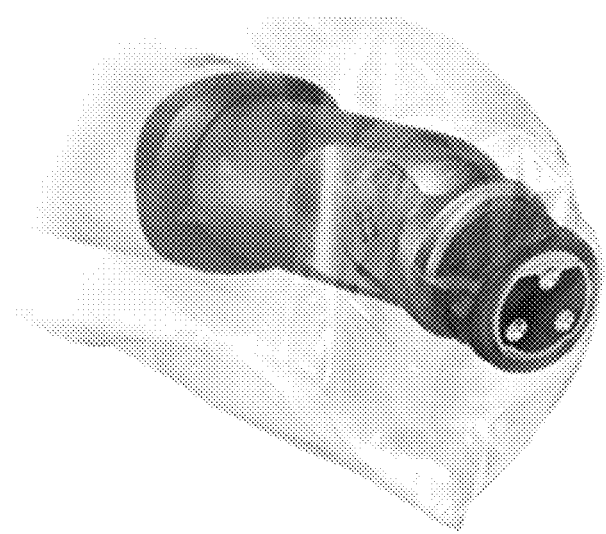
FIG. 38 illustrates the robotic arm interface plate for connection to the end effector.

The end effector is equipped with a drape-friendly clamp that allows it to be removed and reattached up to 3 times during a procedure without damaging the drape. FIG. 38 illustrates the robotic arm interface plate for connection to the end effector.

Figure 39:
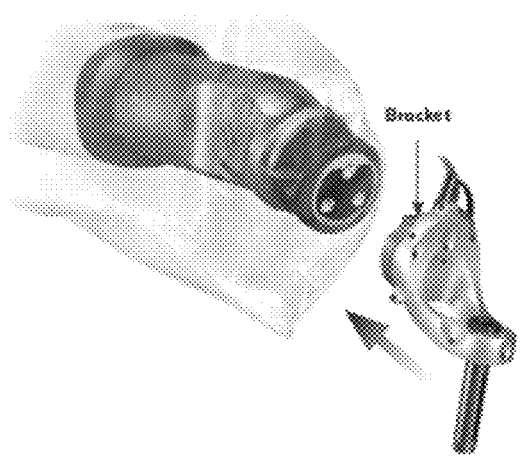
FIG. 39 illustrates opening brackets on an end effector and place the end effector on the interface plate by aligning the V grooves and alignment spheres.

FIG. 39 illustrates opening the brackets on the end effector and place the end effector on the interface plate by aligning the V grooves and alignment spheres.

Figure 40:
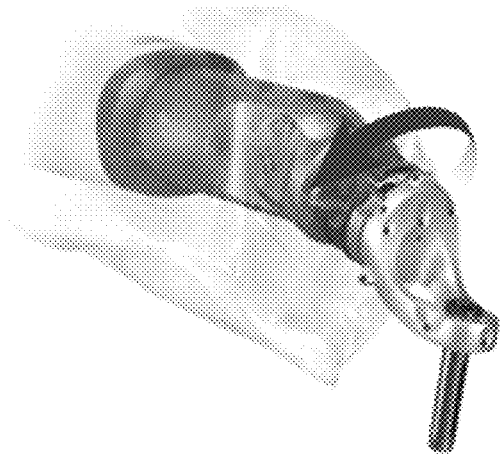
FIG. 40 illustrates squeezing brackets on both sides of an end effector and press the handle down to lock into place.

FIG. 40 illustrates squeezing the brackets on both sides of the end effector and press the handle down to lock into place.

Figure 41:
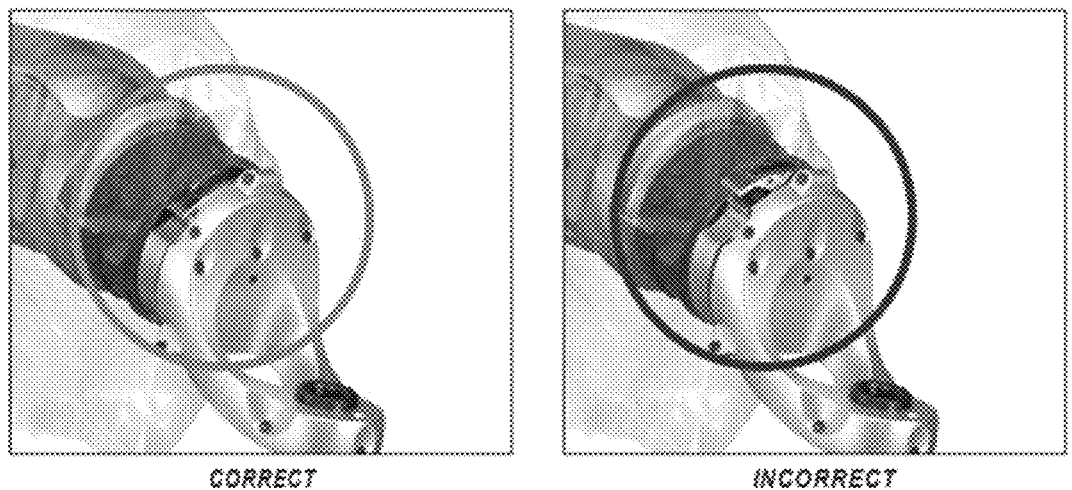
FIG. 41 illustrates a correct and incorrect positioning of a handle down to lock into place.

FIG. 41 illustrates the correct and incorrect positioning of the handle down to lock into place.

Removing the End Effector

Figure 42:
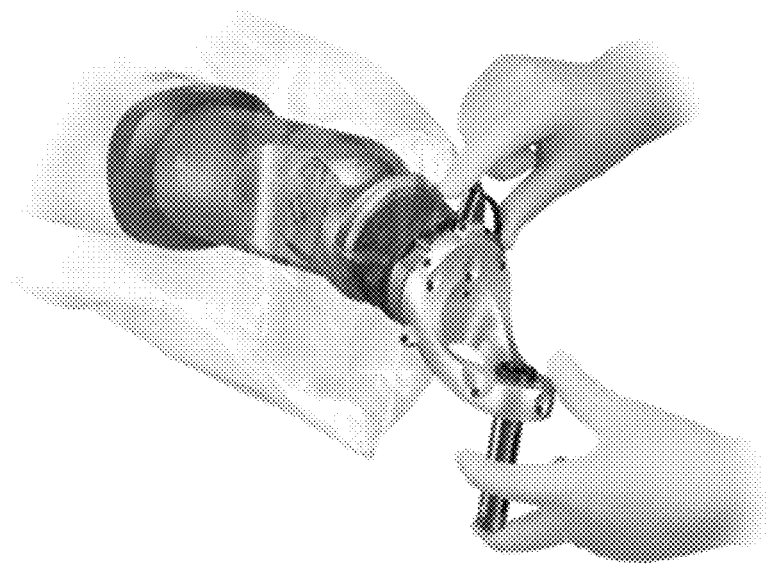
FIG. 42 illustrates a removal of the end effector.

To remove the end-effector from the robotic arm, pull up on the handle to release the spring and side brackets. FIG. 42 illustrates the removal of the end effector.

Surgical Instrument Assembly

Figure 43:
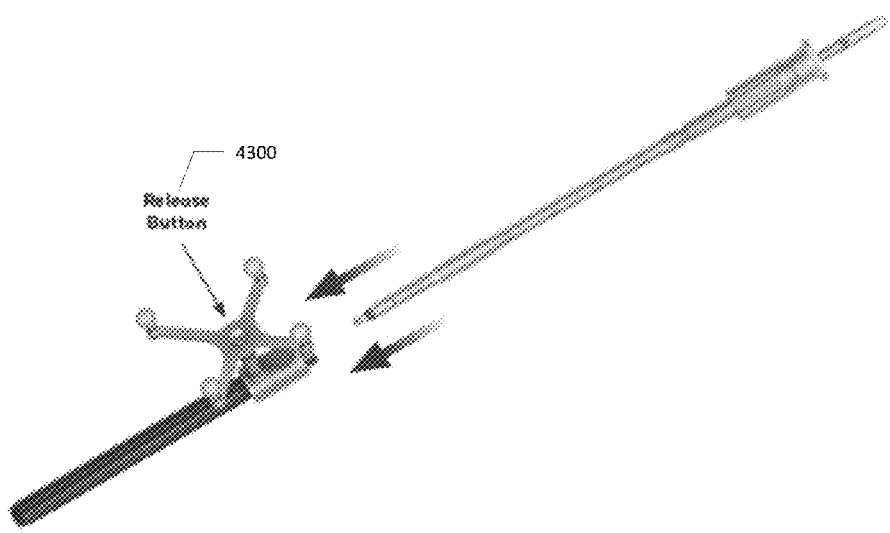
FIG. 43 illustrates inserting an instrument shaft into an array sleeve.

To assemble the surgical instruments for navigation, press the release button on the array sleeve and insert the instrument shaft into the sleeve of the respective instrument array. Slide the shaft through the sleeve until it clicks into place. Gently pull up on the instrument shaft to confirm it is locked. FIG. 43 illustrates inserting the instrument shaft into the array sleeve, and further illustrates a release button 4300 which releases the array.

Figure 44:
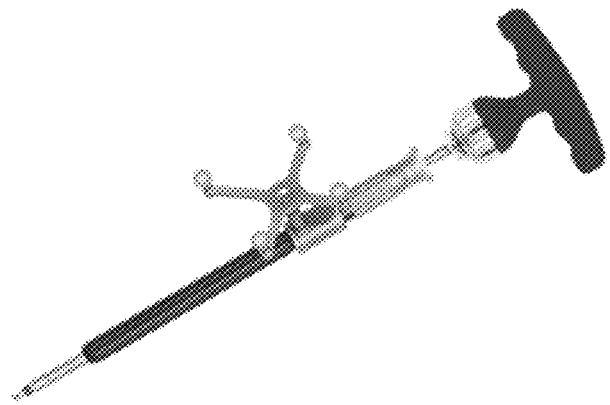
FIG. 44 illustrates a surgical instrument assembly.
Figure 45:
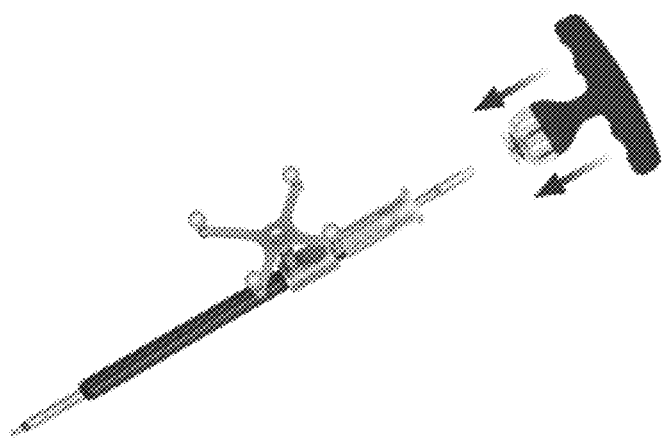
FIG. 45 illustrates attaching a quick connect handle on the proximal end of a shaft of the surgical instrument assembly.

Attach a quick connect handle on the proximal end of the shaft when needed. To remove the instrument from the array, push the release button located on the middle of the array. FIG. 44 illustrates the surgical instrument assembly. FIG. 45 illustrates attaching the quick connect handle on the proximal end of the shaft of the surgical instrument assembly.

Attach the disposable reflective markers to each of the marker posts of each instrument assembly. Ensure that the markers are fully seated on the posts. FIGS. 46(*a*) and 46(*b*) illustrates attaching a reflective marker to one of a plurality of marker posts of the instrument assembly. FIG. 46(*a*) illustrates lowering the reflective marker onto a marker post. FIG. 46(*b*) illustrates the marker fully seated on the post.

Login

To login, type the four-digit pin on the touch screen of the monitor. The four digit pin is provided during system installation and can be changed by contacting Tech Support. FIG. 47 illustrates the login screen displayed on the monitor.

A case encompasses all of the data associated with performing a procedure, including surgeon preferences, medical images, and plans.

After logging in, the SELECT CASE page is displayed on the monitor.

Figure 48:
FIG. 48 illustrates a case management screen displayed on a monitor.

To select an existing case, select the corresponding row from the case list. To start a new case, click the new case icon. Click the right arrows to advance to the next tab. FIG. 48 illustrates the case management screen displayed on the monitor.

Applications

Figure 49:
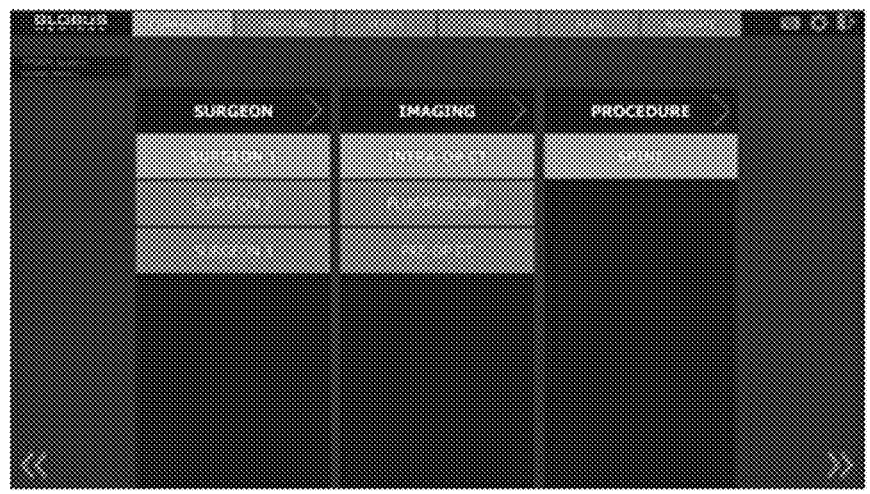
FIG. 49 illustrates a CONFIGURE tab used to display procedure types.

Spine surgical procedures are supported by the robotic computer system. FIG. 49 illustrates the CONFIGURE tab used to display procedure types.

Spine Procedures

Spinal surgical applications supported by the robotic computer system are listed below.

| Supported spine procedures | |
| --- | --- |
| Procedures | Patient Position |
| Posterior Cervical | Prone |
| Posterior Thoracic | Prone |
| Anterolateral Thoracic | Lateral |
| Posterior Lumbar | Prone |
| Lateral Lumbar | Lateral |

Globus spinal implant systems that are compatible with the robotic computer system are listed below.

| Compatible spinal implant systems | |
| --- | --- |
| CREO® | Stabilization System |
| REVERE® | Stabilization System |
| REVOLVE® | Stabilization System |
| ELLIPSE® | Occipito-Cervico-Thoracic Spinal System |
| QUARTEX® | Occipito-Cervico-Thoracic Spinal System |
| SI-LO® | K Sacroiliac Joint Fusion System |

Procedure Setup

Configure Tab

After selecting a case, the CONFIGURE tab is displayed on the monitor.

Using the CONFIGURE tab, select the surgeon, the imaging modality and the procedure type. Click the right arrows to advance to the next tab.

Preplan Tab

Figure 50:
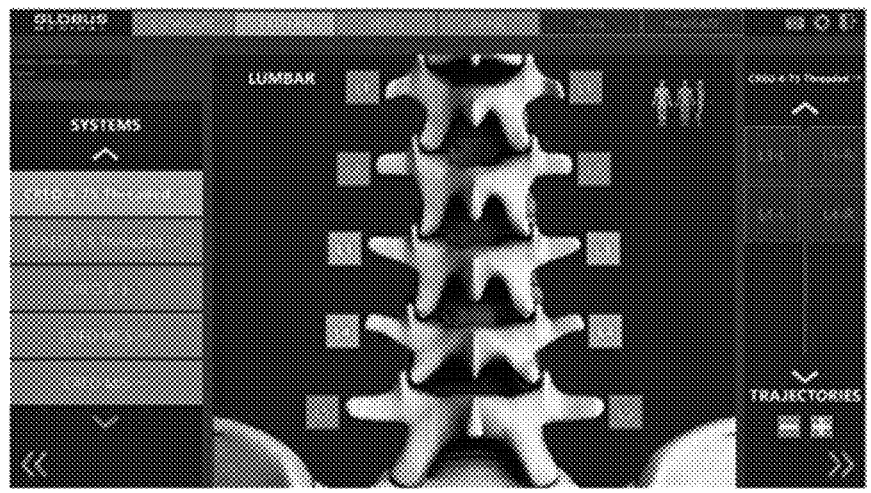
FIG. 50 illustrates a PREPLAN tab displayed on the monitor to select the implant system, desired vertebral level and orientation.

Using the PREPLAN tab, select the implant system, desired vertebral level and orientation, and click the desired implant location on the anatomical model. Click the right arrows to advance to the next tab. FIG. 50 illustrates the PREPLAN tab displayed on the monitor to select the implant system, desired vertebral level and orientation.

Verify Tab

Figure 51:
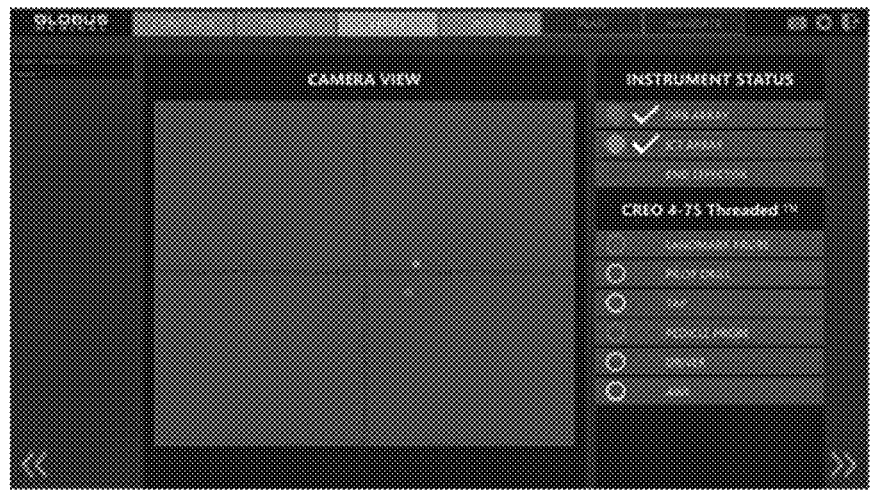
FIG. 51 illustrates a VERIFY tab displaying navigation details including visibility, location and verification status of the instruments selected on the PREPLAN tab.

FIG. 51 illustrates the VERIFY tab displaying navigation details including visibility, location and verification status of the instruments selected on the PREPLAN tab. Verification is used to ensure all instruments are accurate and have not been damaged during handling and sterilization. The operator must assemble all instruments prior to verification (see Surgical Instrument Assembly).

The VERIFY tab shows CAMERA VIEW and INSTRUMENT STATUS.

CAMERA VIEW is a real-time view from the perspective of the camera with color circles indicating instrument location. A solid colored circle indicates that the instrument is visible by the camera, while a hollow circle indicates that it is not visible. The colored circle grows larger as the instrument is moved closer to the physical camera and smaller as it moves away from the camera. The ideal distance from the camera is approximately 2 meters or 6 feet.

INSTRUMENT STATUS lists each instrument and its verification status, with corresponding color circles to identify each instrument. The verification status is symbolized by a checkmark if verification is successful and an X-mark if the verification failed. When no icon appears, the instrument is not verified.

Instrument Verification

Figure 52:
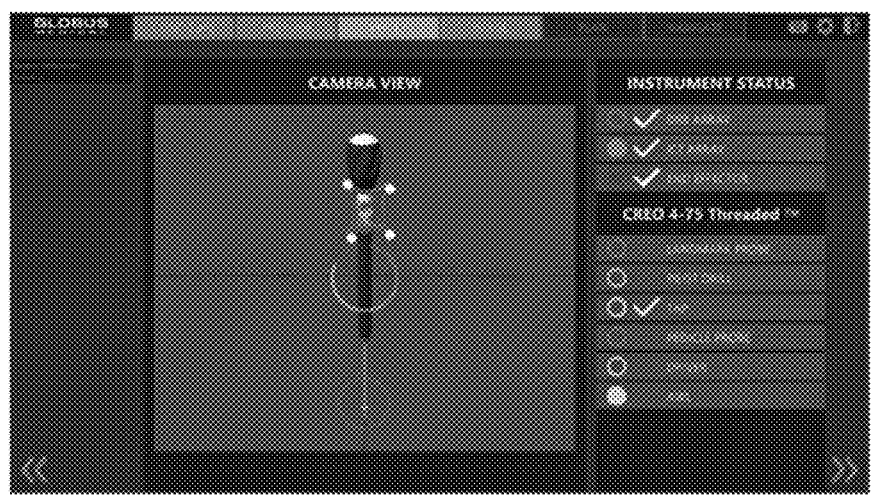
FIG. 52 illustrates a pop-up screen appearing on the VERIFY tab to indicate the verification progress.
Figure 53:
FIG. 53 illustrates verification divots located on the end effector.

Verify each instrument as follows: place the tip of the instrument to be verified into verification divots located on the end-effector and on any other instrument array for convenience; ensure both instruments are visible and held steady; and use a pop-up screen appearing on the VERIFY tab to indicate the verification progress. FIG. 52 illustrates the pop-up screen appearing on the VERIFY tab to indicate the verification progress. FIG. 53 illustrates the verification divot 1712 which between the hand grip 1704 and the array 1700.

Once verification is complete, verification status is indicated on the screen with the tip error displayed in mm. If verification has failed (red crossed circle), verification must be repeated until it is successful (green circle).

Figure 54:
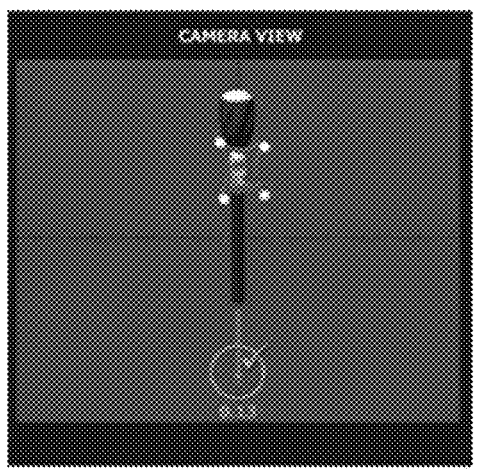
FIG. 54 illustrates a green circle indicating a successful verification.
Figure 55:
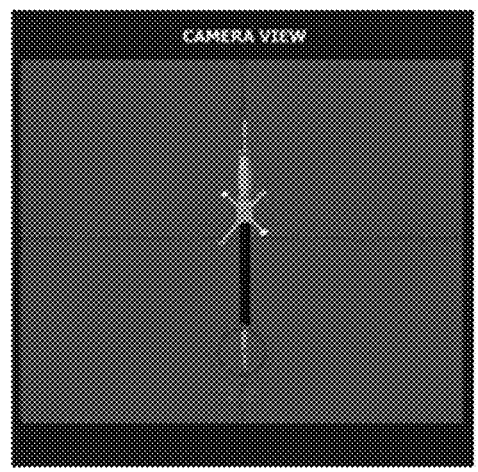
FIG. 55 illustrates a red crossed circle indicating a failed verification.

When all instruments are successfully verified, advance to the next tab. FIG. 54 illustrates the green circle indicating a successful verification. FIG. 55 illustrates the red crossed circle indicating a failed verification.

Patient Attachment Instruments

Patient attachment instruments are secured to rigid bony anatomy neighboring the surgical site. Select the desired instrument. Patient attachment instruments should be placed no more than 185 mm from the center of the surgical site to maintain accuracy.

Bone clamps are clamped onto anatomical structures such as the spinous process, iliac crest, long bone, or any rigid bony structure that can be safely clamped.

Quattro spikes are inserted into the iliac crest or a long bone.

Rod attachments are secured to an existing spinal rod, 4.5 mm to 6.35 mm in diameter.

Refer to the table below for recommended anatomic locations for the various patient attachment instruments.

Patient attachment instruments - recommended anatomic locations

| Spine Procedures | Patient Position | Patient Attachment Instrument | Recommended Patient Attachment Instrument Location |
|---|---|---|---|
| Posterior Cervical | Prone | Bone Clamp Rod Attachment | Spinous Process C2-T3 Existing Rod |
| Posterior Thoracic | Prone | Bone Clamp Rod Attachment | Spinous Process T1-L1 Existing Rod |
| Anterolateral Thoracic | Lateral | Bone Clamp | Spinous Process T1-L1 |
| Posterior Lumbar | Prone | Quattro Spike Low Profile Quattro Spike Bone Clamp Rod Attachment | Iliac Crest Iliac Crest  Spinous Process T12-L5 Existing Rod |
| Lateral Lumbar | Lateral | Quattro Spike Low Profile Quattro Spike Bone Clamp Rod Attachment | Iliac Crest Iliac Crest  Spinous Process T12-L5 Existing Rod |

Dynamic Reference Base Insertion

Position the compression clamp on the Dynamic Reference Base (DRB) over the patient attachment instrument and tighten the knob. If needed, the clamp driver can be used to further tighten the knob.

Position the reflective markers on the DRB in the direction of the camera. Care should be taken with initial placement of the patient reference instrument as to not interfere with the surgical procedure.

Figure 56:
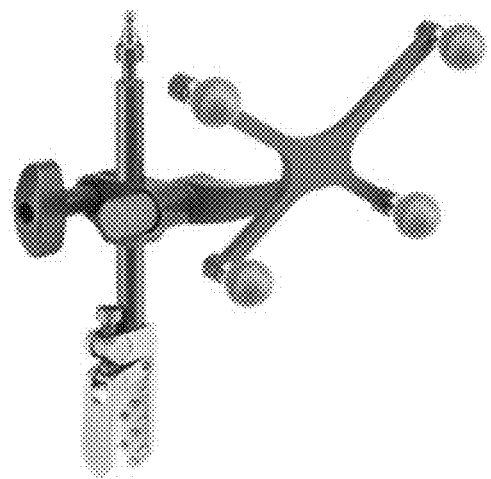
FIG. 56 illustrates securing a Dynamic Reference Base to a patient attachment instrument.
Figure 57:
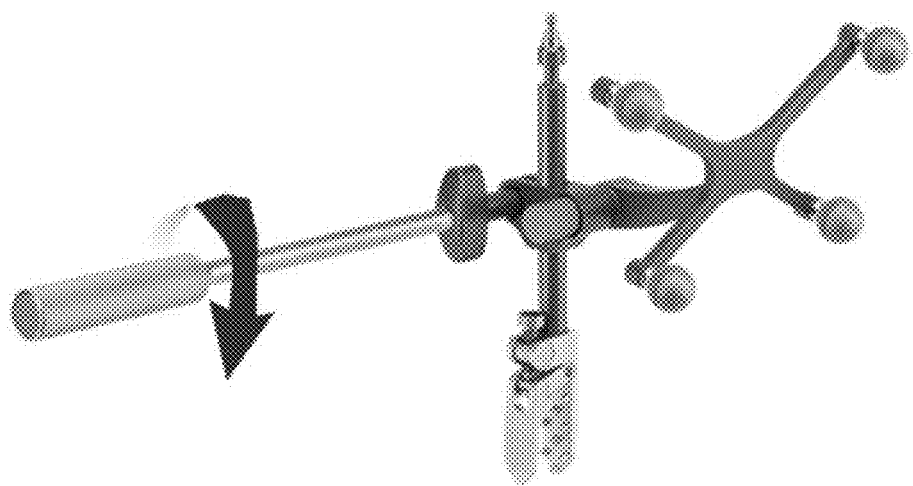
FIG. 57 illustrates using a clamp driver to a Dynamic Reference Base.

Following navigation, the patient attachment instrument is removed. FIG. 56 illustrates securing a Dynamic Reference Base to a patient attachment instrument. FIG. 57 illustrates using a clamp driver to the Dynamic Reference Base.

Surveillance Marker

The surveillance marker is inserted into rigid bony anatomy to track the relative distance to the DRB, to identify unwanted shifts in the DRB during the procedure.

Surveillance markers are inserted into the iliac crest or long bone, or may be attached to the spinous process using a bone clamp. Verify that the clamp is rigidly secured. The surveillance marker should be placed no more than 185 mm from the Dynamic Reference Base. Refer to the table below for recommended anatomic locations.

Surveillance marker - recommended anatomic locations

| Spine Procedures | Patient Position | Patient Attachment Instrument | Recommended Patient Attachment Instrument Location |
|---|---|---|---|
| Posterior Cervical | Prone | Bone Clamp | Spinous Process C2-T3 |
| Posterior Thoracic | Prone | Single Bone Clamp | Iliac Crest Spinous Process T1-L1 |
| Anterolateral Thoracic | Lateral | Bone Clamp | Spinous Process T1-L1 |
| Posterior Lumbar | Prone | Single Bone Clamp | Iliac Crest Spinous Process T12-L5 |
| Lateral Lumbar | Lateral | Single Bone Clamp | Iliac Crest Spinous Process T12-L5 |

Figure 58:
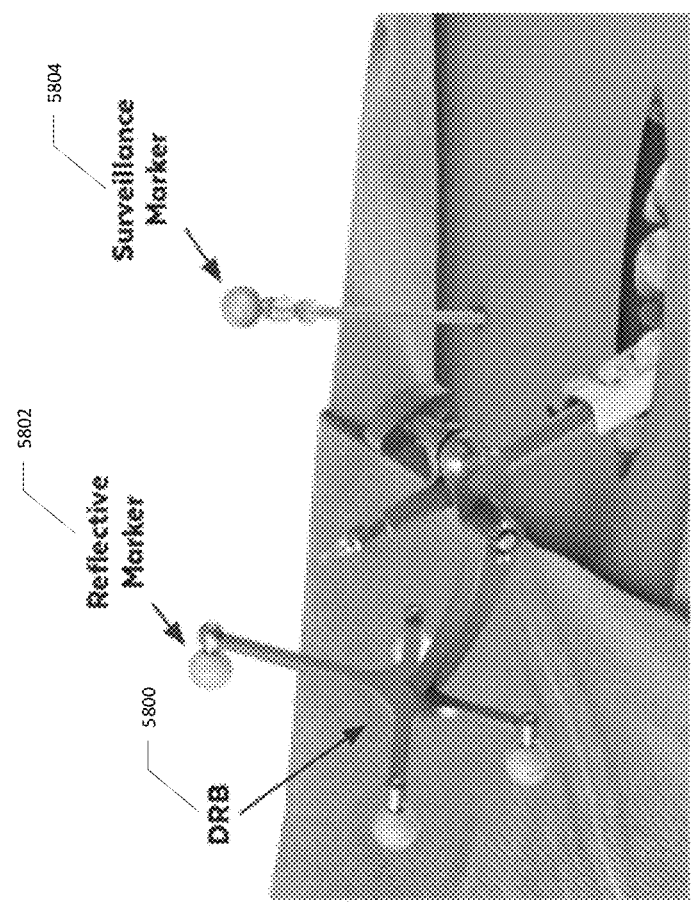
FIG. 58 illustrates the placement of a Dynamic Reference Base and a surveillance marker.

Attach a disposable reflective marker to the marker post of the surveillance marker. Attach the impaction cap, designed to fit over the reflective marker sphere, onto the surveillance marker. Insert the surveillance marker into rigid bony anatomy near the surgical site, and gently impact with a mallet. Remove the impaction cap. Remove the reflective marker prior to using the removal tool. FIG. 58 illustrates the placement of the Dynamic Reference Base (DRB) 5800 and the surveillance marker 5804. The DRB 5800 includes reflective markers 5802.

To use a bone clamp with the marker, attach a disposable marker onto the tip of the bone clamp. Use the clamp driver to secure the bone clamp. Verify that the clamp is rigidly secured.

Removal

Figure 59:
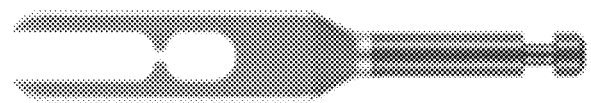
FIG. 59 illustrates a quattro spike.
Figure 60:
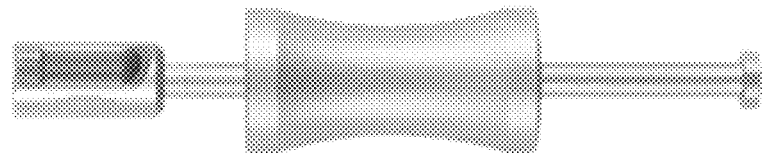
FIG. 60 illustrates a quattro spike removal tool.
Figure 61:
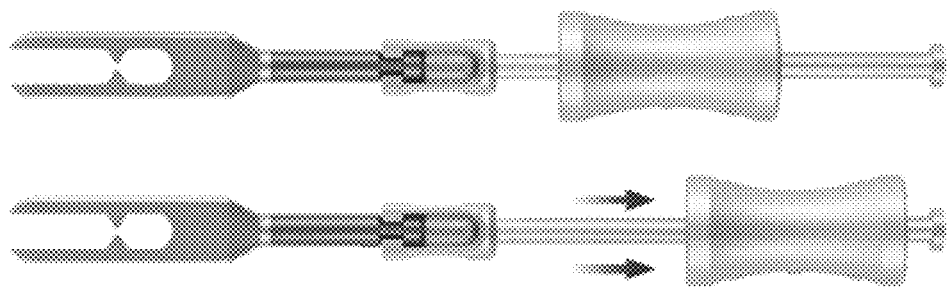
FIG. 61 illustrates removing a quattro spike with a removal tool.

The quattro spikes and surveillance marker are removed from bony anatomy manually or using the removal tool. The bone clamp is removed by loosening the clamp with the clamp driver, attaching the removal tool and lifting up the bone clamp. FIG. 59 illustrates a quattro spike. FIG. 60 illustrates a quattro spike removal tool. FIG. 61 illustrates removing a quattro spike with a removal tool.

Intra-Operative CT Imaging Workflow

Image Tab

Intra-Op Ct Registration Fixture Setup

Figure 62:
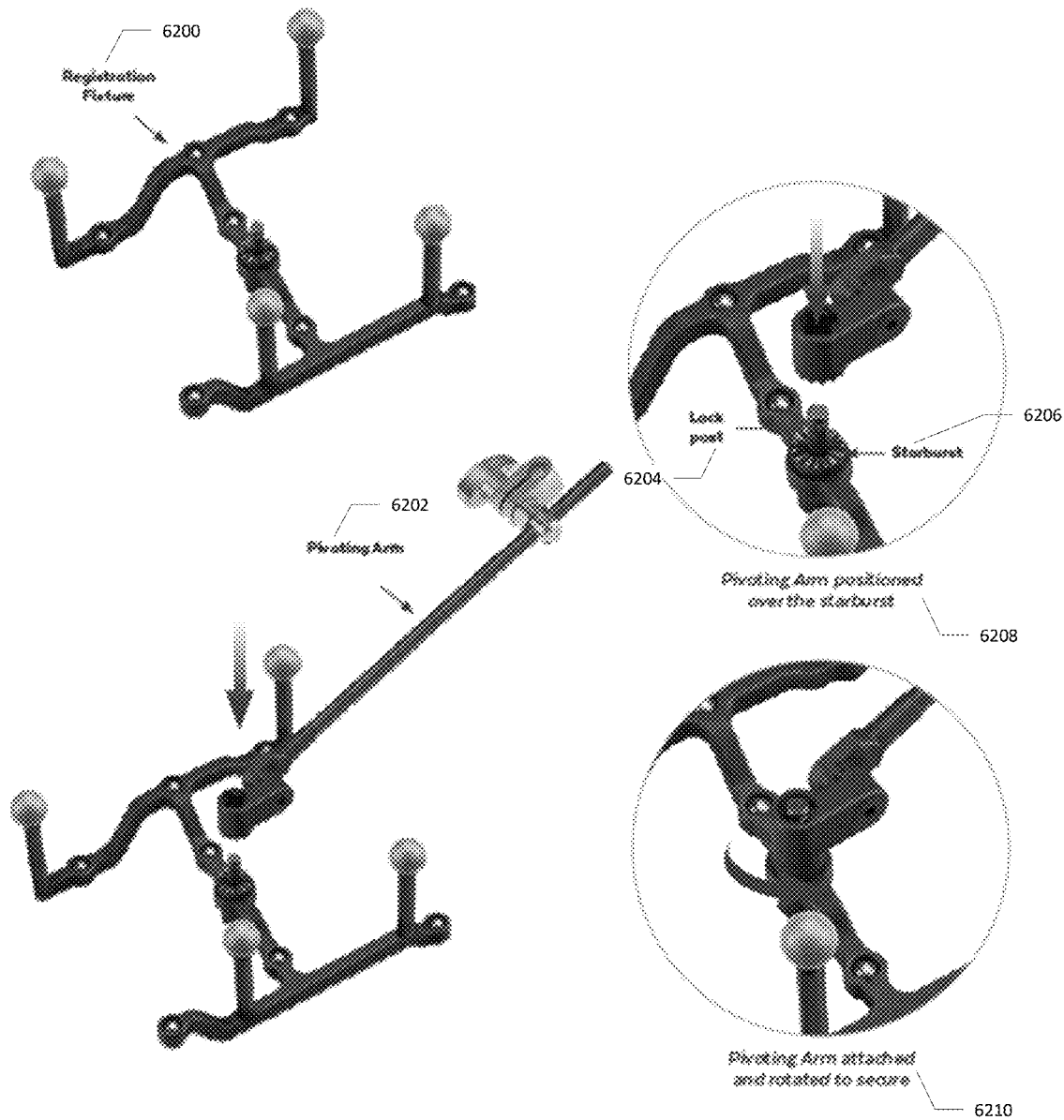
FIG. 62 illustrates attaching a registration fixture to a pivoting arm.

FIG. 62 illustrates attaching a registration fixture 6200 to a pivoting arm 6202. Place the pivoting arm starburst 6206 over the starburst 6206 on the registration fixture 6200 and rotate 90° to secure. Referring to the enlarged view 6208 of the pivoting arm 6202 positioned over the starburst 6206, push the lock post 6204 from the bottom and rotate the arm 90° until the pin in the lock post 6204 is seated to secure the fixture. Enlarged view 6210 shows the pivoting arm 6202 attached and rotated to become secured to the registration fixture 6200.

Figure 63:
FIG. 63 illustrates a registration fixture connecting to a patient attachment instrument.

FIG. 63 illustrates a registration fixture connecting to a patient attachment instrument. Position the fixture on the patient attachment instrument post and tighten the compression clamp knob. If needed, the clamp driver can be used to further tighten the knob.

To release the pivoting arm, push the lock post on the fixture, rotate the pivoting arm 90° and pull up.

The Intra-op CT Registration Fixture has six degrees of freedom and can be moved by adjusting one of the three joints so that it is stable and hovering over the surgical site. Only the metal fiducials embedded in the fixture need to be in the 3D scan (not the reflective markers). It is important that the Intra-op CT Registration Fixture does not move between the image acquisition and performing an anatomical landmark check.

Loading the Image

The IMAGE tab shows the steps needed to load a CT scan image. The image can be loaded from a USB drive or hard drive. If the image is transferred via the Ethernet, it automatically appears on the hard drive when the transfer is complete.

To view images on a USB drive, insert the USB drive into the USB port on the connector panel. To load an image, select the hard drive or USB drive icon and select the desired patient image. Click the right arrows to load the patient images and advance to the next tab.

Manual Registration

Figure 64:
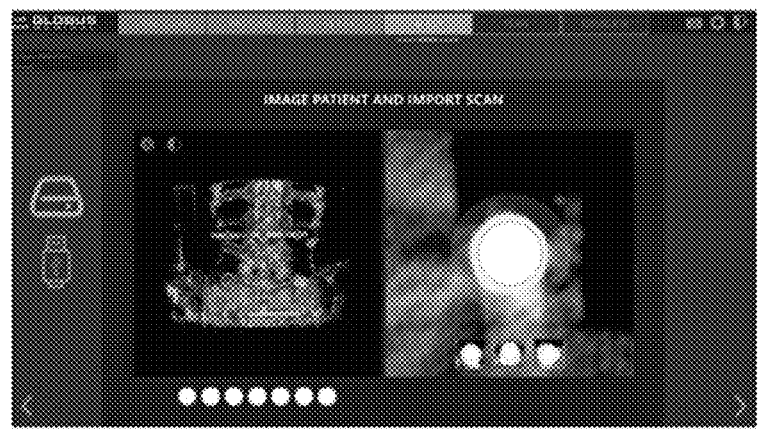
FIG. 64 illustrates a registered fiducial.

Automatic registration is performed when loading images. FIG. 64 illustrates a registered fiducial. If this step fails, the manual registration screen will be shown to allow manual registration as described below.

The image on the left panel of the registration screen is a full scan with a depiction of the intra-op CT.

The registration fixture and the seven fiducials should be visible below the image. Fiducials that are not registered need to be adjusted by the operator. On the screen, select a fiducial that is not registered; that image will appear on the right. Move the blue circle on the screen until it surrounds the white fiducial marker. The three small boxes at the bottom of the right panel show the x, y and z direction of the fiducial and all must be adjusted until the blue circle is centered. Ensure that all seven fiducials are properly identified by viewing the 3D model of the intra-op registration fixture. A fiducial may be deleted by selecting the delete icon on the right panel. Click the right arrows to confirm that the fiducials have been properly identified before proceeding to the next step.

Landmark Check

After registration has been completed, a landmark check should be performed to ensure that the registration was calculated successfully. Using the verification probe, touch an anatomical landmark or a fiducial on the registration fixture and verify that the corresponding location is shown on the system monitor. Repeat this process using 2-3 landmarks.

Removing Registration Fixture

Carefully remove the Intra-op CT Registration Fixture. Ensure the patient attachment instrument does not move.

Intra-Operative CT Imaging Workflow

Plan Tab

Figure 65:
FIG. 65 illustrates a PLAN tab allowing a user to plan all screw trajectories on a patient image.

FIG. 65 illustrates the PLAN tab allowing the user to plan all screw trajectories on the patient image. Screws are preloaded on the right hand side of the screen, based on selections made in the PREPLAN tab.

To add a screw onto the planning page, drag and drop the appropriate screw label on the image at the desired slice.

The active screw plan is shown in green. Details of the active screw plan are shown on the lower right of the screen, including screw family, diameter, and length. Click on the right arrows to advance to the next tab once plans are complete for all screws.

| Adjusting screw trajectory | |
| --- | --- |
| Screw Body | Press and move along screen to translate the screw along the current plane of the anatomy |
| Screw Head | Press and move to change the angle of the trajectory, pivoting along the tip of the screw |
| Screw Tip | Press and move to change the angle of the trajectory, pivoting along the head of the screw |
| Scroll Bar | The scroll bar is the dial control located above the head of the screw. Press the scroll bar and move to rotate the anatomy 360° about the screw. |

| Adjusting screw size | |
| --- | --- |
| Screw Tip | Press and move longitudinally to automatically adjust the length of the screw to available screw sizes |
| Screw Diameter | Press the screw diameter button located on the right hand side of the screen to select other options available with the selected implant set |
| Screw Length | Press the screw length button located on the right hand side of the screen to select other options available with the selected implant set |

Intra-Operative CT Imaging Workflow Planning Operations

Figure 80:
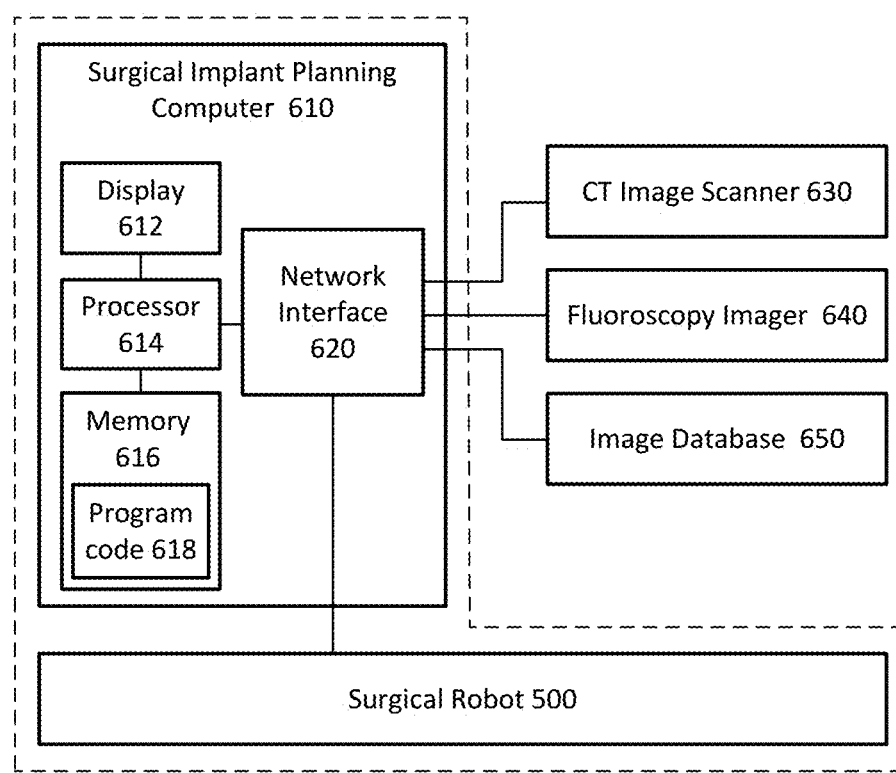
FIG. 80 illustrates a block diagram of a surgical system that includes a surgical implant planning computer which may be separate from and operationally connected to the robot or incorporated therein.

FIG. 80 illustrates a block diagram of a surgical system 600 that includes a surgical implant planning computer 610 which may be separate from and operationally connected to the robot 500 or at least partially incorporated therein. Alternatively, at least a portion of operations disclosed herein for the surgical implant planning computer 610 may be performed by components of the robot 500 such as by the computer subsystem 520.

Referring to FIG. 80, the surgical implant planning computer 610 includes a display 612, at least one processor circuit 614 (also referred to as a processor for brevity), at least one memory circuit 616 (also referred to as a memory for brevity) containing computer readable program code 618, and at least one network interface 620 (also referred to as a network interface for brevity). The network interface 620 can be configured to connect to a CT image scanner 630, a fluoroscopy image scanner 640, an image database 650 of medical images, components of the surgical robot 500, the marker tracking camera 570, and/or other electronic equipment.

When the surgical implant planning computer 610 is at least partially integrated within the surgical robot 500, the display 612 may correspond to the display 524 and/or the tablet 590, the network interface 620 may correspond to the platform network interface 512, and the processor 614 may correspond to the computer 522.

The processor 614 may include one or more data processing circuits, such as a general purpose and/or special purpose processor, e.g., microprocessor and/or digital signal processor. The processor 614 is configured to execute the computer readable program code 618 in the memory 616 to perform operations, which may include some or all of the operations described herein as being performed by a surgical implant planning computer. FIGS. 81 through 87 illustrates various operations that can be performed by the processor 614 in accordance with some embodiments of the present disclosure.

Figure 81:
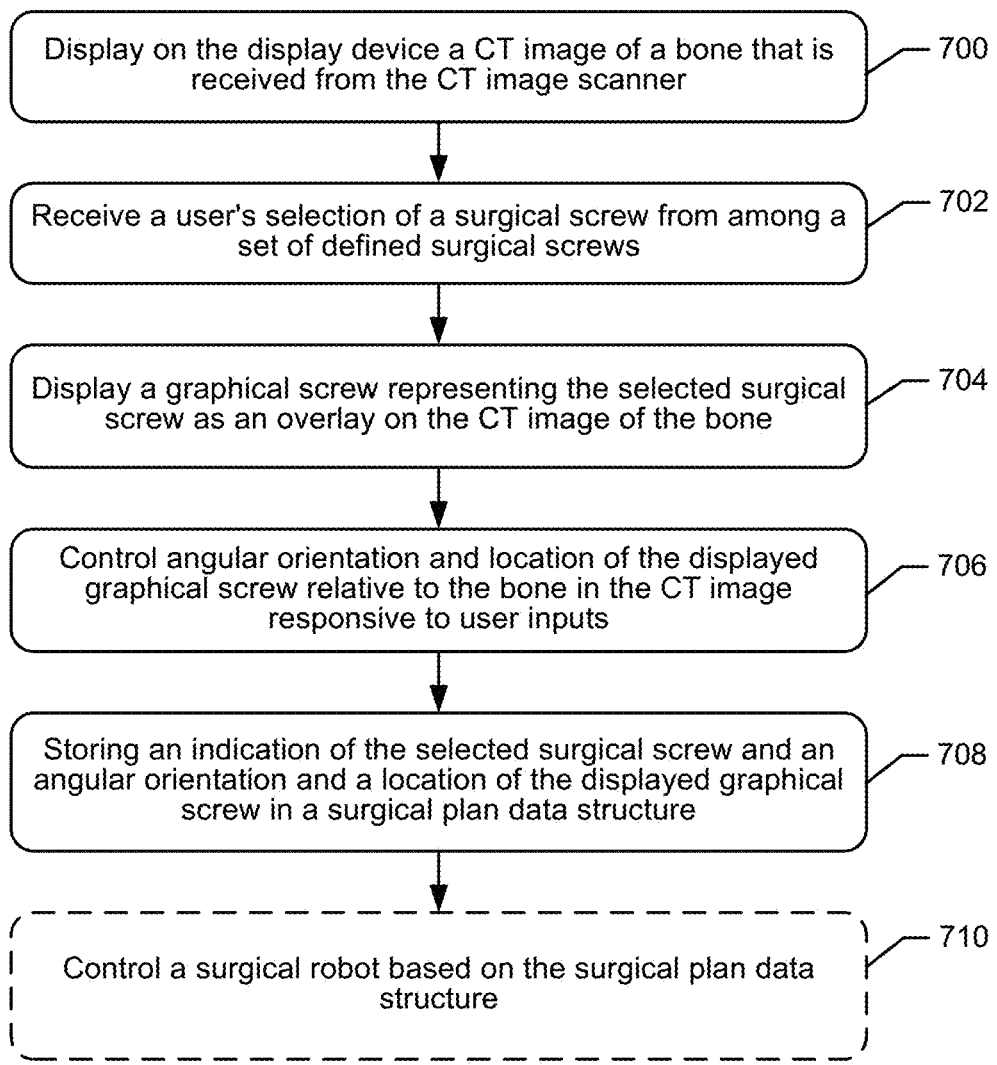
FIGS. 81-87 are flowcharts of operations that may be performed by a surgical implant planning computer which is configured according to embodiments.
Figure 82:
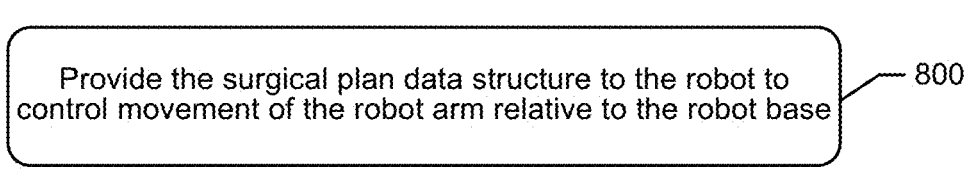

Referring to FIGS. 80 and 81, the processor 614 displays 700 on the display device a CT image of a bone that is received from the CT image scanner 630 through the network interface 620. The processor 614 receives 702 a user's selection of a surgical screw from among a set of defined surgical screws, such as by a user touch selecting user-selectable indicia shown through a touch sensitive screen overlay on the display 612. The processor 614 displays 704 a graphical screw representing the selected surgical screw as an overlay on the CT image of the bone.

The processor 614 controls 706 angular orientation and location of the displayed graphical screw relative to the bone in the CT image responsive to receipt of user inputs, which may be provided by the user touch selecting and/or touch dragging a finger on the display 614 and/or via another user interface, such as a touchpad, joystick, dials, etc. The processor 614 stores 708 an indication of the selected surgical screw and an angular orientation and a location of the displayed graphical screw in a surgical plan data structure, e.g., within memory 616, responsive to receipt of a defined user input, such as a user selecting a displayed indicia for providing a keyboard input. As will be described in further detail below, the processor 614 may control 710 the robot 500 based on the surgical plan data structure to move the robot arm relative to a patient.

The angular orientation and the location that is stored 708 in the surgical plan data structure may be configured to indicate the angular orientation and the location of the displayed graphical screw relative to an angular orientation and a location of the bone in the CT image. The operations to display 704 the graphical screw representing the selected surgical screw as an overlay on the CT image of the bone, can include determining a trajectory along an axis of the graphical screw, and displaying a trajectory line that extends from adjacent to a tip of the graphical screw and along the trajectory to facilitate a user visually orienting and positioning the graphical screw relative to a desired insertion location on the bone.

The operations to control 706 angular orientation and location of the displayed graphical screw relative to the bone in the CT image responsive to receipt of user inputs, can include translating a location of the displayed graphical screw responsive to determining that the user has pressed on a touch-sensitive screen of the display device 612 over a screw body of the graphical screw while moving location of the user's continued pressing along the touch-sensitive screen. The operations can further include angularly pivoting the displayed graphical screw responsive to determining that the user has pressed on the touch-sensitive screen over a screw head and/or tip of the graphical screw while moving location of the user's continued pressing along the touch-sensitive screen.

Alternatively or additionally, the operations to control 706 angular orientation and location of the displayed graphical screw relative to the bone in the CT image responsive to receipt of user inputs, can include selecting a length of the displayed graphical screw from among a set of defined lengths for surgical screws responsive to determining that the user has pressed on a touch-sensitive screen of the display device over a screw tip or a screw head of the graphical screw while moving location of the user's continued pressing along the touch-sensitive screen a measured distance. The selected length of the surgical screw is then stored 708 in the surgical plan data structure.

The operations to control 706 orientation and location of the displayed graphical screw relative to the bone in the CT image responsive to receipt of user inputs, can include modifying a size and/or a rotational angle of the displayed graphical screw on the CT image responsive to tracking motion of a user's hand relative to an input device, such as by tracking motion of the user's finger on a touch sensitive screen overlay on the display 612, on a touchpad, etc.

Intra-Operative CT Imaging Workflow

Navigate Tab

Figure 66:
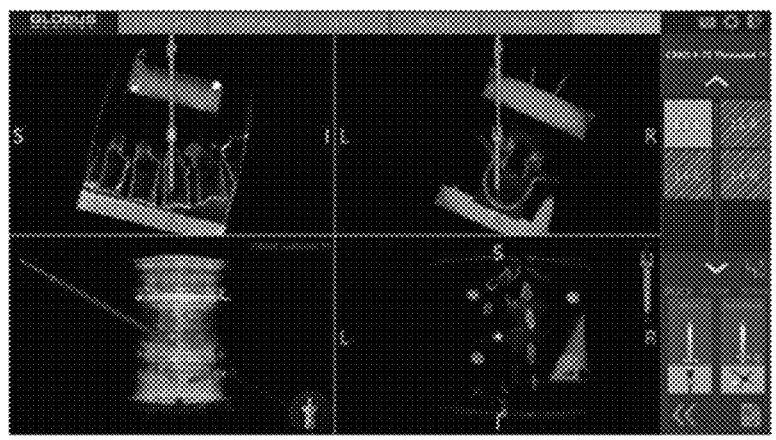
FIG. 66 illustrates a NAVIGATE tab allowing a user to visualize a navigated instrument trajectory and a planned trajectory with respect to patient anatomy.
Figure 66:
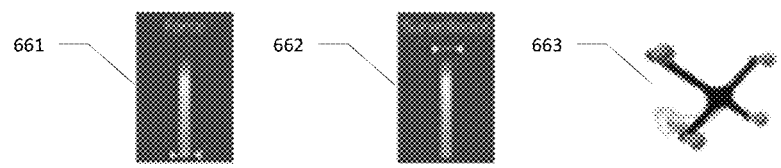

FIG. 66 illustrates the NAVIGATE tab allowing the user to visualize the navigated instrument trajectory and the planned trajectory with respect to patient anatomy.

The robotic arm precisely aligns the end-effector to the planned trajectory. Select the desired screw label on the right of the screen. The screw plan is active when the screw label is highlighted and the robotic arm can be moved by the bracelet or pressing the foot pedal. The robotic arm first moves up in order to clear obstacles in the surgical field and then down along the trajectory. Once on the trajectory, the robotic arm can move up/down along the trajectory but does not move off of the trajectory unless the screw plan is deselected.

The real-time instrument/implant trajectory is displayed on the patient images along with the planned screw, allowing the user to confirm the desired trajectory. If the real-time trajectory is not acceptable, the user can return to the PLAN tab to select another trajectory. If the real-time trajectory is acceptable, the user inserts the screw according to the instrument's current trajectory to the desired depth.

GPS instruments are displayed as they are advanced through the end-effector. While navigating the instruments, periodically observe the monitor and surgical site to ensure consistency between tactile and navigation feedback. Non-navigated metallic Globus instruments may be used through the guide tube while it is stationary for surgical applications unrelated to screw placement.

Monitor the surveillance marker during the procedure. If the surveillance marker indicates significant movement of the DRB, perform an anatomical landmark check. If the landmark check is satisfactory, re-register the surveillance marker. If the landmark check fails, re-register the patient.

There are multiple navigation tab icons. Referring to FIG. 66, the force gauge 661 indicates the force exerted on the end-effector. The image of the instrument at the bottom of the force gauge shows the active instrument in the end-effector or the end-effector image if no instrument is inserted. The surveillance marker error gauge 662 indicates the distance that the patient reference has moved in relation to the surveillance marker. The full range of the scale is 2 mm. The DRB icon 663 indicates dynamic reference base visibility. If the DRB is visible by the camera, the background is green. If the DRB is not visible by the camera, the background is red.

Intra-Operative CT Imaging Workflow Navigation Operations

As explained above, the surgical implant planning computer 610 can control 710 operations of the surgical robot 500. Referring to the operational embodiment of FIG. 82, the processor 614 of the surgical implant planning computer 610 can control 710 the robot 500 by providing 800 the surgical plan data structure to the robot 500 to control movement of the robot arm relative to the robot base.

Figure 83:
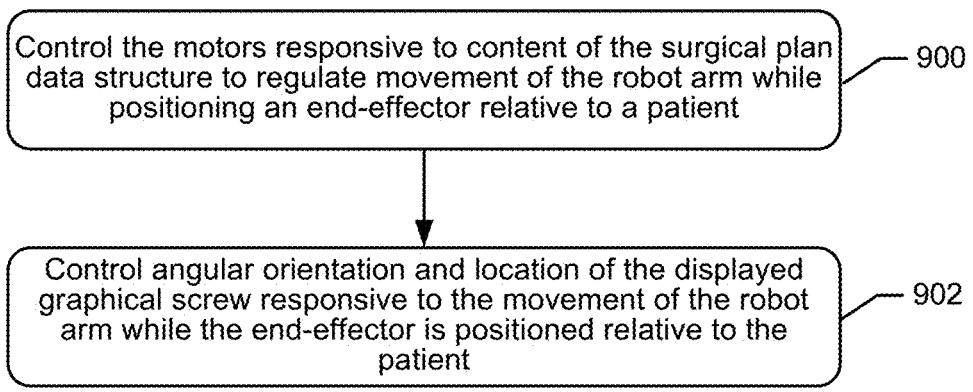

Referring to the alternative or additional operations of FIG. 83, the processor 614 of the surgical implant planning computer 610 can control 710 the robot 500 by controlling 900 selected ones of the motors 550-554, either directly or indirectly via the computer 522 and/or controller 546, responsive to content of the surgical plan data structure to regulate movement of the robot arm while positioning an end-effector 544, which is connected to the robot arm, relative to a patient. The processor 614 can also control 902 angular orientation and location of the displayed graphical screw on the display 612 responsive to the movement of the robot arm while the end-effector 544 is positioned relative to the patient.

In a further embodiment, the processor 614 can directly or indirectly control 900 one or more of the motors 550-554 to move the end-effector 544 in a direction along a trajectory that is defined by the content of the surgical plan data structure, and can control 902 location of the displayed graphical screw responsive to the movement of the end-effector 544 along the trajectory.

In a further embodiment, while moving the end-effector 544 along the trajectory, the processor 614 can directly or indirectly control one or more of the motors 550-554 to resist movement of the end-effector 544 in a direction that is perpendicular to the trajectory until another operation is perform that cancels an end-effector trajectory constraint mode. In a further embodiment, prior to initiating the end-effector trajectory constraint mode, the processor 614 can directly or indirectly control one or more of the motors 550-554 to move the end-effector 544 in a direction upward away from the patient and then toward a location along the trajectory toward the patient, and prevent initiation of the end-effector trajectory constraint mode before reaching the location along the trajectory. The processor can control angular orientation and location of the displayed graphical screw responsive to the movement of the robot arm away from the patient and then toward the location along the trajectory.

Pre-Operative CT Imaging Workflow
Image Tab
Loading the Image

The IMAGE tab shows the steps needed to load a CT scan image. The image can be loaded from a USB drive or hard drive. If the image is transferred through the Ethernet, it automatically appears on the hard drive when the transfer is complete.

To view images on a USB drive, insert the USB drive into the USB port on the connector panel. To load an image, select the hard drive or USB drive icon and select the desired patient image. Click the right arrows to load the patient images and advance to the next tab.

Pre-Operative CT Imaging Workflow
Plan Tab

Figure 67:
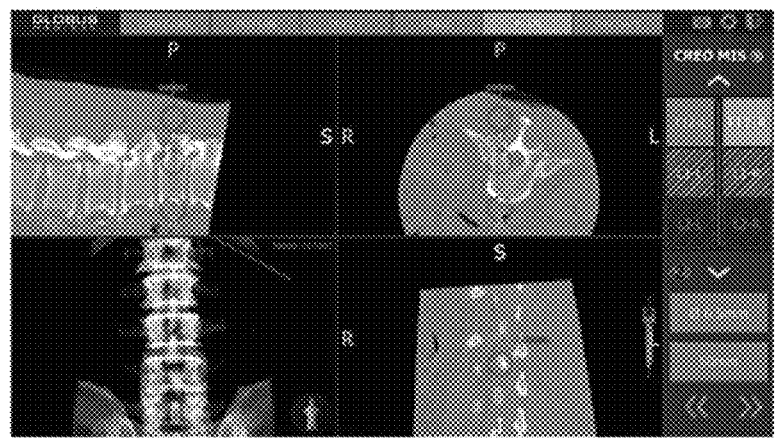
FIG. 67 illustrates a PLAN tab allowing a user to plan all screw trajectories on a patient image.

FIG. 67 illustrates the PLAN tab allowing the user to plan all screw trajectories on the patient image. Screws are preloaded on the right-hand side of the screen, based on selections made in the PREPLAN tab.

To add a screw onto the planning page, drag and drop the appropriate screw label on the image at the desired slice. The active screw plan is shown in green. Details of the active screw plan are shown on the lower right of the screen, including screw family, diameter, and length. Click on the right arrows to advance to the next tab once plans are complete for all screws.

| Adjusting screw trajectory | |
| --- | --- |
| Screw Body | Press and move along screen to translate the screw along the current plane of the anatomy |
| Screw Head | Press and move to change the angle of the trajectory, pivoting along the tip of the screw |
| Screw Tip | Press and move to change the angle of the trajectory, pivoting along the head of the screw |
| Scroll Bar | The scroll bar is the dial control located above the head of the screw. Press the scroll bar and move to rotate the anatomy 360° about the screw. |

| Adjusting screw size | |
| --- | --- |
| Screw Tip | Press and move longitudinally to automatically adjust the length of the screw to available screw sizes |
| Screw Diameter | Press the screw diameter button located on the right hand side of the screen to select other options available with the selected implant set |
| Screw Length | Press the screw length button located on the right hand side of the screen to select other options available with the selected implant set |

Pre-Operative CT Imaging Workflow Planning Operations

Figure 84:
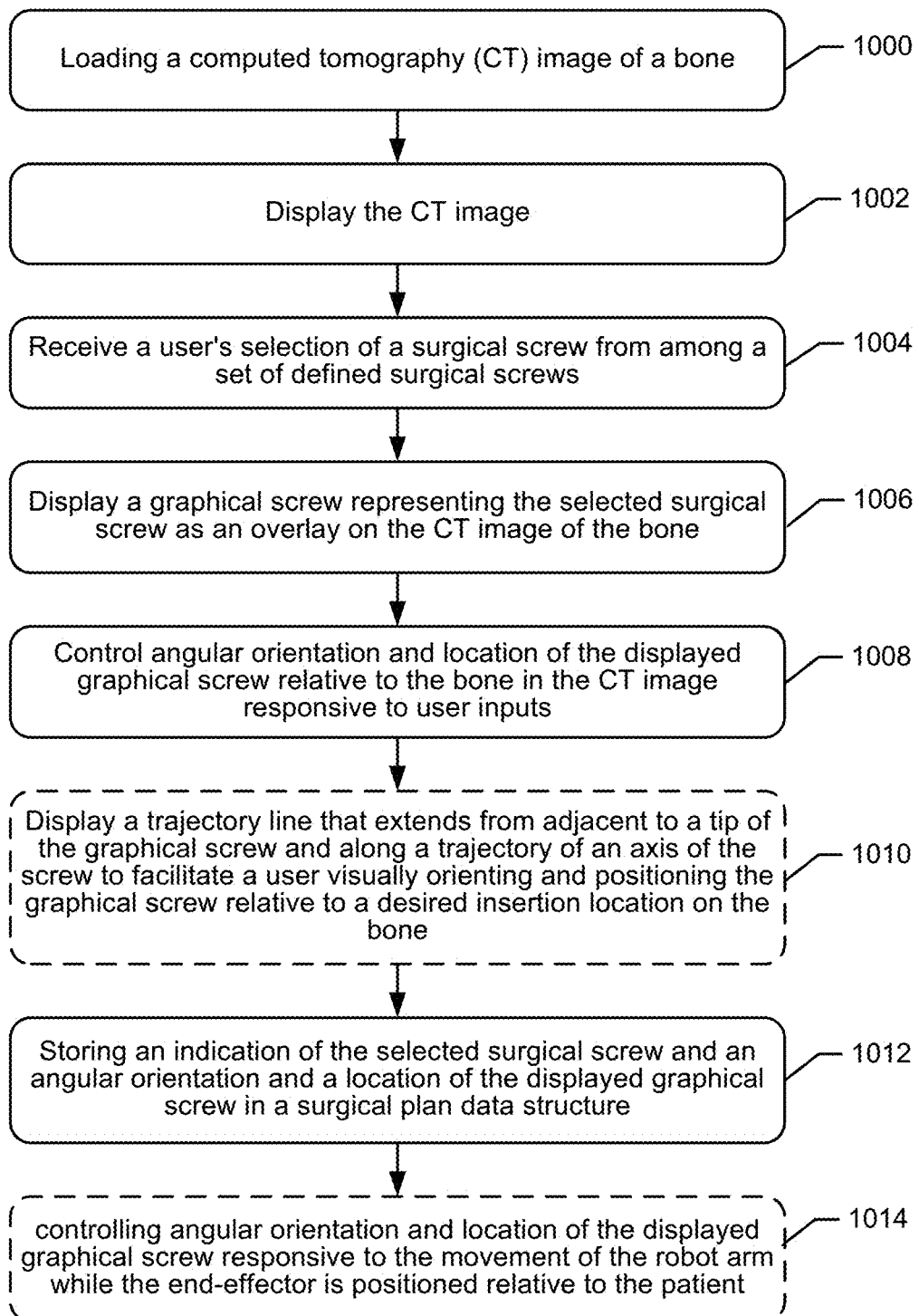

Pre-operative CT imaging workflow planning operations that can be performed by the surgical implant planning computer 610 and, more particularly by the processor 614, are now described in the context of the embodiments shown in FIG. 84.

Referring to FIG. 84, the operations can include loading 1000 a CT image of a bone, which is received from the image database 650 through the network interface 620, into the memory 616. The operations include displaying 1002 the CT image on the display device 612, and receiving 1004 a user's selection of a surgical screw from among a set of defined surgical screws. The operations display 1006 a graphical screw representing the selected surgical screw as an overlay on the CT image of the bone. The operations control 1008 angular orientation and location of the displayed graphical screw relative to the bone in the CT image responsive to receipt of user inputs. The operations store 1012 an indication of the selected surgical screw and an angular orientation and a location of the displayed graphical screw in a surgical plan data structure responsive to user input. The surgical plan data structure is configured for use by the robot 500 to control movement of the robot arm in accordance with various embodiments disclosed herein.

The operations to display 1006 the graphical screw representing the selected surgical screw as an overlay on the CT image of the bone, can include determining a trajectory along an axis of the graphical screw, and displaying 1010 a trajectory line that extends from adjacent to a tip of the graphical screw and along the trajectory to facilitate a user visually orienting and positioning the graphical screw relative to a desired insertion location on the bone.

The operations to control 1008 angular orientation and location of the displayed graphical screw relative to the bone in the CT image responsive to receipt of user inputs, can include translating a location of the displayed graphical screw responsive to determining that the user has pressed on a touch-sensitive screen of the display device 612 over a screw body of the graphical screw while moving location of the user's continued pressing along the touch-sensitive screen. The operations can alternatively or additionally include angularly pivoting the displayed graphical screw responsive to determining that the user has pressed on the touch-sensitive screen over a screw head and/or tip of the graphical screw while moving location of the user's continued pressing along the touch-sensitive screen.

The operations to control 1008 angular orientation and location of the displayed graphical screw relative to the bone in the CT image responsive to receipt of user inputs, can include selecting a length of the displayed graphical screw from among a set of defined lengths for surgical screws responsive to determining that the user has pressed on a touch-sensitive screen of the display device 612 over a screw tip or a screw head of the graphical screw while moving location of the user's continued pressing along the touch-sensitive screen a measured distance.

The selected length of the surgical screw is stored 1012 in the surgical plan data structure.

The operations can include controlling 1014 angular orientation and location of the displayed graphical screw responsive to the movement of the robot arm while the end-effector 544 is being positioned relative to a patient.

Pre-Operative CT Imaging Workflow
Navigate Tab

The NAVIGATE tab allows the user to visualize the navigated instruments and trajectory alignment with respect to patient anatomy, according to the screw plan.

Registration Setup

Figure 68:
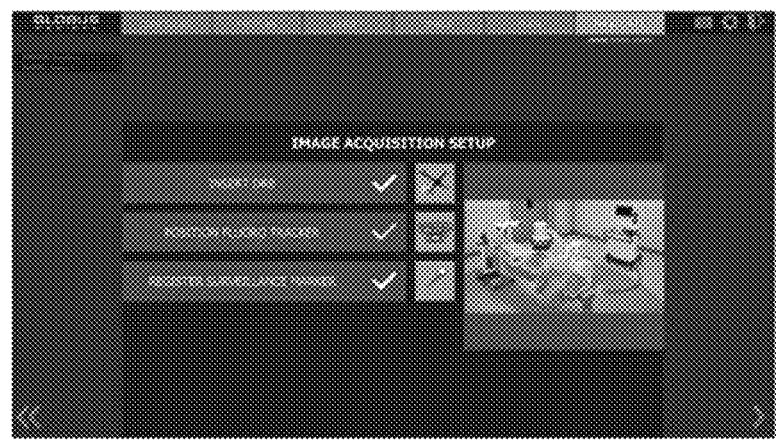
FIG. 68 illustrates the first screen highlighting the three steps to complete before the fluoroscopy images can be taken to register the pre-operative CT image.

FIG. 68 illustrates the first screen highlighting the three steps to complete before the fluoroscopy images can be taken to register the pre-operative CT image. Animation visually depicts the steps.

Figure 69:
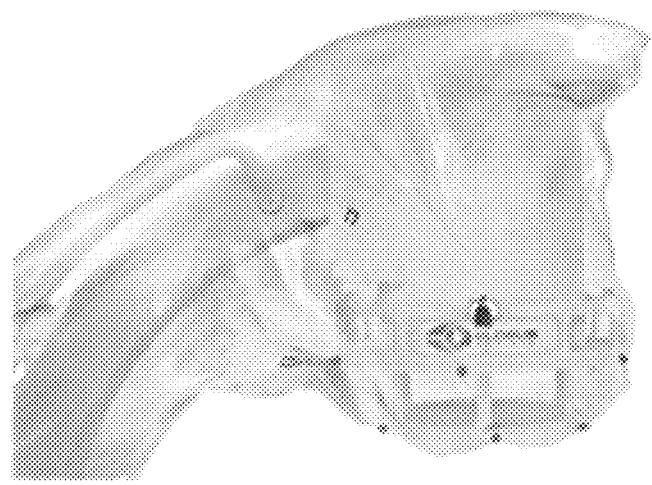
FIG. 69 illustrates a Fluoroscopy Registration Fixture attached to image intensifier.

FIG. 69 illustrates a Fluoroscopy Registration Fixture attached to image intensifier. Attach the Fluoroscopy Registration Fixture to the image intensifier on the C-arm by turning the clamps clockwise until tight. Drape the fluoroscope and Fluoroscopy Registration Fixture and attach new reflective markers outside of the drape. Position the fixture such that the reflective markers are facing the camera. Attach the video capture cable (yellow jack) to the C-arm viewing station. Plug the video capture USB cable into either of the two USB ports on the robotic computer system connector panel.

Ensure that the Dynamic Reference Base is visible to the camera after the C-Arm is in place.

Register the surveillance marker by placing an instrument close to the reflective sphere on the surveillance marker but not touching. The box turns green when it is activated. Click the right arrows to advance to the next tab.

Pre-Operative CT Imaging Workflow Navigation Operations

Figure 85:
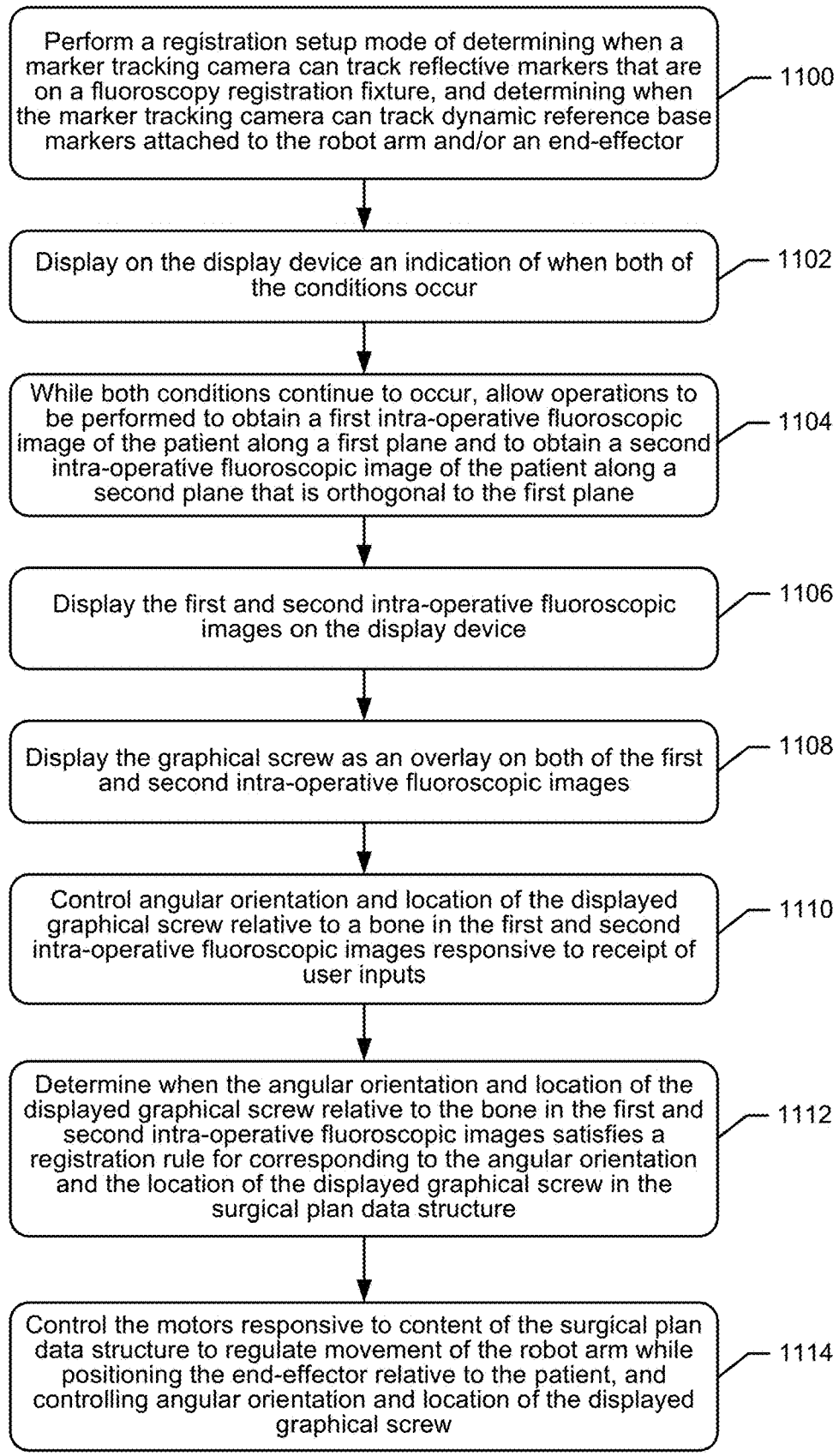

Pre-operative CT imaging workflow navigation operations that can be performed by the surgical implant planning computer 610 and, more particularly by the processor 614, are now described in the context of the embodiments shown in FIG. 85.

Referring to FIG. 85, the operations can include performing 1100 a registration setup mode that includes determining occurrence of a first condition indicating that a marker tracking camera 570 can observe to track reflective markers that are on a fluoroscopy registration fixture (e.g., connected to the fluoroscopy imager 640), and further determining occurrence of a second condition indicating that the marker tracking camera 570 can observe to track dynamic reference base markers attached to the robot arm and/or an end-effector 544 connected to the robot arm. The operations display 1102 on the display device 612 an indication of when both of the first and second conditions occur, and determine that the registration setup mode is allowed to be marked satisfied when at least both of the first and second conditions are determined to occur.

Registration

Acquire the intra-operative fluoroscopic images, one AP and one lateral for each level planned. The same image may be used for multiple levels.

The following three conditions must be met prior to acquiring the images: (1) the DRB is visible by the camera; (2) the Fluoroscopy Registration Fixture is visible by the camera; and (3) a valid fluoroscopic image was taken.

Figure 70:
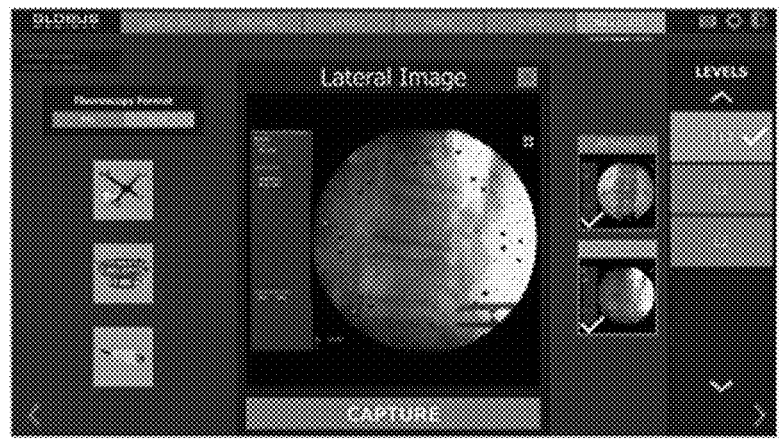
FIG. 70 illustrates a lateral image within the NAVIGATE tab.

FIG. 70 illustrates a lateral image within the NAVIGATE tab. Referring to FIG. 70. Each of the three images on the left of the screen turns green when ready for image capture. When all three conditions are met, acquire the intra-operative fluoroscopic image and then select the CAPTURE button to transfer the image to the system. Once both images are successfully captured, the spinal level on the right side of the screen displays a check mark. Click the right arrows to advance to the next tab.

Figure 71:
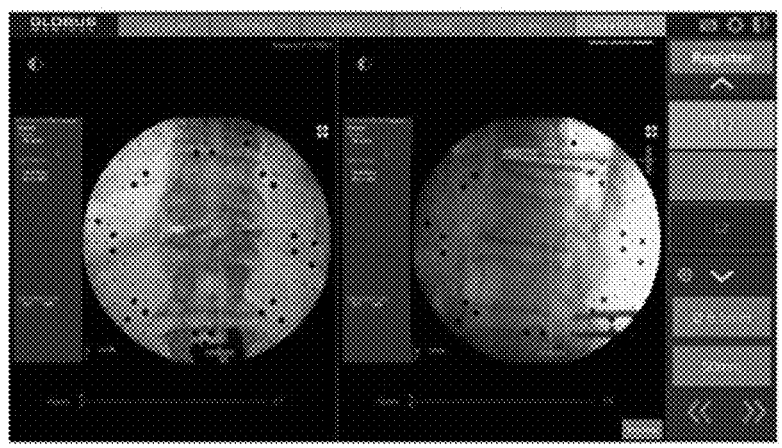
FIG. 71 illustrates selecting the desired level.

FIG. 71 illustrates selecting the desired level. To do so, the user drags and drops the planned screw onto the fluoroscopic images. Use the circle control points to roughly position the screw within the vertebral body. Ensure that the screw shank is positioned correctly, the head and tail of the screws are in the desired direction, and left/right are correctly oriented. Click the register button when complete to allow registration.

Figure 72:
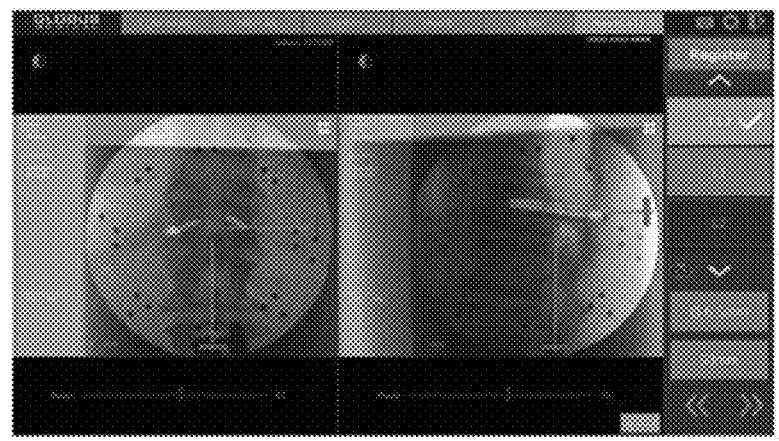
FIG. 72 illustrates a successful registration with a check mark being shown next to the active level.

FIG. 72 illustrates a successful registration with a check mark being shown next to the active level. Click the right arrows when registration is complete.

Pre-Operative CT Imaging Workflow Navigation Operations

With further reference to FIG. 85, the operations by the surgical implant planning computer 610 can further include operating 1104 while both of the first and second conditions are determined 1104 to continue to occur, to allow operations to be performed to obtain a first intra-operative fluoroscopic image of the patient along a first plane and to obtain a second intra-operative fluoroscopic image of the patient along a second plane that is orthogonal to the first plane. The operations determine that a registration mode is allowed to be marked satisfied when the first and second intra-operative fluoroscopic images have been obtained.

With further reference to FIG. 85, the operations by the surgical implant planning computer 610 can further include displaying 1106 the first and second intra-operative fluoroscopic images on the display device 612. The operations display 1108 the graphical screw as an overlay on both of the first and second intra-operative fluoroscopic images. The operations control 1110 angular orientation and location of the displayed graphical screw relative to a bone in the first and second intra-operative fluoroscopic images responsive to receipt of user inputs.

Operations may alternatively or additionally include determining 1112 when the angular orientation and location of the displayed graphical screw relative to the bone in the first and second intra-operative fluoroscopic images satisfies a registration rule for corresponding to the angular orientation and the location of the displayed graphical screw in the surgical plan data structure, and then responsively displaying on the display device 612 an indication of when the registration rule is satisfied.

With further reference to FIG. 85, the operations by the surgical implant planning computer 610 can further include, based on determining that the registration rule is satisfied, controlling 1114 one or more of the motors 550-554 responsive to content of the surgical plan data structure to regulate movement of the robot arm while positioning the end-effector 544 relative to the patient. The operations can further control 1114 angular orientation and location of the graphical screw that is displayed, responsive to the movement of the robot arm while the end-effector 544 is being positioned relative to the patient.

Landmark Check

After registration has been completed, a landmark check, or verification, should be performed to ensure that the registration was calculated successfully. Using the verification probe, touch an anatomical landmark and verify that the corresponding location is shown on the system monitor. Repeat this process using 2-3 landmarks.

Removing Registration Fixture

Carefully remove the Fluoroscopy Registration Fixture if desired.

Navigation

The robotic arm precisely aligns the end-effector on the planned trajectory. Select the desired screw label on the right of the screen.

The screw plan is active when the screw label is highlighted and the robotic arm can be moved by the bracelet or pressing the foot pedal. The robotic arm first moves up in order to clear obstacles in the surgical field and then down along the trajectory. Once on the trajectory, the robotic arm can move up/down along the trajectory but does not move off of the trajectory unless the screw is deselected.

Figure 73:
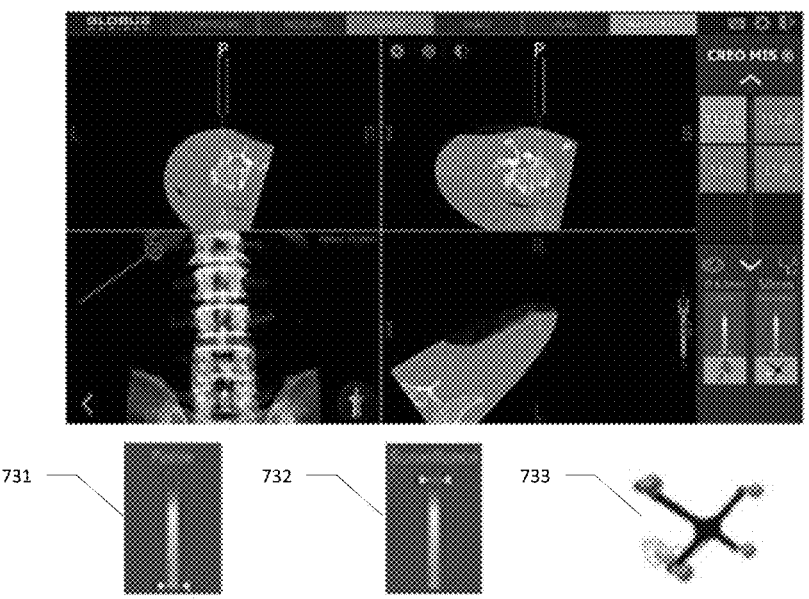
FIG. 73 illustrates how the real-time instrument/implant trajectory is displayed on the patient images along with the planned screw, allowing the user to confirm the desired trajectory.

FIG. 73 illustrates how the real-time instrument/implant trajectory is displayed on the patient images along with the planned screw, allowing the user to confirm the desired trajectory. If the real-time trajectory is not acceptable, the user can return to the PLAN tab to select another trajectory. If the real-time trajectory is acceptable, the user inserts the screw according to the instrument's current trajectory to the desired depth.

GPS instruments are displayed as they are advanced through the end-effector. While navigating the instruments, periodically observe the monitor and surgical site to ensure consistency between tactile and navigation feedback.

Non-navigated metallic Globus instruments may be used through the guide tube while it is stationary for surgical applications unrelated to screw placement.

Monitor the surveillance marker during the procedure. If the surveillance marker indicates significant movement of the DRB, perform an anatomical landmark check. If the landmark check is satisfactory, re-register the surveillance marker. If the landmark check fails, re-register the patient.

There are multiple navigation tab icons. Referring to FIG. 73, the force gauge 731 indicates the force exerted on the end-effector. The image of the instrument at the bottom of the force gauge shows the active instrument in the end-effector or the end-effector image if no instrument is inserted. The surveillance marker error gauge 732 indicates the distance that the patient reference has moved in relation to the surveillance marker. The full range of the scale is 2 mm. The DRB icon 733 indicates dynamic reference base visibility. If the DRB is visible by the camera, the background is green. If the DRB is not visible by the camera, the background is red.

Fluoroscopic Imaging Workflow

Image Tab

Registration Setup

Referring to FIG. 68 the first screen highlights the three steps to complete before fluoroscopic images can be taken to register the patient. Animation visually depicts the steps.

Referring to FIG. 69, attach the Fluoroscopy Registration Fixture to the image intensifier on the C-arm by turning the clamps clockwise until tight. Drape the fluoroscope and Fluoroscopy Registration Fixture and attach new reflective markers outside of the drape. Position the fixture such that the reflective markers are facing the camera. Attach the video capture cable (yellow jack) to the C-arm viewing station. Plug the video capture USB cable into either of the two USB ports on the robotic computer system connector panel.

Ensure that the Dynamic Reference Base is visible to the camera after the C-Arm is in place.

Register the surveillance marker by placing an instrument close to the reflective sphere on the surveillance marker but not touching. The box turns green when it is activated. Click the right arrows to advance to the next tab.

Image Acquisition

Acquire intra-operative fluoroscopic images, one AP and one lateral.

The following three conditions must be met prior to acquiring the images: (1) the DRB is visible by the camera; (2) the Fluoroscopy Registration Fixture is visible by the camera; and (3) a valid fluoroscopic image was taken.

Figure 74:
FIG. 74 illustrates a lateral image within the NAVIGATE tab.

FIG. 74 illustrates a lateral image within the NAVIGATE tab. Referring to FIG. 74, each of the three images on the left of the screen turn green when ready for image capture. When all three conditions are met, acquire the intra-operative fluoroscopic image and then select the CAPTURE button to transfer the image to the system. Once both images are successfully captured, the level on the right side of the screen displays a check mark. Once the appropriate images have been loaded and selected, click on the right arrows to proceed.

Landmark Check

After registration has been completed, a landmark check, or verification, should be performed to ensure that the registration was calculated successfully. Using the navigated verification probe, touch an anatomical landmark and verify that the corresponding location is shown on the system monitor. Repeat this process using 2-3 landmarks.

Removing Registration Fixture

Carefully remove the fluoroscopy registration fixture if desired.

Fluoroscopic Imaging Workflow Operations

Figure 86:
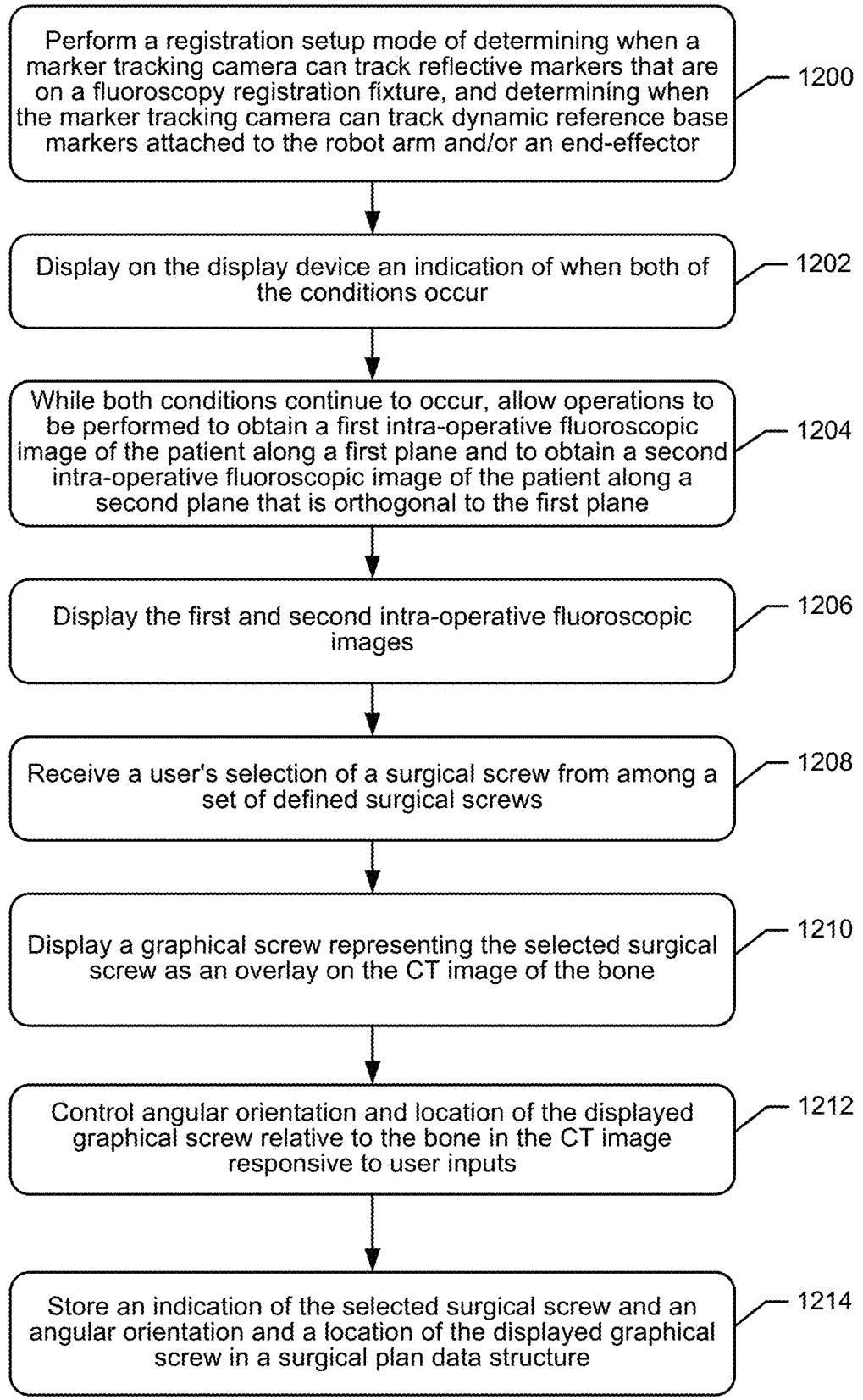

Fluoroscopic imaging workflow operations that can be performed by the surgical implant planning computer 610 and, more particularly by the processor 614, are now described in the context of the embodiments shown in FIG. 86.

Referring to FIG. 86, the operations can include performing 1200 operations for a registration setup mode that include determining occurrence of a first condition indicating that the marker tracking camera 570 can observe to track reflective markers that are on a fluoroscopy registration fixture of the fluoroscopy imager 640, and determining occurrence of a second condition indicating the marker tracking camera 570 can observe to track dynamic reference base markers attached to the robot arm and/or the end-effector 544 connected to the robot arm. While both of the first and second conditions are determined to continue to occur, the processor 614 allows 1204 operations to be performed to obtain a first intra-operative fluoroscopic image of a patient along a first plane and to obtain a second intra-operative fluoroscopic image of the patient along a second plane that is orthogonal to the first plane. The operations may display 1202 on the display device 612 an indication of when both of the conditions occur. If one or both conditions cease to be satisfied before the first and second intra-operative fluoroscopic images are obtained, the system may interrupt further obtaining of the uncompleted first and second intra-operative fluoroscopic imaging and generate a notification to the user.

The operations can further include displaying 1206 the first and second intra-operative fluoroscopic images on the display device 612. The operations can receive 1208 a user's selection of a surgical screw from among a set of defined surgical screws, and display 1210 a graphical screw representing the selected surgical screw as an overlay on both of the first and second intra-operative fluoroscopic images. The operations can control 1212 angular orientation and location of the displayed graphical screw relative to a bone shown in the first and second intra-operative fluoroscopic images responsive to receipt of user inputs, and store 1214 an indication of an angular orientation and a location of the displayed graphical screw in a surgical plan data structure responsive to receipt of a defined user input.

Fluoroscopic Imaging Workflow
Plan Tab

Figure 75:
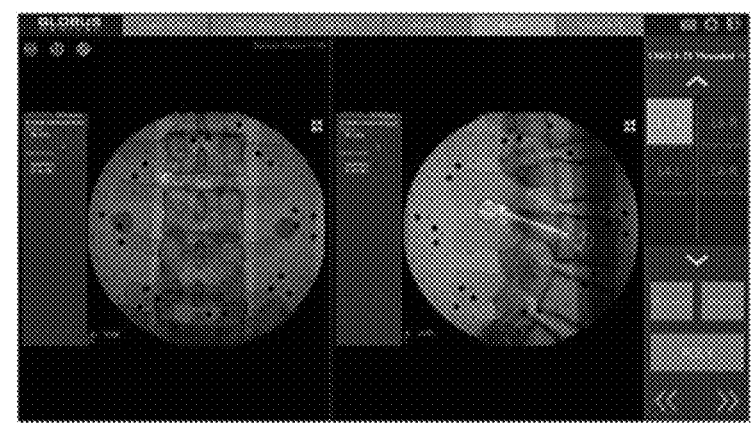
FIG. 75 illustrates the PLAN tab allowing the user to plan all screw trajectories on the patient image.

FIG. 75 illustrates the PLAN tab allowing the user to plan all screw trajectories on the patient image. Referring to 75, screws are preloaded on the right side of the screen, based on selections made in the PREPLAN tab.

To add a screw onto the planning page, drag and drop the appropriate screw label on the image at the desired slice.

The active screw plan is shown in green. Details of the active screw plan are shown on the lower right of the screen, including screw family, diameter, and length. Click on the right arrows to advance to the next tab once plans are complete for all screws.

| Adjusting screw trajectory | |
|---|---|
| Screw Head | Press and move along screen to adjust the screw along the current plane of the anatomy |
| Screw Tip | Press and move to change the angle of the trajectory, pivoting along the head of the screw |
| Screw Trajectory | Press and move the screw along the 3D trajectory. This is useful to simulate actual advancement of the screw in 3D space. Both AP and Lateral images will be updated to reflect the new screw position. |

| Adjusting screw size | |
|---|---|
| Screw Diameter | Press the screw diameter button located on the right hand side of the screen to select other options available with the selected implant set |
| Screw Length | Press the screw length button located on the right hand side of the screen to select other options available with the selected implant set |

Fluoroscopic Imaging Workflow Planning Operations

Figure 87:
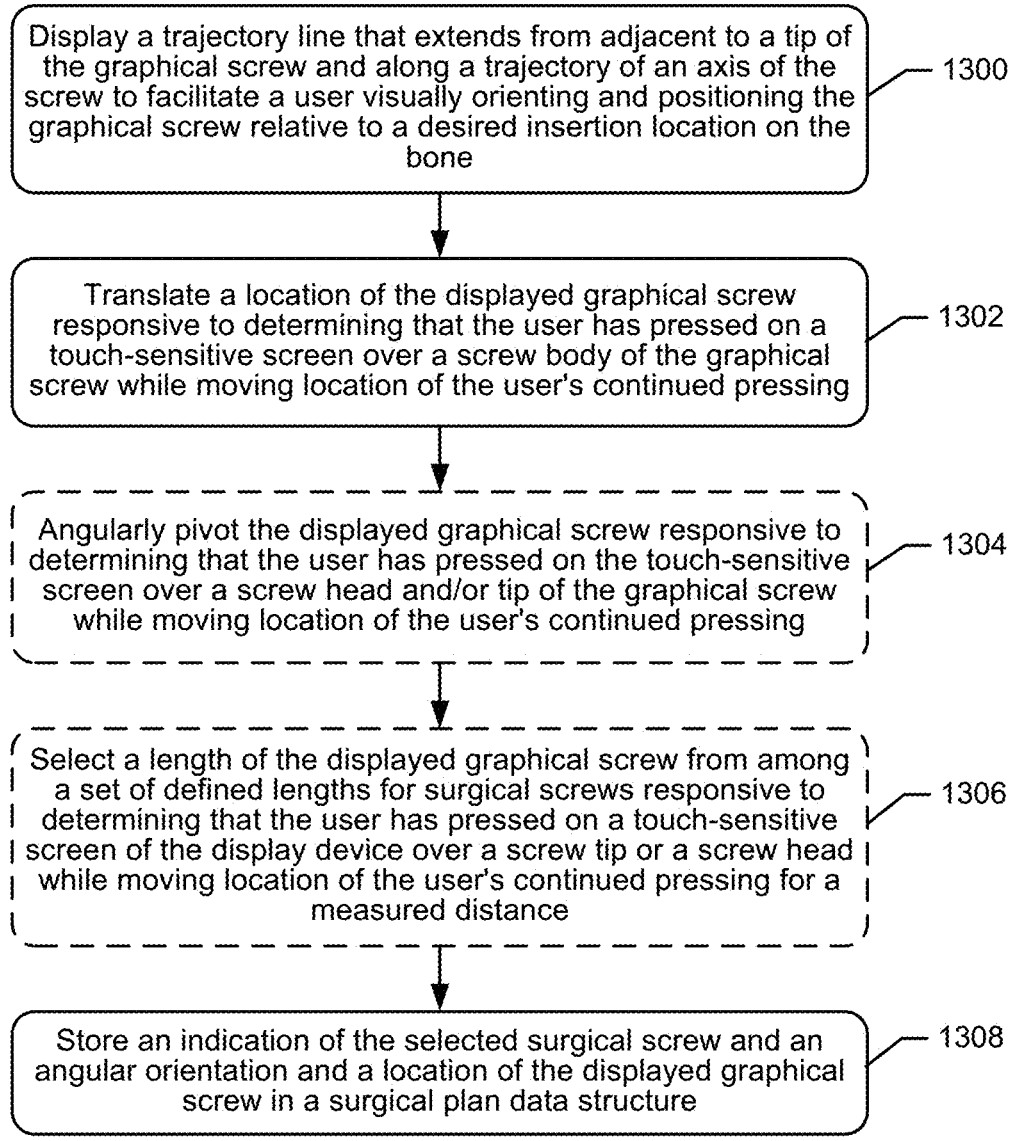

Fluoroscopic imaging workflow operations for planning that can be performed by the surgical implant planning computer 610 and, more particularly by the processor 614, are now described in the context of the embodiments shown in FIG. 87.

Referring to FIG. 87, operations to display the graphical screw representing the selected surgical screw as an overlay on both of the first and second intra-operative fluoroscopic images, can include determining 1300 a trajectory along an axis of the graphical screw and displaying a trajectory line that extends from adjacent to a tip of the graphical screw and along the trajectory to facilitate a user visually orienting and positioning the graphical screw relative to a desired insertion location on the bone.

Operations to control angular orientation and location of the displayed graphical screw relative to the bone shown in the first and second intra-operative fluoroscopic images responsive to receipt of user inputs, can include translating 1302 a location of the displayed graphical screw responsive to determining that the user has pressed on a touch-sensitive screen of the display device 612 over a screw body of the graphical screw while moving location of the user's continued pressing along the touch-sensitive screen. The operations can further include angularly pivoting 1304 the displayed graphical screw responsive to determining that the user has pressed on the touch-sensitive screen over a screw head and/or tip of the graphical screw while moving location of the user's continued pressing along the touch-sensitive screen.

Operations to control angular orientation and location of the displayed graphical screw relative to the bone shown in the first and second intra-operative fluoroscopic images responsive to receipt of user inputs, can include selecting 1306 a length of the displayed graphical screw from among a set of defined lengths for surgical screws responsive to determining that the user has pressed on a touch-sensitive screen of the display device 612 over a screw tip or a screw head of the graphical screw while moving location of the user's continued pressing along the touch-sensitive screen a measured distance. The selected length is stored 1308 in the surgical plan data structure.

Fluoroscopic Imaging Workflow
Navigate Tab

Figure 76:
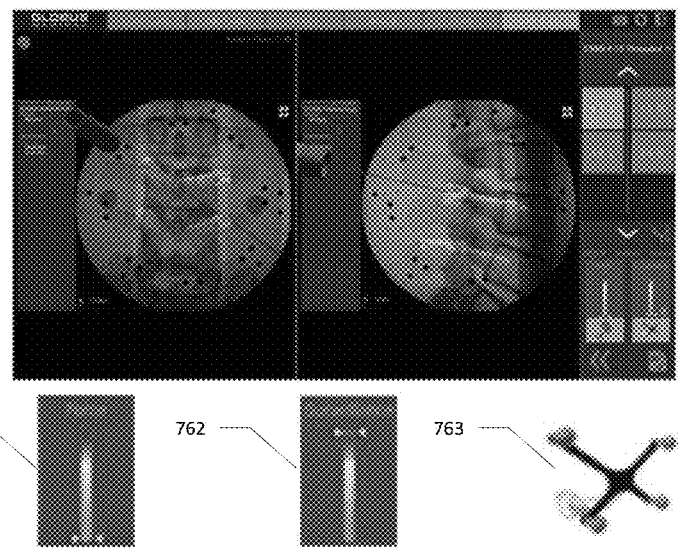
FIG. 76 illustrates the NAVIGATE tab allowing the user to visualize the navigated instrument trajectory and the planned trajectory with respect to patient anatomy.

FIG. 76 illustrates the NAVIGATE tab allowing the user to visualize the navigated instrument trajectory and the planned trajectory with respect to patient anatomy.

The robotic arm precisely aligns the end-effector to the planned trajectory. Referring to FIG. 76, select the desired screw label on the right of the screen.

The screw plan is active when the screw label is highlighted and the robotic arm can be moved by the bracelet or pressing the foot pedal. The robotic arm first moves up in order to clear obstacles in the surgical field and then down along the trajectory. Once on the trajectory, the robotic arm can move up/down along the trajectory but does not move off of the trajectory unless the screw plan is deselected.

The real-time instrument/implant trajectory is displayed on the patient images along with the planned screw, allowing the user to confirm the desired trajectory. If the real-time trajectory is not acceptable, the user can return to the PLAN tab to select another trajectory. If the real-time trajectory is acceptable, the user inserts the screw according to the instrument's current trajectory to the desired depth.

GPS instruments are displayed as they are advanced through the end-effector. While navigating the instruments, periodically observe the monitor and surgical site to ensure consistency between tactile and navigation feedback.

Non-navigated metallic Globus instruments may be used through the guide tube while it is stationary for surgical applications unrelated to screw placement.

Monitor the surveillance marker during the procedure. If the surveillance marker indicates significant movement of the DRB, perform an anatomical landmark check. If the landmark check is satisfactory, re-register the surveillance marker. If the landmark check fails, re-register the patient.

There are multiple navigation tab icons. Referring to FIG. 76, the force gauge 761 indicates the force exerted on the end-effector. The image of the instrument at the bottom of the force gauge shows the active instrument in the end-effector or the end-effector image if no instrument is inserted. The surveillance marker error gauge 762 indicates the distance that the patient reference has moved in relation to the surveillance marker. The full range of the scale is 2 mm. The DRB icon 763 indicates dynamic reference base visibility. If the DRB is visible by the camera, the background is green. If the DRB is not visible by the camera, the background is red.

Navigation-Only Procedures

Figure 77:
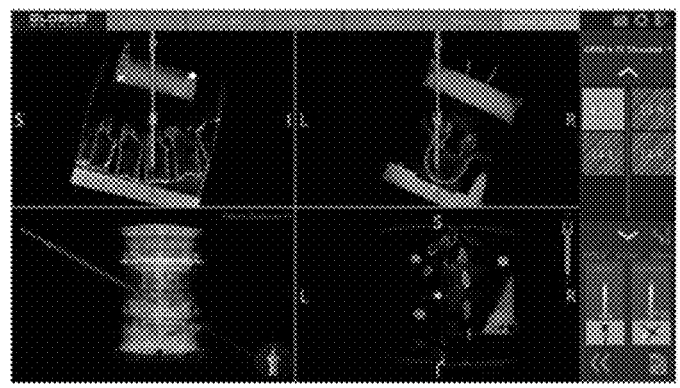
FIG. 77 illustrates how the robotic computer system may be used for navigation without the robotic arm and end effector.

FIG. 77 illustrates how the robotic computer system may be used for navigation without the robotic arm and end effector. Pre-surgical planning is optional. Referring to FIG. 77, all verified GPS instruments are visible on loaded patient images when moved within the view of the camera. The instruments are displayed with respect to the patient.

Refer to the corresponding application and imaging workflow for the imaging modality (pre-operative CT, intra-operative CT, or fluoroscopy).

Use the IMAGE tab to load the desired patient images.

After instrument registration has been completed, a landmark check, or verification, should be performed to ensure that the registration was calculated successfully. Using the navigated verification probe, touch an anatomical landmark and verify that the corresponding location is shown on the system monitor. Repeat this process using 2-3 landmarks.

Use the PLAN tab to plan screw placement if desired. Select the desired screw label on the right of the screen to choose the screw plan.

Use the NAVIGATE tab to display the screw and navigated instruments during the procedure.

Monitor the surveillance marker during the procedure. If the surveillance marker indicates significant movement of the DRB, perform an anatomical landmark check. If the landmark check is satisfactory, re-register the surveillance marker. If the landmark check fails, re-register the patient.

Trajectory-Only Procedures

Figure 78:
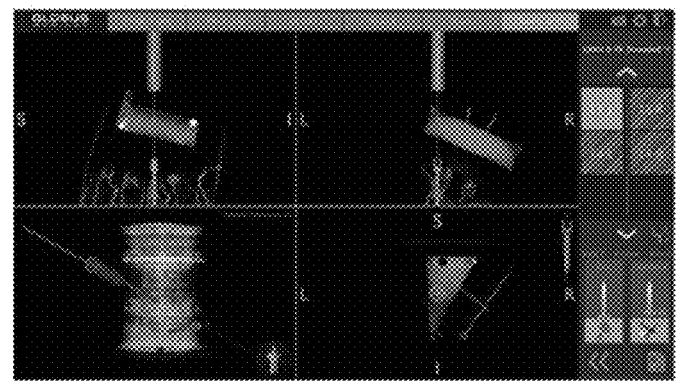
FIG. 78 illustrates how the robotic computer system may be used for trajectory guidance using the robotic arm without navigated instruments.

FIG. 78 illustrates how the robotic computer system may be used for trajectory guidance using the robotic arm without navigated instruments. Referring to t FIG. 78, the guide tube serves as a rigid retractor that can be moved within the surgical field or aligned to a trajectory automatically or manually.

Refer to the corresponding application and imaging workflow for the imaging modality (pre-operative CT, intra-operative CT, or fluoroscopy). Use the IMAGE tab to load the desired patient images.

A landmark check, or verification, should be performed to ensure that the registration was calculated successfully. Using the navigated verification probe, touch an anatomical landmark and verify that the corresponding location is shown on the system monitor. Repeat this process using 2-3 landmarks.

Use the PLAN tab to plan screw placement. Select the desired screw label on the right of the screen. The screw plan is active when the screw label is highlighted and the robotic arm can be moved by the bracelet or by pressing the foot pedal and moving the arm. The robotic arm first moves up to clear obstacles in the surgical field and then down along the specified trajectory. Once on the trajectory, the robotic arm can be moved up/down along the trajectory but does not move off of the trajectory unless the screw is deselected.

If using k-wires, use the cannulated awl to prepare the starting hole and place the k-wire into bone at the desired trajectory through the guide tube. The end effector should be moved away from the trajectory so the screw can be placed by k-wire guidance (deselect the screw plan).

Perform the surgical procedure using non-navigated metallic surgical instruments that fit through the guide tube diameter.

Monitor the surveillance marker during the procedure. If the surveillance marker indicates significant movement of the DRB, perform an anatomical landmark check. If the landmark check is satisfactory, re-register the surveillance marker. If the landmark check fails, re-register the patient.

Fluoroscopic Imaging Workflow Planning Operations

As explained above, the fluoroscopic imaging workflow operations for planning by the surgical implant planning computer 610 can include displaying the graphical screw representing the selected surgical screw as an overlay on both of the first and second intra-operative fluoroscopic images. The operations can determine 1300 a trajectory along an axis of the graphical screw and displaying a trajectory line that extends from adjacent to a tip of the graphical screw and along the trajectory to facilitate a user visually orienting and positioning the graphical screw relative to a desired insertion location on the bone.

The operations may further include directly or indirectly, e.g., via the computer 522 and/or controller 546, controlling one or more of the motors 550-554 responsive to content of the surgical plan data structure to regulate movement of the robot arm while positioning the end-effector 544 relative to a patient. The operations can control (e.g., 1212 in FIG. 86) angular orientation and location of the displayed graphical screw responsive to the movement of the robot arm while the end-effector 544 is being positioned relative to the patient.

The operations can further include directly or indirectly, e.g., via the computer 522 and/or controller 546, controlling the motors 550-554 to move the end-effector 544 in a direction along a trajectory defined by the content of the surgical plan data structure. The operations can further include controlling (e.g., 1212 in FIG. 86) location of the displayed graphical screw responsive to the movement of the end-effector 544 along the trajectory.

The operations can further include, while moving the end-effector 544 along the trajectory, directly or indirectly controlling the motors 550-554 to resist movement of the end-effector 544 in a direction perpendicular to the trajectory until another operation is perform that cancels an end-effector trajectory constraint mode.

The operations can further include, prior to initiating the end-effector trajectory constraint mode, directly or indirectly controlling the motors 550-554 to move the end-effector 544 in a direction upward away from the patient and then toward a location along the trajectory, and preventing initiation of the end-effector trajectory constraint mode before reaching the location along the trajectory. The operations can control angular orientation and location of the displayed graphical screw responsive to the movement of the robot arm away from the patient and then toward the location along the trajectory.

Software Error Messages

The system alerts the operator of errors through pop-up messages. The following list describes all possible errors and the actions to correct them.

| Message | Description | Proposed Remedy |
| --- | --- | --- |
| End Effector Disconnected | The End Effector is not attached to the robot arm. | Ensure that the End Effector is properly attached. |
| Stabilizer Not Down | Stabilizers have not been deployed. | Engage stabilizer. |
| Registration Not Completed | The patient scan did not pass automatic registration or was unregistered via the registration view. | Complete registration. |
| Registration Not Transferred | Registration has not yet been transferred from the intra-op CT registration fixture to the Dynamic Reference Base. | Transfer registration |
| Camera Disconnected | The connection to the camera was dropped, most likely as a result of a loose cable. | Ensure the camera is properly connected. |
| Camera Frame Rate Dropped | The frame rate of the camera has dropped below the system's safe limit. This is usually due to too many tracked instruments/objects in the camera's view. | Too many instruments in view of the camera. Removing instruments will increase the camera frame rate. |
| Camera CRC Mismatch | Data from camera is not valid, or there has been a camera communication problem. | Disconnect camera from Robotic Base Station and reconnect. |
| End Effector Not Visible | The End Effector is not currently visible to the camera. (This will stop or prevent motion as the End Effector fiducials must be visible to move the robot arm.) | Ensure the End Effector is in view of the camera. |
| DRB Not Visible | The Dynamic Reference Base is not currently visible to the camera (this will stop motion as the Dynamic Reference Base fiducials must be visible to move the robot arm). | Ensure the Dynamic Reference Base is in view of the camera. |
| E-Stop pressed | Someone has physically pressed the E-Stop or Emergency Stop button on the Robot Base Station. This stops motion. | Rotate the E-Stop button to release. |
| PIB Communication Dropped | Communication to the PIB (Platform Interface Board) has been lost. This severs communication to the robotic arm, which stops or prevents motion. | Restart the system. |
| Surveillance Marker Moved | The surveillance marker has moved beyond its safety-critical limit in relation to the Dynamic Reference Base. | Perform an anatomical landmark check to ensure navigation is still accurate. If navigation is inaccurate, either re-register the patient or discontinue use for that procedure. |
| Surveillance Marker Not Visible | The surveillance marker has either shifted dramatically or moved a great distance, which causes the camera to no longer see it. | Perform an anatomical landmark check to ensure navigation is still accurate. If navigation is inaccurate, either re-register the patient or discontinue use for that procedure. |
| Active Trajectory Not Reachable | The robotic arm cannot create a table of position points to move to a trajectory, based on the kinematics equations used. | Move Robotic Base Station to allow the arm to reach the trajectory. |
| Maximum Trajectory Error Exceeded | When the robot arm is locked onto a trajectory, if the actual position of the robot arm exceeds a certain distance from the perceived trajectory, this error will occur. Could be related to excessive force on the End Effector or kinematics issues. | Restart the move. |
| Excessive force on the End Effector | Excessive force has been applied to the load cell, over a certain limit (50N or 11 lbs) | Remove the force. |
| Excessive Dynamic Reference Base Movement | The Dynamic Reference Base position has shifted relatively quickly, without movement of other objects in the view of the camera. | Perform an anatomical landmark check to ensure navigation is still accurate. If navigation is inaccurate, either re-register the patient or discontinue use for that procedure. |
| Move Enabled Press Error | Move enabled is pressed while activating trajectory. Prevents the robot from instantly entering auto-move mode immediately after activating a trajectory. | Release the foot pedal or bracelet, then activate the trajectory. |
| GMAS Communication Failure | Communication with the GMAS controller has been lost. This will stop or prevent motion as GMAS is no longer receiving updates from the client about trajectory and camera. | The system should automatically connect. If not, restart the system. |

| Message | Description | Proposed Remedy |
| --- | --- | --- |
| Move Enabled Timeout | Move enable has been active for longer than threshold, 90 seconds or more. This is a failsafe for accidentally leaving the arm engaged. | Release the foot pedal or bracelet, then re-engage the foot pedal or bracelet. |
| Camera Bumped | Massive bump to the camera, in which the camera is likely to be permanently damaged. This is an error thrown internally by the NDI software. | Call Tech Support. |
| Tool in End Effector | If an instrument is in the End Effector when attempting to move, motion will be disallowed and this error will be displayed. | Remove instrument from End Effector. |
| Move Enabled Test Failure | The move enabled test has failed. | Ensure no buttons are pressed on the system and the system will automatically retry. |
| Motion Homing Failure | The homing routine for the robot has failed. This causes the robotic arm to lose its relative positions. This test can be retried, but if it consistently fails, there are no user actions to fix. | Call Tech Support. |
| Need to Home | Robot has not run its homing routine, thus the robot arm does not know its relative positions. | Call Tech Support. |

Further Definitions and Embodiments

In the above-description of various embodiments of the present disclosure, aspects of the present disclosure may be illustrated and described herein in any of a number of patentable classes or contexts including any new and useful process, machine, manufacture, or composition of matter, or any new and useful improvement thereof. Accordingly, aspects of the present disclosure may be implemented in entirely hardware, entirely software (including firmware, resident software, micro-code, etc.) or combining software and hardware implementation that may all generally be referred to herein as a "circuit," "module," "component," or "system." Furthermore, aspects of the present disclosure may take the form of a computer program product comprising one or more computer readable media having computer readable program code embodied thereon.

Any combination of one or more computer readable media may be used. The computer readable media may be a computer readable signal medium or a computer readable storage medium. A computer readable storage medium may be, for example, but not limited to, an electronic, magnetic, optical, electromagnetic, or semiconductor system, apparatus, or device, or any suitable combination of the foregoing. More specific examples (a non-exhaustive list) of the computer readable storage medium would include the following: a portable computer diskette, a hard disk, a random access memory (RAM), a read-only memory (ROM), an erasable programmable read-only memory (EPROM or Flash memory), an appropriate optical fiber with a repeater, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device. Program code embodied on a computer readable signal medium may be transmitted using any appropriate medium, including but not limited to wireless, wireline, optical fiber cable, RF, etc., or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C #, VB.NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable instruction execution apparatus, create a mechanism for implementing the functions/acts specified in the flowchart and/or block diagram block or blocks.

These computer program instructions may also be stored in a computer readable medium that when executed can direct a computer, other programmable data processing apparatus, or other devices to function in a particular manner, such that the instructions when stored in the computer readable medium produce an article of manufacture including instructions which when executed, cause a computer to implement the function/act specified in the flowchart and/or block diagram block or blocks. The computer program instructions may also be loaded onto a computer, other programmable instruction execution apparatus, or other devices to cause a series of operational steps to be performed on the computer, other programmable apparatuses or other devices to produce a computer implemented process such that the instructions which execute on the computer or other programmable apparatus provide processes for implementing the functions/acts specified in the flowchart and/or block diagram block or blocks.

It is to be understood that the terminology used herein is for the purpose of describing particular embodiments only and is not intended to be limiting of the invention. Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of this specification and the relevant art and will not be interpreted in an idealized or overly formal sense unless expressly so defined herein.

The flowchart and block diagrams in the figures illustrate the architecture, functionality, and operation of possible implementations of systems, methods, and computer program products according to various aspects of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular aspects only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Like reference numbers signify like elements throughout the description of the figures.

The corresponding structures, materials, acts, and equivalents of any means or step plus function elements in the claims below are intended to include any disclosed structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The aspects of the disclosure herein were chosen and described in order to best explain the principles of the disclosure and the practical application, and to enable others of ordinary skill in the art to understand the disclosure with various modifications as are suited to the particular use contemplated.

What is claimed is:

1. A surgical implant planning computer comprising:
   at least one network interface connectable to an image scanner and a robot having a robot base coupled to a robot arm that is movable by motors relative to the robot base;
   a display device;
   at least one processor; and
   at least one memory storing program code that is executed by the at least one processor to perform operations comprising:
   displaying on the display device first and second images at different orientations of a bone that are received from the image scanner through the at least one network interface;
   receiving a user's selection of a surgical screw from among a set of defined surgical screws;
   displaying a graphical screw representing the selected surgical screw as an overlay on the displayed first and second images of the bone;
   receiving as user inputs dragging of the displayed graphical screw to manipulate the angular orientation of the displayed graphical screw including pivoting the displayed graphical screw about the tip and about the head of the displayed graphical screw;
   updating on the display device angular orientation and location of the displayed graphical screw relative to the bone in both the first and second images responsive to receipt of the user inputs;
   receiving as a second user input selecting and dragging of the selected screw to simulate an advancement of the selected screw into the bone;
   updating on the display device the advancement of the selected screw only along a trajectory defined by the angular orientation of the selected screw in both the first and second images responsive to receipt of the second user input; and
   storing an indication of the selected surgical screw and an angular orientation and a location of the displayed graphical screw in a surgical plan data structure responsive to receipt of a defined user input.

2. The surgical implant planning computer of claim 1, wherein the angular orientation and the location stored in the surgical plan data structure indicates the angular orientation and the location of the displayed graphical screw relative to an angular orientation and a location of the bone in the first and second images.

3. The surgical implant planning computer of claim 1, wherein the operations to display the graphical screw representing the selected surgical screw as an overlay on the first and second images of the bone, comprise:
- determining a trajectory along an axis of the graphical screw; and
- displaying a trajectory line that extends from adjacent to a tip of the graphical screw and along the trajectory to facilitate a user visually orienting and positioning the graphical screw relative to a desired insertion location on the bone.

4. The surgical implant planning computer of claim 3, wherein the operations to control angular orientation and location of the displayed graphical screw relative to the bone in the first and second images responsive to receipt of user inputs, comprise:
- translating a location of the displayed graphical screw responsive to determining that the user has pressed on a touch-sensitive screen of the display device over a screw body of the graphical screw while moving location of the user's continued pressing along the touch-sensitive screen; and
- angularly pivoting the displayed graphical screw responsive to determining that the user has pressed on the touch-sensitive screen over a screw head and/or tip of the graphical screw while moving location of the user's continued pressing along the touch-sensitive screen.

5. The surgical implant planning computer of claim 3, wherein the operations to control angular orientation and location of the displayed graphical screw relative to the bone in the first and second images responsive to receipt of user inputs, comprise:
- selecting a length of the displayed graphical screw from among a set of defined lengths for surgical screws responsive to determining that the user has pressed on a touch-sensitive screen of the display device over a screw tip or a screw head of the graphical screw while moving location of the user's continued pressing along the touch-sensitive screen a measured distance,
- wherein the selected length is stored in the surgical plan data structure.

6. The surgical implant planning computer of claim 1, wherein the operations to control orientation and location of the displayed graphical screw relative to the bone in the first and second images responsive to receipt of user inputs, comprise:
- modifying a size and/or a rotational angle of the displayed graphical screw on the first and second images responsive to tracking motion of a user's hand relative to an input device.

7. The surgical implant planning computer of claim 1, wherein the operations further comprise:
- providing the surgical plan data structure to the robot to control movement of the robot arm relative to the robot base.

8. The surgical implant planning computer of claim 1, wherein the operations further comprise:
- controlling the motors responsive to content of the surgical plan data structure to regulate movement of the robot arm while positioning an end-effector, which is connected to the robot arm, relative to a patient; and
- controlling angular orientation and location of the displayed graphical screw responsive to the movement of the robot arm while the end-effector is positioned relative to the patient.

9. The surgical implant planning computer of claim 8, wherein the operations further comprise:
- controlling the motors to move the end-effector in a direction along a trajectory defined by the content of the surgical plan data structure; and
- controlling location of the displayed graphical screw responsive to the movement of the end-effector along the trajectory.

10. The surgical implant planning computer of claim 8, wherein the operations further comprise:
- while moving the end-effector along the trajectory, further controlling the motors to resist movement of the end-effector in a direction perpendicular to the trajectory until another operation is perform that cancels an end-effector trajectory constraint mode.

11. The surgical implant planning computer of claim 10, wherein the operations further comprise:
- prior to initiating the end-effector trajectory constraint mode, controlling the motors to move the end-effector in a direction upward away from the patient and then toward a location along the trajectory toward the patient;
- preventing initiation of the end-effector trajectory constraint mode before reaching the location along the trajectory; and
- controlling angular orientation and location of the displayed graphical screw responsive to the movement of the robot arm away from the patient and then toward the location along the trajectory.

12. A surgical implant planning computer comprising:
- at least one network interface connectable to an image database;
- a display device;
- at least one processor; and
- at least one memory storing program code that is executed by the at least one processor to perform operations comprising:
  - loading first and second images at different orientations from a computed tomography (CT) scan of a bone, which are received from the image database through the at least one network interface, into the at least one memory;
  - displaying the first and second images on the display device;
  - receiving a user's selection of a surgical screw from among a set of defined surgical screws;
  - displaying a graphical screw representing the selected surgical screw as an overlay on the displayed first and second images of the bone;
  - receiving as user inputs dragging of the displayed graphical screw to manipulate the angular orientation of the displayed graphical screw including pivoting the displayed graphical screw about the tip and about the head of the displayed graphical screw;
  - updating on the display device angular orientation and location of the displayed graphical screw relative to the bone in the first and second images responsive to receipt of the user inputs;
  - receiving as a second user input selecting and dragging of the selected screw to simulate an advancement of the selected screw into the bone;
  - updating on the display device the advancement of the selected screw only along a trajectory defined by the angular orientation of the selected screw in both the first and second images responsive to receipt of the second user input; and
  - storing an indication of the selected surgical screw and an angular orientation and a location of the displayed graphical screw in a surgical plan data structure responsive to user input, the surgical plan data structure being configured for use by a robot with a robot base coupled to a robot arm that is movable by motors relative to the robot base.

13. The surgical implant planning computer of claim 12, wherein the operations to display the graphical screw representing the selected surgical screw as an overlay on the first and second images of the bone, comprise:
   determining a trajectory along an axis of the graphical screw; and
   displaying a trajectory line that extends from adjacent to a tip of the graphical screw and along the trajectory to facilitate a user visually orienting and positioning the graphical screw relative to a desired insertion location on the bone.

14. The surgical implant planning computer of claim 13, wherein the operations to control angular orientation and location of the displayed graphical screw relative to the bone in the first and second images responsive to receipt of user inputs, comprise:
   translating a location of the displayed graphical screw responsive to determining that the user has pressed on a touch-sensitive screen of the display device over a screw body of the graphical screw while moving location of the user's continued pressing along the touch-sensitive screen; and
   angularly pivoting the displayed graphical screw responsive to determining that the user has pressed on the touch-sensitive screen over a screw head and/or tip of the graphical screw while moving location of the user's continued pressing along the touch-sensitive screen.

15. The surgical implant planning computer of claim 13, wherein the operations to control angular orientation and location of the displayed graphical screw relative to the bone in the first and second images responsive to receipt of user inputs, comprise:
   selecting a length of the displayed graphical screw from among a set of defined lengths for surgical screws responsive to determining that the user has pressed on a touch-sensitive screen of the display device over a screw tip or a screw head of the graphical screw while moving location of the user's continued pressing along the touch-sensitive screen a measured distance,
   wherein the selected length is stored in the surgical plan data structure.

16. The surgical implant planning computer of claim 12, wherein the operations further comprise:
   controlling angular orientation and location of the displayed graphical screw responsive to the movement of the robot arm while the end-effector is positioned relative to the patient.

17. The surgical implant planning computer of claim 12, wherein the operations further comprise:
   performing a registration setup mode comprising determining occurrence of a first condition indicating that a marker tracking camera can observe to track reflective markers that are on a fluoroscopy registration fixture, and further determining occurrence of a second condition indicating that the marker tracking camera can observe to track dynamic reference base markers attached to the robot arm and/or an end-effector connected to the robot arm;
   displaying on the display device an indication of when both of the first and second conditions occur; and
   determining that the registration setup mode is allowed to be marked satisfied when at least both of the first and second conditions are determined to occur.

18. The surgical implant planning computer of claim 17, wherein the operations further comprise:
   while both of the first and second conditions are determined to continue to occur, allowing operations to be performed to obtain a first intra-operative fluoroscopic image of the patient along a first plane and to obtain a second intra-operative fluoroscopic image of the patient along a second plane that is orthogonal to the first plane; and
   determining that a registration mode is allowed to be marked satisfied when the first and second intra-operative fluoroscopic images have been obtained.

19. The surgical implant planning computer of claim 18, wherein the operations further comprise:
   displaying the first and second intra-operative fluoroscopic images on the display device;
   displaying the graphical screw as an overlay on both of the first and second intra-operative fluoroscopic images;
   controlling angular orientation and location of the displayed graphical screw relative to a bone in the first and second intra-operative fluoroscopic images responsive to receipt of user inputs.

20. A method by a surgical implant planning computer, the method comprising:
   displaying on a display device first and second images at different orientations from a computed tomography (CT) scan of a bone with a CT image scanner;
   receiving a user's selection of a surgical screw from among a set of defined surgical screws;
   displaying a graphical screw representing the selected surgical screw as an overlay on the first and second images of the bone;
   receiving as user inputs dragging of the displayed graphical screw to manipulate the angular orientation of the displayed graphical screw including pivoting the displayed graphical screw about the tip and about the head of the displayed graphical screw;
   updating on the display device angular orientation and location of the displayed graphical screw relative to the bone in the first and second images responsive to receipt of the user inputs;
   receiving as a second user input selecting and dragging of the selected screw to simulate an advancement of the selected screw into the bone;
   updating on the display device the advancement of the selected screw only along a trajectory defined by the angular orientation of the selected screw in both the first and second images responsive to receipt of the second user input; and
   storing an indication of the selected surgical screw and an angular orientation and a location of the displayed graphical screw in a surgical plan data structure within a memory responsive to receipt of a defined user input.

* * * * *